US011160775B2

(12) United States Patent
Gurtner et al.

(10) Patent No.: US 11,160,775 B2
(45) Date of Patent: *Nov. 2, 2021

(54) TOPICAL AND TRANSDERMAL DELIVERY OF HIF-1 MODULATORS TO PREVENT AND TREAT CHRONIC WOUNDS

(71) Applicant: THE BOARD OF TRUSTEES OF THE LELAND STANFORD JUNIOR UNIVERSITY, Stanford, CA (US)

(72) Inventors: Geoffrey C. Gurtner, Portola Valley, CA (US); Jayakumar Rajadas, Cupertino, CA (US); Michael Gabriel Galvez, Palo Alto, CA (US); Evgenios Neofytou, Stanford, CA (US)

(73) Assignee: THE BOARD OF TRUSTEES OF THE LELAND STANFORD JUNIOR UNIVERSITY, Stanford, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/923,857

(22) Filed: Jul. 8, 2020

(65) Prior Publication Data

US 2020/0338024 A1 Oct. 29, 2020

Related U.S. Application Data

(63) Continuation of application No. 16/127,964, filed on Sep. 11, 2018, now Pat. No. 10,751,304, which is a continuation of application No. 15/623,898, filed on Jun. 15, 2017, now Pat. No. 10,098,857, which is a continuation-in-part of application No. 14/303,479, filed on Jun. 12, 2014, now abandoned, which is a continuation-in-part of application No. 12/577,006, filed on Oct. 9, 2009, now abandoned.

(60) Provisional application No. 61/104,599, filed on Oct. 10, 2008, provisional application No. 61/834,336, filed on Jun. 12, 2013.

(51) Int. Cl.
| | |
|---|---|
| *A61K 31/16* | (2006.01) |
| *A61K 9/00* | (2006.01) |
| *A61K 9/107* | (2006.01) |
| *A61K 9/70* | (2006.01) |
| *A61K 47/26* | (2006.01) |
| *A61K 47/32* | (2006.01) |
| *A61K 47/38* | (2006.01) |
| *A61K 9/06* | (2006.01) |

(52) U.S. Cl.
CPC ............ *A61K 31/16* (2013.01); *A61K 9/0014* (2013.01); *A61K 9/06* (2013.01); *A61K 9/1075* (2013.01); *A61K 9/7023* (2013.01); *A61K 9/7053* (2013.01); *A61K 9/7069* (2013.01); *A61K 47/26* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 4,397,867 A | 8/1983 | Blake | |
| 4,760,051 A | 7/1988 | Pickart | |
| 4,877,770 A | 10/1989 | Pickart | |
| 4,992,445 A | 2/1991 | Lawter et al. | |
| 5,001,139 A | 3/1991 | Lawter et al. | |
| 5,023,252 A | 6/1991 | Hsieh | |
| 5,047,427 A | 9/1991 | Williamson | |
| 5,382,574 A | 1/1995 | Jorgensen | |
| 5,676,968 A | 10/1997 | Lipp et al. | |
| 5,677,330 A | 10/1997 | Abraham et al. | |
| 6,117,437 A * | 9/2000 | Roreger ............... | A61K 9/7007 424/402 |
| 6,156,334 A | 12/2000 | Meyer-Ingold et al. | |
| 6,337,350 B1 | 1/2002 | Rahbar et al. | |
| 6,348,465 B1 | 2/2002 | Baker | |
| 6,465,504 B1 | 10/2002 | Lattmann et al. | |
| 6,576,653 B2 | 6/2003 | Du Bois | |
| 6,579,544 B1 | 6/2003 | Rosenberg et al. | |
| 6,737,421 B1 | 5/2004 | Lubish et al. | |
| 6,984,636 B2 | 1/2006 | Murphy et al. | |
| 8,507,649 B2 | 8/2013 | Lintner et al. | |
| 10,098,857 B2 | 10/2018 | Gurtner et al. | |
| 10,751,304 B2 | 8/2020 | Gurtner et al. | |
| 2003/0060408 A1 | 3/2003 | Bar Or et al. | |
| 2003/0082225 A1 | 5/2003 | Mason | |
| 2003/0086916 A1 | 5/2003 | Goligorsky et al. | |
| 2004/0059107 A1 | 3/2004 | Malfroy Camine et al. | |
| 2004/0151765 A1 | 8/2004 | Ritchie et al. | |

(Continued)

FOREIGN PATENT DOCUMENTS

| | | |
|---|---|---|
| EP | 1374868 A1 | 1/2004 |
| JP | H05-009114 A | 1/1993 |

(Continued)

OTHER PUBLICATIONS

Abaci et al.; Effect of diabetes mellitus on formation of coronary collateral vessels; Circulation; 99(17); pp. 2239-2242; May 1999.
Abbott et al.; The impact of diabetes on survival following myocardial infraction in men vs women. Franingham study; Jama; 260(23); pp. 3456-3460; Dec. 1988.
Adamis et al.; Increased vascular endothelial growth factor levels in the vitreous of eyes with proliferative diabetic retinopathy; American Journal of Opthalmology; 118(4); pp. 445-450; Oct. 1994.
Aiello et al.; Role of vascular endothelial growth factor in diabetic vascular complications; Kidney International; 58(77); pp. S113-S119; Sep. 2000.

(Continued)

*Primary Examiner* — Melissa L Fisher
(74) *Attorney, Agent, or Firm* — Shay Glenn LLP

(57) ABSTRACT

Compositions and methods are provided for the prevention and treatment of chronic wounds, including, without limitation, pressure ulcers and diabetic ulcers, by transdermal delivery of an agent that increases activity of HIF-1α in the wound.

15 Claims, 25 Drawing Sheets
(23 of 25 Drawing Sheet(s) Filed in Color)

(56) References Cited

U.S. PATENT DOCUMENTS

| | | | |
|---|---|---|---|
| 2005/0215468 | A1 | 9/2005 | Bar Or et al. |
| 2006/0100189 | A1 | 5/2006 | Gurtner et al. |
| 2006/0211746 | A1 | 9/2006 | Bergeron |
| 2006/0281748 | A1 | 12/2006 | Gurtner et al. |
| 2007/0104769 | A1 | 5/2007 | Feng et al. |
| 2007/0135369 | A1 | 6/2007 | Cooke et al. |
| 2009/0017439 | A1 | 1/2009 | Shimko et al. |
| 2009/0305963 | A1 | 12/2009 | Sukhatme et al. |
| 2010/0092546 | A1* | 4/2010 | Gurtner .................. A61K 9/06 424/449 |
| 2011/0159104 | A1 | 6/2011 | Teslenko |
| 2011/0212033 | A1 | 9/2011 | Tamarkin et al. |
| 2012/0207688 | A1 | 8/2012 | Guthery |
| 2012/0220651 | A1 | 8/2012 | Chevion et al. |
| 2013/0110132 | A1 | 5/2013 | Epstein et al. |
| 2014/0039069 | A1 | 2/2014 | Desai et al. |
| 2014/0364406 | A1 | 12/2014 | Gurtner et al. |
| 2014/0370078 | A1 | 12/2014 | Gurtner et al. |
| 2015/0174021 | A1 | 6/2015 | Campiche et al. |
| 2016/0039922 | A1 | 2/2016 | Attie |
| 2017/0296514 | A1 | 10/2017 | Miller et al. |
| 2018/0071265 | A1 | 3/2018 | Gurtner et al. |
| 2018/0193353 | A1 | 7/2018 | Gurtner |
| 2020/0046653 | A1 | 2/2020 | Gurtner |
| 2020/0253899 | A1 | 8/2020 | Wan et al. |

FOREIGN PATENT DOCUMENTS

| | | |
|---|---|---|
| JP | 10-120557 A | 5/1998 |
| WO | WO94/27594 A2 | 12/1994 |
| WO | WO00/19993 A2 | 4/2000 |
| WO | WO01/091774 A2 | 12/2001 |
| WO | WO02/098431 A1 | 12/2002 |
| WO | WO02/102345 A2 | 12/2002 |
| WO | WO03/049686 A2 | 6/2003 |
| WO | WO03/053997 A2 | 7/2003 |
| WO | WO2004/039430 A2 | 5/2004 |
| WO | WO2005/007192 A2 | 1/2005 |
| WO | WO2005/060986 A1 | 7/2005 |
| WO | WO2005/115379 A2 | 12/2005 |
| WO | WO2008/075207 A2 | 6/2008 |

OTHER PUBLICATIONS

Aiello et al.; Vascular endothelial growth factor in ocular fluid of patients with diabetic retinopathy and other retinal disorders; New England Journal of Medicine; 331(22); pp. 1430-1487; Dec. 1994.

Al-Mehdi et al.; Depolarization-associated iron release with abrupt reduction in pulmonary endothelial shear stress in situ; Antioxidants and Redox Signaling; 2(2); pp. 335-345; Jun. 2000.

Altavilla et al.; Inhibition of lipid peroxidation restores vascular endothelial growth factor expression and stimulates wound healing and angiogenesis in the genetically diabetic mouse; Diabetes; 50(3); pp. 667-674; Mar. 2001.

American Cancer Society; Cancer facts and figures 2017; 7 pages; retrieved from the internet (https://www.cancer.org/research/cancer-facts-statistics/all-cancer-facts-figures/cancer-facts-figures-2017.html) on Dec. 28, 2016.

American Society of Plastic Surgeons; Plastic surgery atatistics report: 2017; 25 pages; retrieved from the internet (https://www.plasticsurgery.org/documents/News/Statistics/2017/plastic-surgery-statistics-full-report-2017.pdf) on Jan. 9, 2019.

Andrews; Disorders of iron metabolism: New England Journal of Medicine; 341(26); pp. 1986-1995; Dec. 23, 1999.

Arora et al.; Cutaneous microcirculation in the neuropathic diabetic foot improves significantly but not completely after successful lower extremity revascularization; Journal of vascular Surgery; 35(3); pp. 501-505; Mar. 2002.

Asahara et al.; Bone marrow origin of endothelial progenitor cells responsible for postnatal vasculogenesis in physiological and pathological neovascularization; Circulation Research; 85(3); pp. 221-228; Aug. 6, 1999.

Asahara et al., Isolation of putative progenitor endothelial cells for angiogenesis; Science; 275(5302); pp. 964-966; Feb. 14, 1997.

Asahara et al; VEGF contributes to postnatal meovasoularization by mobilizing bone marrow-derived endothelial progenitor cells; The EMBO Journal; 18(14); pp. 3964-3872; Jul. 15, 1999.

Barnett et al.; Normal tissue reactions to radiotherapy: towards tailoring treatment dose by genotype; Nature Reviews Cancer; 9(2); pp. 134-142; 21 pages (Author Manuscript); Feb. 2009.

Bentzen; Preventing or reducing late side effects of radiation therapy: radiobiology meets molecular pathology; Nature Reviews Cancer; 6(9); pp. 702-713; Sep. 2006.

Bradley et al.; Survival of diabetic patients after myocardial infarction; The American Journal of Medicine; 20(2); pp. 207-216; Feb. 1956.

Brown; Expression of vascular permeability factoor (vascular endothelial growth factor) by epidermal keratinocytes during wound healing; Journal of Experimental Medicine; 176(5); pp. 1375-1379; Nov. 1992.

Brownlee; Biochemistry and molecular cell biology of diabetic complications; Nature; 414(6865); pp. 813-820; Dec. 2001.

Cameron et al.; Neurovascular dysfunction in diabetic rats. Potential contribution of autoxidation and free radicals examined using transition metal chelating agents.; The Journal of Clinical Investigation; 96(2); pp. 1159-1163; Aug. 1995.

Carmeliet et al.; Abnormal blood vessel development and lethality in embryos lacking a single VEGF allele; Nature; 380(6573); pp. 435-439; Apr. 4, 1996.

Caro et al.; Lifetime costs of complications resulting from type 2 diabetes in the U.S.; Diabetes Care; 25(3); pp. 476-481; Mar. 2002.

Chang et al.; Age decreases endothelial progenitor cell recruitment through decreases in hypoxia-induced factor 1 alpha stabilization during ischemia; Circulation; 116(24); pp. 2818-2829; Dec. 2007.

Chaston et al.; Iron chelators for the treatment of iron overload disease: Relationship between structure, redox activity, and toxicity; America Journal of Hematology; 73(3); pp. 200-210; 22 pages, retrieved from the internet (https://onlinelibrary.wiley.com/doi/pdf/10.1002/ajh.10348);Jul. 2003.

Chatterjee et al.; Inhibitors of poly (ADP-Ribose) synthetase protect rat proximal tubular cells against oxidant stress; Kidney International; 56(3); pp. 973-984; Sep. 1999.

Chekanov et al.; Deferoxamine enhances neovascularization and recovery of ischemic skeletal muscle in an experimental sheep model; The Annals of Thoracic Surgery; 75(1); pp. 184-189; Jan. 2003.

Chilian et al.; Microvascular occusions promote coronary collateral growth; American Journal of Physiology-Heart and Cicuatory Physiology; 258(4); pp. H1103-H1111; Apr. 1990.

Chou et al.; Decreased cardiac expression of vascular endothelial growth factor and its receptors in insulin-resistant and diabetic states: A possible explanation for impaired collateral formation in cardiac tissue; Circulation; 105(3); pp. 373-379; Jan. 22, 2002.

Chung et al.; Micro-computed tomography evaluation of human fat grafts in nude mice; Tissue Engineering Part C: Methods; 19(3); pp. 227-232; Jan. 4, 2013.

Church; Economic costs of diabetes in the U.S. in 2002; Diabetes Care; 26(3); pp. 917-932; Mar. 2003.

Clark et al.; Soft-tissue reconstruction of the foot and ankle. The Orthopedic Clinics of North America; 24(3); pp. 489-503; Jul. 1993.

Crosby et al.; Endothelial cells of hematopoietic origin make a significant contribution to adult blood vessel formation: Circulation Research; 87(9); pp. 728-730; Oct. 27, 2000.

Curio et al.; Decreased cultured endothelial cell proliferation in high glucose medium is reversed by antioxidants: new insights on the parthophysiological mechanisms of diabetic vascular complications; In Vitro Cellular and Developmental Biology; 28(11/12); pp. 787-790; Nov. 1992.

Delay et al.; Fat injection to the breast: technique results, and indications based on 880 procedures over 10 years; Aesthtic Surgery Journal; 29(5); pp. 360-376; Sep. 2009.

Diabetes Control and Complications Trial Research Grou; The effect of intensive treatment of diabetes on the development and

(56) References Cited

OTHER PUBLICATIONS progression of long-term complications in insulin-dependent diabetes mellitus; New England Journal of Medicine; 329(14); pp. 977-986; Sep. 30, 1993.
Donneys et al.; Deferoxamine expedites consolidation during mandibular distraction osteogenesis; Bone; 55(2); pp. 384-390; 25 pages; (Author Manuscript); Aug. 2013.
Donneys et al.; Localized deferoxamine injection augments vascularity and improves bony union in pathologic fracture healing after radiotherapy; Bone; 52(1); pp. 318-325; 23 pages (Author Manuscript); Jan. 2013.
Donneys et al; Deferoxamine restores callus size, mineralization, and mechanical strength in fracture healing after radiotherapy; Plastic and Reconstructive Surgery; 131(5); pp. 711e-719e; 13 pages (Author Manuscript); May 2013.
Dos Santos et al.; Amphiphilic molecules in drug delivery systems; Drug Delivery Systems: Avanced Technologies Potentially Applicable in Personalised Treatment, Adavances in Predictive, Preventive and Personalised Medicine 4, DOI 10.1007/978-94-007-6010-3_2: Springer Science + Business Media Dordrecht; pp. 35-85; (year of pub. sufficiently earlier than effective US filing dated and any foreign priority date) 2013.
Du et al.; Hyperglycemia inhibits endothelial nitric oxide synthase activity by posttranslational modification at the akt site; Journal of Clinical Investigation; 103(9); pp. 1341-1348; Nov. 2001.
Du et al.; Insulin resistance causes proatherogenic changes in arterial endothelium by increasing fatty acid oxidation-induced superoxide production; The Journal of Clinical Investigation; 116(4); pp. 1071-1080; Apr. 3, 2006.
Duscher et al.; Comparison of the hydroxylase inhibitor dimethyloxalyiglycine and the iron chelator deteroxamine in diabetic and aged wound healing; Plastic and Reconstructive Surgery; 139(3); pp. 695e-706e: 18 pages, (Author Manuscript); Mar. 2017.
Duscher et al.; Fibroblast-specific deletion of hypoxia inducible factor-1 critically impairs murine cutaneous neovascularization and wound healing; Plastic and Reconstructive Surgery; 136(5); pp. 1004-1013; 15 pages, (Author Manuscript); Nov. 2015.
Duscher et al., Transdermal deferoxamine prevents pressure-induced diabetic uclers; Proceedings of the National Academy of Sciences; 112(1); pp. 94-99; 6 pages; (Author Manuscript); Jan. 6, 2015.
Eto et al.; The fate of adipocytes after nonvascularized fat grafting: evidence of early death and replacement of adipocytes; Plastic and Reconstructive Surgery; 129(5); pp. 1081-1092; May 2012.
Farberg et al.; Deferoxamine enhances bone regeneration in mandibular distraction osteogenesis; Plastic and Reconstructive Surgery; 133(3); pp. 666-671; 11 pages (Author Manuscript); Mar. 2014.
Felice et al.; Deferoxamine administration delivers translational optimization of distraction osteogenesis in the irradiated mandible; Plastic and Reconstructive Surgery; 132(4); pp. 542e-548e; 11 pages (Author Manuscript); Oct. 2013.
Fernandez-Real et al.; Cross-talk between iron metabolism and diabetes; Diabetes; 51(8); pp. 2348-2354; Aug. 2002.
Ferrara et al.; The biology of VEGF and its receptors; Nature Medicine; 9(6); pp. 669-676; Jun. 2003.
Forsythe et al.; Activation of vascular endothelial growth factor, gene transcription by hypoxia-inducible factor 1; Molecular and Cellular Biology; 16(9); pp. 4604-4613; Sep. 1996.
Fraga et al; Iron toxicity and antioxidant nutrients; Toxicology; 180(1); pp. 23-32; Oct. 2002.
Frank et al.; Regulation of vascular endothelial growth factor expression in cultured keratinocytes. Implications for normal and impaired wound healing; Journal of Biological Chemistry; 270(21); pp. 12607-12613; May 26, 1995.
Fujiwara et al.; Extracellular superoxide dismutase deficiency impairs wound healing in adavance age by reducing neovascularization and fibroblast function; Experimental Dermatology; 25(3); pp. 206-211; 14 pages, (Author Manuscript); Mar. 2016.
Galiano et al.; Quantitative and reproducible murine model of excisional wound healing; Wound Repair and Regeneration; 12(4); pp. 485-492; Aug. 2004.
Garcia et al.; Morbidity and mortality in diabetes in the framingham population. Sixteen year follow-up study; Diabetes; 23(2); pp. 105-111; Feb. 1974.
Garza et al.; Studies in fat grafting: Part III. Fat grafting irradiated tissue-improved skin quality and decreased fat graft retention; Plastic and Reconstructive Surgery; 134(2); pp. 249-257; 15 pages; (Author Manuscript); Aug. 2014.
Gaynes et al.; National Nosocomial Infections Surveillance System; plans for the 1990s and beyond; Am J Med; 91(3) Suppl 2; pp. S116-S120; Sep. 16, 1991.
Giardino et al.; BCL-2 expression or antioxidants prevent hyperglycemia-induced formation of intracellular advanced glycation endproducts in bovine endothelial cells; The Journal of Clinical Investigation; 97(6); pp. 1422-1428; Mar. 15, 1996.
Gill et al.; Vascular trauma induces rapid but transient mobilization of VEGFR2(+)AC133(+) endothelial precursor cells; Circulation Research; 88(2); pp. 167-174; Feb. 2001.
Gkouvatsos et al.; Regulation of iron transport and the role of transferrin; Biochimica et Biophysica Acta (BBA)—General Subjects; 1820(3); pp. 188-202; Mar. 2012.
Goova et al.; Blockade of receptor for advanced glycation end-products restores effective wound healing in diabetic mice; The American Journal of Pathology; 159(2); pp. 513-525; Aug. 2001.
Grundy; Cardiovascular and Metabolic risk factors: How can we improve outcomes in the high-risk patient?; The American Journal of Medicine; 120(9); pp. S3-S8; Sep. 2007.
Guzik et al.; Mechanisms of increased vascular superoxide production in human diabetes mellitus; Role of NAD(P)H oxidase and endothelial nitric oxide synthase; Circulation; 105(14); pp. 1656-1662; Apr. 2002.
Haffner et al.; Mortality from coronary heart disease in subjects with type 2 diabetes and in nondiabetic subjects with and without prior myocardial infrarction; New England Journal of Medicine; 339(4); pp. 229-234; Jul. 23, 1998.
Haffner; Abdominal adiposity and cardiometabolic risk; Do we have all the answers?; The American Journal of Medicine; 120(9); pp. S10-S16; Sep. 2007.
Hammes et al.; Benfotiamine blocks three major pathways of hyperglycemic damage and prevents experimental diabetic retinopathy; Nature Medicine; 9(3); pp. 294-299; Mar. 2003.
Harris et al.; Prevalence of diabetes, impaired fasting glucose, and impaired glucose tolerance in U.S. adults. The third national health and nutrition examination survey, 1988-1994; Diabetes Care; 21(4); pp. 518-524; Apr. 1998.
Harrop et al.; Contributing factors to surgical site infections; JAAOS—J Am Acad Orthop Surg; 20(2); pp. 94-101; Feb. 1, 2012.
Hartzen et al.; The antibacterial activity of a siderophonre: 3. The activity of deferoxamine in vitro and its influence on the effect of antibiotics against *E coli,* P mirabilis and coagulase-negative *Staphylococci;* APMIS; 102(1-6); pp. 219-226; Jan. 1994.
Hattori et al.; Deferoxamine improves coronary vascular responses to sympathetic stimulation in patients with type 1 diabetes mellitus; European journal of Nuclear Medicine and Molecular Imaging; 29(7); pp. 891-898; Jul. 2002.
Hattori et al.; Vascular endothelial growth factor and angiopoietin-1 stimulate postnatal hematopoiesis by recruitment of vasculogenic and hematopoietic stem cells; Journal or Experimental Medicine; 193(9); pp. 1005-1014; May 2001.
Helfant et al.; Functional importance of the human coronary collateral circulation; New England Journal of Medicine; 284(23); pp. 1277-1281; Jun. 10, 1971.
Hershko et al.; ICL670A: a new synthetic oral chelator: evaluation in hypertransfused rats with selective radioiron probes of hepatocellular and reticuloendothelial iron stores and in iron-loaded rat heart cells in culture; Blood; 97(4); pp. 1115-1122; Feb. 2001.
Hiller et al.; Diabetic retinopathy and cardiovascular disease in type II diabetics. The framingham study and the framingham eye study; American Journal of Epidemiology; 128(2); pp. 402-409; Aug. 1988.

(56) References Cited

OTHER PUBLICATIONS

Howard et al.; Prevention conference VI: Diabetes and cardiovascular disease: Writing group I: Epidemiology; Circulation; 105(18); pp. e132-137; 6 pages; (Author Manuscript); May 2002.

Hymes et al.; Radiation dermatitis: clinical presentation, pathophysiology, and treatment; Journal of the American Academy of Dermatology; 54(1); pp. 28-46; Jan. 2006.

Ihnat et al.; Solution equilibria of deferoxamine amides; Journal of Pharmaceutical Sciences; 91(7); pp. 1733-1741; Jul. 2002.

Isner et al.; Angiogenesis and vasculogenesis as therapeutic strategies for postnatal neovascularization; The Journal of Clinical Investigation; 103(9); pp. 1231-1236; May 1999.

Iyer et al.; Cellular and developmental control of O2 homeostatis by hypoxia-inducible factor 1 alpha; Genes and Development; 12(2); pp. 146-162; Jan. 15, 1998.

Jacobson et al.; Vessel-depleted neck: techniques for achieving microvascular reconstruction; Head and Neck: Journal for the Sciences and Specialities of the Head and Neck; 30(2); pp. 201-207; Feb. 2008.

Jude et al.; Peripheral arterial disease in diabetic and nondiabetic patients: a comparison of severity and outcome; Diabetes Care; 24(8); pp. 1433-1437; Aug. 2001.

Kalka et al; Vascular endothelial growth factor (165) gene transfer augments circulating endothelial progenitor cells in human subjects; Circulation Research; 36(12); pp. 1193-1202; Jun. 2000.

Kannel et al.; Diabetes and cardiovascular risk factors: the framingham study; Circulation; 59(1); pp. 8-13; Jan. 1979.

Kip et al.; Differential influence of diabetes mellitus on increased jeopardized myocardium after initial angioplasty or bypass surgery: Bypass angioplasty revascularization investigation; Circulation; 105(6); pp. 1914-1920; Apr. 23, 2002.

Kipshidze et al.; Therapeutic angiogenesis for patients with limb ischemia by utilization of fibrin meshwork. Pilot randomized controlled study; International Angiology; 1(4); pp. 349-355; 8 pages, (Author Manuscript); Dec. 2003.

Kontoghorghes et al.; The design and development of deperiprone (L1) and other iron chelators for clinical use: targeting methods and application propects; Current Medicinal Chemistry; 11(16); pp. 2161-2183; Aug. 2004.

Kreilgaard; Influence of microemulsions on cutaneous drug delivery. Advanced drug delivery reviews; 54(1); pp. S77-S98; Nov. 1, 2002.

Kress et al.; The relationship between intracellular free iron and cell injury in cultured neurons, astrocytes, and oligodendrocytes; Journal of Neuroscience; 22(14); pp. 5848-5855; Jul. 15, 2002.

Lawrence et al.; Microemulsion-based media as novel drug delivery systems; Advanced Drug Delivery Reviews; 64; pp. 175-193; Sep. 13, 2012.

Lee et al.; Hypoxia-inducible factor (HIF-1alpha): its protein stability and biological functions; Exp Mol Med; 36(1); pp. 1-12; Feb. 2004.

Lerman et al.; Cellular dysfunction in the diabetic fibroblast: Impairment in migration, vascular endothelial growth factor production and response to hypoxia; The American Journal of Pathology; 162(1); pp. 303-312; Jan. 2003.

Lim et al.; Autologous fat transplantation in the craniofacial patient: the UCLA experience; The Jouranl of Craniofacial Surgery; 23(4); pp. 1061-1066; Jul. 2012.

Luan et al.; Cell-assisted lipotransfer improves volume retention in irradiated recipient sites and rescues radiation-induced skin changes; Stem Cells; 34(3); pp. 668-673; Mar. 2016.

Lukanov et al.; Molecular thermodynamic modeling of reverse micelles and water-in-oil microemulsions; Langmuir; 32(13); pp. 3100-3109; Mar. 25, 2016.

Margolis et al.; Risk factors for delayed healing of neuropathic diabetic foot ulcers: A pooled analysis; Archives of dermatology; 136(12); pp. 1531-1535; Dec. 2000.

Marsh et al.; Hypoxic induction of vascular endothelial growth factor is marked decreased in diabetic individuals who do not develop retinopathy; Diabetes Care; 23(9); pp. 1375-1380; Sep. 2000.

Meijler et al.; Synthesis and evaluation of iron chelators with masked hydrophilic moieties; Journal of the American Chemical Society, 124(43); pp. 12666-12667; Oct. 30, 2002.

Mericli et al.; Deferoxamine mitigates radiation-induced tissue injury in a rat irradiated TRAM flap model; Plastic and reconstructive surgery; 135(1); pp. 124e-134e; Jan. 2015.

Momeni et al.; Clinical use of deferoxamine in distraction osteogenesis of irradiated bone; The Journal of Craniofacial Surgery; 27(4); pp. 880-882; 10 pages (Author Manuscript); Jun. 2016.

Moreau-Marquis el al.; Tobramycin and FDA-approved iron chelators eliminate Pseudomonas aeruginosa biofilms on cystic fibrosis cells; Am J Respir Cell Mol Biol; 41(3); pp. 305-313; Sep. 2009.

Moreno-Navarrete et al.; Fine-tuned iron availability is essential to achieve optimal adipocyte differentiation and mitochondrial biogenesis; Diabetologia; 57(9); pp. 1957-1967; Sep. 2014.

Muha; Local wound care in diabetic food complications. Aggressive risk management and ulcer treatment to avoid amputation; Postgraduate Medicine; 106(1); pp. 97-102; Jul. 1999.

Mulder et al; Enhanced healing of ulcers in patients with diabetes by topical treatment with glycyl-l-histidyl-l-lysine copper; Wound Repair and Regeneration; 2(4); pp. 259-269; Oct. 1994.

Nagler et al.; Novel protection strategy against x-ray-induced damage to salivary glands; Radiation Research Society; 149(3); pp. 271-276; Mar. 1998.

Narang et al.; Stable drug encapsulation in micelles and microemulsions: Intl. Journal of Pharmaceutics; 345(1-2); pp. 9-25; Sep. 8, 2007.

National Cancer Institute; Head and neck cancers; 11 pages; retrieved from the internet ( https://www.cancer.gov/types/head-and-neck/head-neck-fact-sheet) on Jan. 9, 2019.

Nishikawa et al.; Normalizing mitochondrial superoxide production blocks three pathways of hyperglycaemic damage; Nature; 404(6779); pp. 787-790; Apr. 2000.

Nissen et al.; Vascular endothelial growth factor mediates angiogenic activity during the proliferative phase of wound healing; The American Journal of Pathology; 152(6); pp. 1445-1452; Jun. 1998.

Novartis Pharmaceuticals Corporation; Desferal deferoxamine mesylate for injection USP vials Rx only prescribing information; 8 pages; retrieved from the internet (https://www.pharma.us.novartis.com/sites/www.pharma.us.novartis.com/files/desferal.pdf) on Oct. 21, 2019.

Obrosova et al.; Aldose reductase inhibitor fidarestat prevents retinal oxidative stress and vascular edothelial growth factor overexpression in streptozotocin-diabetic rats; Diabetes; 52(3); pp. 864-871; Mar. 2003.

Ozer; The role of iron on breast cancer stem-like cells; Cellular and Molecular Biology; 62(4); pp. 25-30; Apr. 30, 2016.

Palumbo et al.; Diabetes mellitus: Incidence, prevalence, survivorship, and causes of death in Rochester, Minnesota, 1945-1970; Diabetes; 25(7); pp. 566-573; Jul. 1976.

Partamian et al.; Acute myocardial infarction in 258 cases of diabetes. Immediate mortality and five-year survival; New England Journal of Medicine; 273(9); pp. 455-461; Aug. 26, 1965.

Pedchenko et al; Desferrioxamine suppresses experimental allergic encephalomyelitis induced by MBP in SJL mice; Journal of Neuroimmunology; 84(2); pp. 188-197; Apr. 1998.

Pelosi et al.; Identification of the hemangioblast in postnatal life; Blood; 100(9); pp. 3203-3208; Nov. 2002.

Peters et al.; Vascular endothelial growth factor receptor expression during embryogenesis and tissue repair suggests a role in endothelial differentiation and blood vessel growth; Proceedings of the National Academy of Sciences; 90(19); pp. 8915-8919; Oct. 1993.

Pochon et al.; A novel derivative of the chelon desferrioxamine for site-specific conjugation to antibodies; International Journal of Cancer; 43(6); pp. 1188-1194; Jun. 1989.

Price et al.; Chelating activity of advanced glycation end-product inhibitors; Journal of Biological Chemistry; 276(52); pp. 48967-48972; Dec. 2001.

(56) References Cited

OTHER PUBLICATIONS

Rennert et al.; Diabetes impairs the angiogenic potential of adipose-derived stem cells by selectively depleting cellular subpopulations; Stem Cell Research and Therapy; 5(3):79; doi:10.1186/scrt468; 12 pages; Sep. 2014.
Ress et al.; Free radical damage in acute nerve compression; Annals of Plastic Surgery; 34(4); pp. 388-395; Apr. 1995.
Richard et al.; p42/p44 mitogen-activated protein kinases phosphorylate hypoxia-inducible factor 1 alpha (HIF-1 alpha) and enhance the transcriptional activity of HIF-1; Journal of Biological Chemistry; 274(46); pp. 32631-32637; Nov. 12, 1999.
Rivard et al.; Rescue of diabetes-related impairment of angiogenesis by intramuscular gene therapy with adeno-VEGF; American Journal of Pathology; 154(2); pp. 355-363; Feb. 1999.
Rose et al.; Deferoxamine stability in intravenous solution; Annal of the New York Academy of Sciences; 850; pp. 488-489; Jun. 1998.
Ryan; Ionizing radiation: the good, the bad, the bad, and the ugly; Journal of Investigative Dermatology; 132(3); pp. 985-993; Mar. 2012.
Salvemini et al.; Superoxide dismutase mimetics; Pulmonary Pharmacology and Therapeutics; 15(5); pp. 439-447; Oct. 2002.
Sang et al.; MAPK signaling up-regulates the activity of hypoxia-inducible factors by its effects on p300; Journal of Biological Chemistry; 278(16); pp. 14013-14019; Apr. 18, 2003.
Schatteman et al.; Blood derived angioblasts accelerate blood-flow restoration in diabetic mice; The Journal of Clinical Investigatiion; 106(4); pp. 571-578; Aug. 2000.
Schratzberger et al.; Reversal of experimental diabetic neuropathy by VEGF gene transfer; The Journal of Clinical Investigation; 107(9); pp. 1083-1092; May 2001.
Schwartz et al.; Coronary bypass graft patency in patients with diabetes in the bypass angioplasty revascularization investigation (BART); Circulation 106(21); pp. 2652-2658; Nov. 19, 2002.
Semenza et al., A nuclear factor induced by hypoxia via de novo protien synthesis blinds to the human erythropoietin gene enhancer at a site required for transcriptional activation; Molecular and Cellular Biology; 12(12); pp. 5447-5454; Dec. 1992.
Semenza et al.; Hypoxia-Inducible nuclear factors bind to an enhancer element located 3' to the human erythropoietin gene; National Academy of Sciences; 83(13); pp. 5680-5684; Jul. 1991.
Shi et al., Evidence for circulating bone marrow-derived endothelial cells; Blood; 92(2); pp. 362-367; Jul. 1998.
Shweiki et al.; Vascular endothelial growth factor induced by hypoxia may mediate hypoxia-initiated angiogenesis; Nature; 359(6398); pp. 843-845; Oct. 1992.
Siebert et al.; The inframammary extended circumflex scapular flap: an aesthetic improvement of the parascapular flap; Plastic and Reconstructive Surgery; 99(1); pp. 70-77; Jan. 1997.
Silhi.; Diabetes and wound healing; Journal of Wond Care; 7(1); pp. 47-51; Jan. 1998.
Simovic et al.; Improvement in chronic ischemic neuropathy after intramuscular phVEGF165 gene transfer in patients with critical limb ischemia; Archives of Neurology; 58(5); pp. 761-768; May 2001.
Soutoglou et al.; Acetylation regulates transcription factor at multiple levels; Molecular Cell; 5(4); pp. 745-751; Apr. 2000.
Spear et al.; Fat injection to correct contour deformities in the reconstructed breast; Plastic and Reconstructive Surgery; 116(5); pp. 1300-1305; Oct. 2005.
Stadler et al.; Development of a simple, noninvasive, clinically relevant model of pressure ulcers in the mouse; J Invest Surg; 17(4); pp. 221-227; Jan. 1, 2004.
Suga et al.; Adipose tissue remodeling under ischemia: death of adipocytes and activation of stem/progenitor cells; Plastic and Reconstructive Surgery; 126(6); pp. 1911-1923; Dec. 2010.
Takahashi et al.; Ischemia and cytokine-induced mobilization of bone marrow-derived endothelial progenitor cells for neovascularization; Nature Medicine; 5(4); pp. 434-438; Apr. 1999.
Talegaonkar et al.; Microemulsions: A novel approach to enhanced drug delivery; Recent patents on drug delivery and formulation; 2(3); pp. 238-257; Nov. 2008.
Taniyama et al.; Therapeutic angiogenesis induced by human hepatocyte growth factor gene in rat diabetic hind limb ischemia model: Molecular mechanisms of delayed angiogenesis in diabetes; Circulation; 104(19); pp. 2344-2350; Nov. 2001.
Temiz et al.; Effects of deferoxamine on fat graft survival; Facial Plastic Surgery; 32(04); pp. 438-443; Aug. 2016.
Tepper et al.; Human endothelial progenitor cells from type II diabetes exhibit impaired proliferation, adhesion, and incorporation into vascular structures; Circulation; 106(22); pp. 2781-2786; Nov. 26, 2002.
Thangarajah et al.; HIF-1alpha dysfunction in diabetes; Cell Cycle; 9(1); pp. 75-79; Jan. 2010.
Thangarajah et al.; The molecular basis for impaired hypoxia-induced VEGF expression in diabetic tissues; Proceedings of the Natiional Academy of Sciences; 106; pp. 13505-13510; doi:10.1073/pnas.0906670106; 6 pages; Jul. 27, 2009.
Tooke; Microvasculature in diabetes; Cardiovascular Research; 32(4); pp. 764-771; Oct. 1996.
Torti et al.; Iron and cancer: more ore to be mined; Nature Reviews Cancer; 13(5); pp. 342-355; 33 pages (Author Manuscript); May 2013.
Trivedi et al.; Nanomicellar formulation for sustained drug delivery: strategies and underlying principles; Nanomedicine (Lond); 5(3); pp. 485-505; Apr. 2010.
Uemura et al.; Disbetes mellitus enchances vascular matrix metalloproteinase activity: Role of oxidative stress; Circulation Research; 88(12); pp. 1291-1298; Jun. 22, 2001.
Uusitupa et al.; 5-Year incidence of atherosclerotic vascular disease in relation to general risk factors, insulin level, and abnormalities in lipoprotein composition in non-insulin-dependent diabetic and nondiabetic patients; Circulation; 82(1); pp. 27-36; Jul. 1990.
Van Asbeck et al.; Inhibition of bacterial multiplication by the iron chelator deferoxamine: potentiating effect of ascorbic acid; Eur J. Clin Microbiol; 2(5); pp. 426-431; Oct. 1, 1983.
Van Asbeck et al.; Synergy between the iron chelator deferoxamine and the antimicrobial agents gentamicin, chloramphenicol, cefalothin, cefotiam and cefsulodin; Eur J Clin Microbiol; 2(5); pp. 432-438; Oct. 1, 1983.
Vrignaud et al.; Reverse micelle-loaded lipid nanocarriers: a novel drug delivery system for the sustained release of doxorubicin hydrochloride; European Journal of Pharmacetics and Biopharmaceutics; 79(1); pp. 197-204; Sep. 2011.
Wakisaka et al.; Epstein-Barr virus latent membrane protein 1 induces synthesis of hypoxia-inducible factor 1alpha; Mol Cell Biol; 24(12); pp. 5223-5234; Jun. 15, 2004.
Waltenberger; Impaired collateral vessel development in diabetes: Potential cellular mechanisms and therapeutic implications; Cardiovascular Research; 49(3); pp. 554-560; Feb. 2001.
Wang et al.; Local injection of deferoxamine improves neovascularization in ischemic diabetic random flap by increasing HIF-1alpha and VEGF expression; Plos one; 9(6); e100818; 8 pages; Jun. 25, 2014.
Weinstein et al.; Deferoxamine decreases necrosis in dorsally based pig skin flaps; Otolaryngology—Heand and Neck Surgery; Offical Journal of American Academy of Otolaryngology—Head and Neck Surgery; 101(5); pp. 559-561; Nov. 1989.
Wend et al.; Mimic hypoxia improves angiogenesis in ischaemic random flaps; Journal of Plastic, Reconstructive and Aesthetic Surgery; 63(12); pp. 2152-2159; Dec. 2010.
Wilson; Diabetes mellitus and coronary heart disease; American Journal of Kidney Diseases; 32(5); pp. S89-S100; Nov. 1998.
Wong et al.; Microvascular reconstruction in the vessel-depleted neck; Current Opinion in Otolaryngology and Head and Neck Surgery; 18(4); pp. 223-226; Aug. 2010.
Yamasaki et al.; Deferoxamine for advanced hepatocellular carcinoma; New England Journal of Medicine; 365(6); pp. 576-578; Aug. 11, 2011.
Yarnold et al.; Pathogenetic mechanisms in radiation fibrosis; Radiotherapy and Oncology; 97(1); pp. 149-161; Oct. 2010.

(56) References Cited

OTHER PUBLICATIONS

Yarom et al.; Human coronary microvessels in diabetes and ischaemia morphometric study of autopsymaterial; Journal of Pathology; 166(3); pp. 265-270; Mar. 1992.

Yu et al.; Iron chelators for the treatment of cancer; Current Medicinal Chemistry; 19(17); pp. 2689-2702; Jun. 2012.

Zanger et al.; CREB binding protein recruitment to the transcription complex requires growth factor-dependent phosphorylation of ites GF box; Molecular Cell; 7(3); pp. 551-558; Mar. 2001.

Zhan et al.; Excess length of stay, charges, and mortality attributable to medical injuries during hospitalization; 290(14); pp. 1868-1874; Oct. 8, 2003.

Zimmet et al.; Global and societal implications of the diabetes epidemic; Nature; 414(6865); pp. 782-787; Dec. 2001.

Zuanetti et al.; Influence of diabetes on mortality in acute myocardial infarction: Data from the GISSI-2 study; American College of Cardiology; 22(7); pp. 1788-1794; Dec. 1993.

Arane-Conejo et al.; Physiopathology of complications of diabetic foot; Gac. Med. Mex.; 193(3); pp. 255-264; (English Abstract) May-Jun. 2003.

Brem et al.; Healing of elderly patients with diabetic foot ulcers, venous stasis ulcers, and pressure ulcers; Surgical Technology International; vol. 11; pp. 161-167; 2001.

Kip et al.; Coronary angioplasty in diabetic patients. The national heart, lung, and blood institute percutaneous transluminal coronary angioplasty registry; Circulation; 94(8); pp. 1818-1825: (Author Manuscript) Oct. 1996.

Mann et al.; Management of acute iron overdose; Clinical Pharmacy; 8(6); pp. 428-440; (Abstract Only) Jun. 1989.

Tuomilehto et al.; Diabetes mellitus as a risk factor for death from stroke. Prospective study of the middle-aged finnish population; Stroke; 27(2); pp. 210-215; (Author Manuscript) Feb. 1996.

Gurtner; U.S. Appl. No. 17/041,108 entitled "Topical and transdermal delivery of an iron chelator to prevent and treat chronic wounds," filed Sep. 24, 2020.

Gurtner; U.S. Appl. No. 17/273,855 entitled "Iron chelators for treating aesthetic skin conditions," filed Mar. 15, 2021.

\* cited by examiner

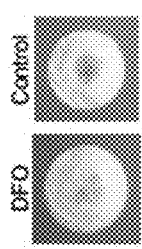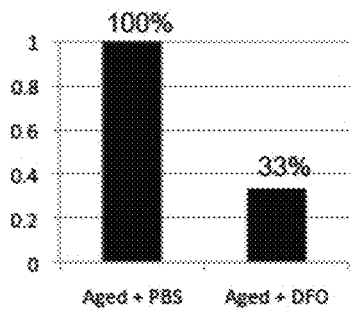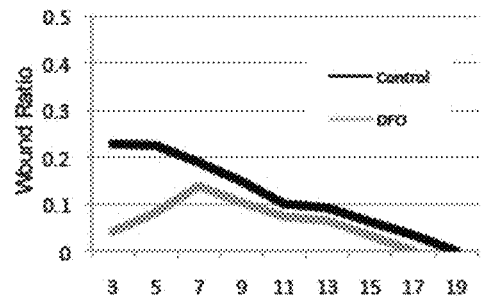
FIG. 1A FIG. 1B FIG. 1C
FIG. 2A
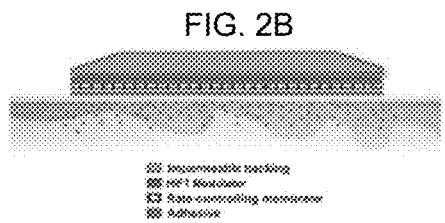
FIG. 2B
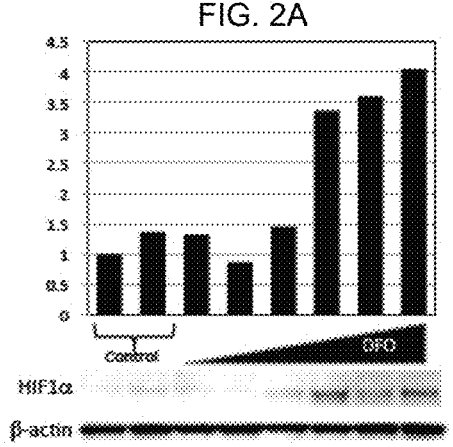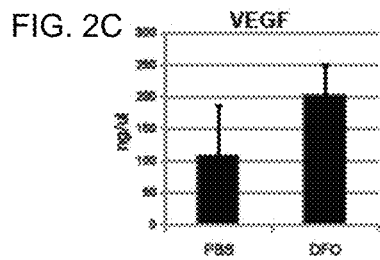
FIG. 2C
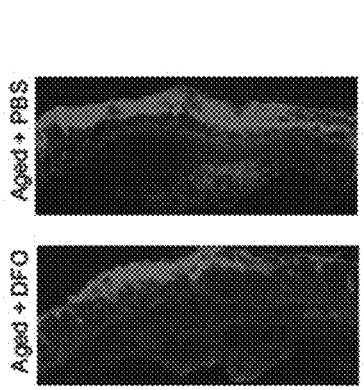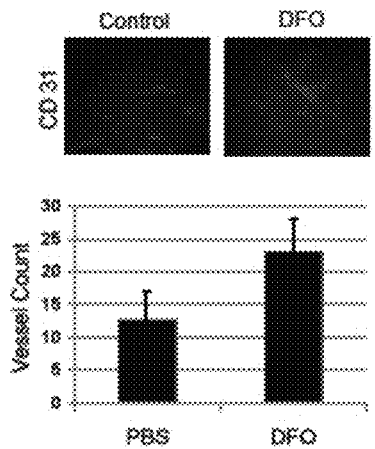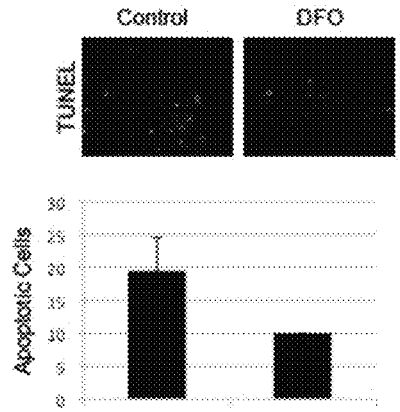
FIG. 3A FIG. 3B FIG. 3C FIG. 4
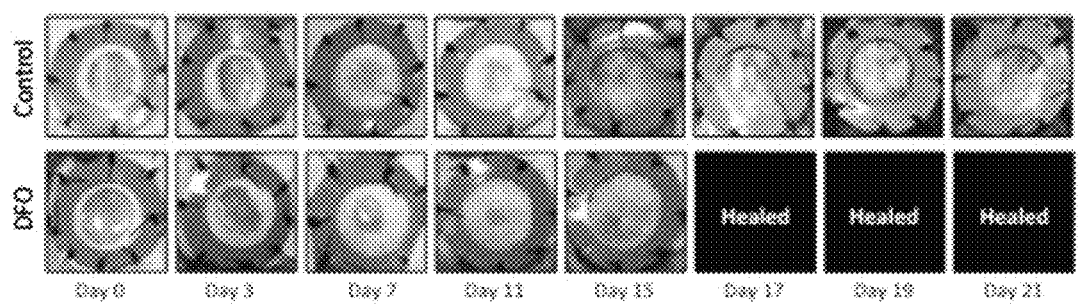
FIG. 5A
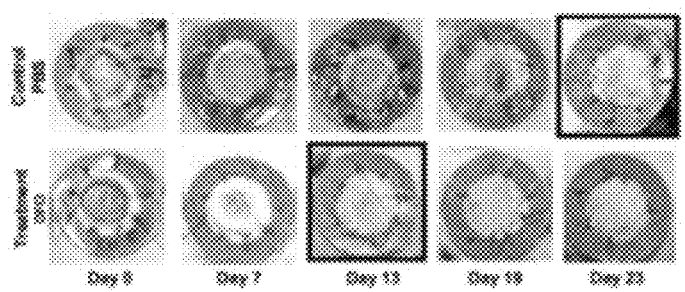
FIG. 5B
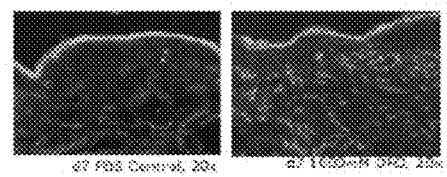
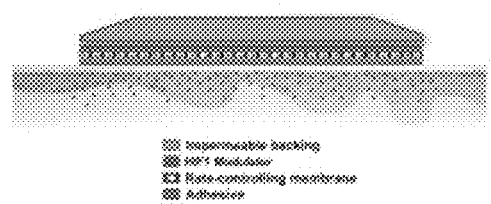
FIG. 6A
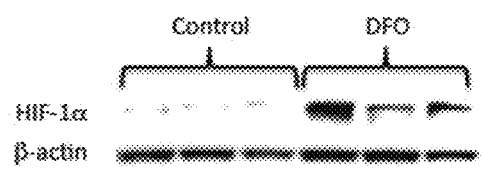
FIG. 6B
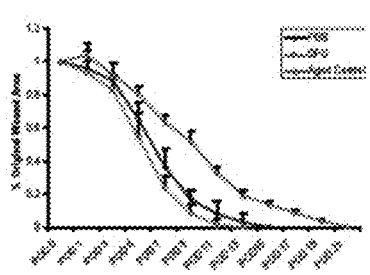
FIG. 7A
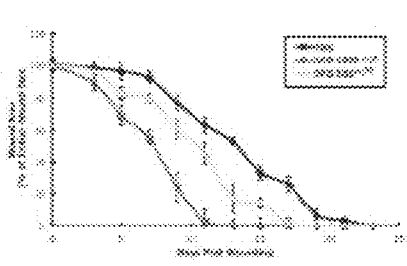
FIG. 7B
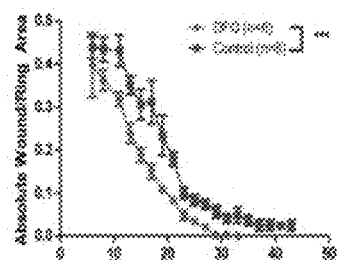
FIG. 7C

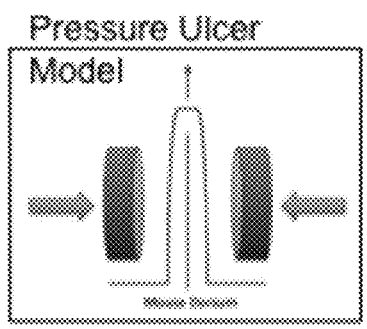
FIG. 8A
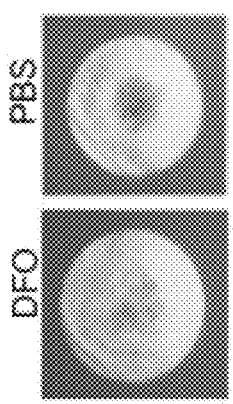
FIG. 8B
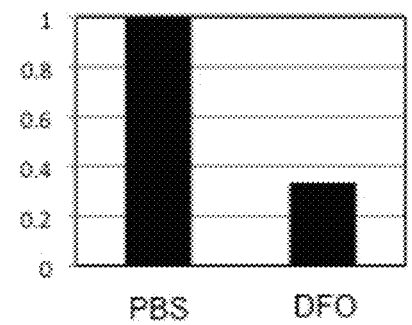
FIG. 8C
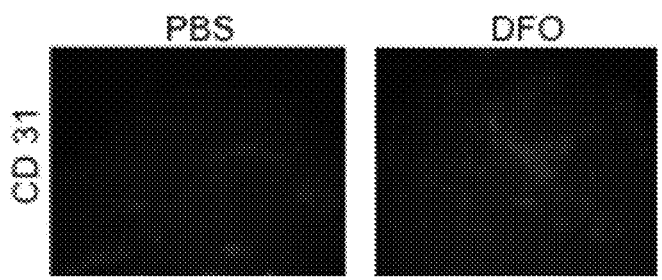
FIG. 8D
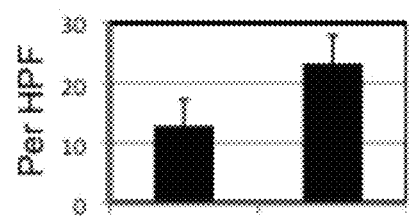
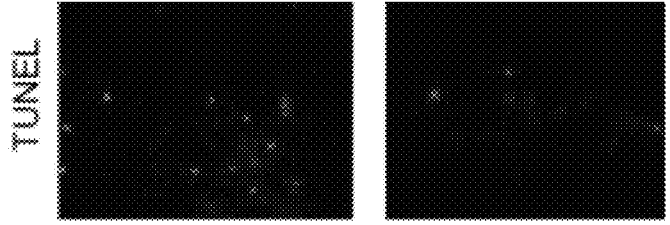
FIG. 8E
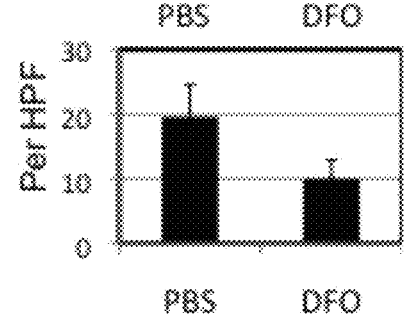
FIG. 9A
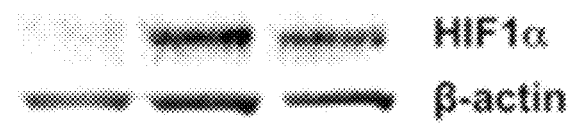
FIG. 9B
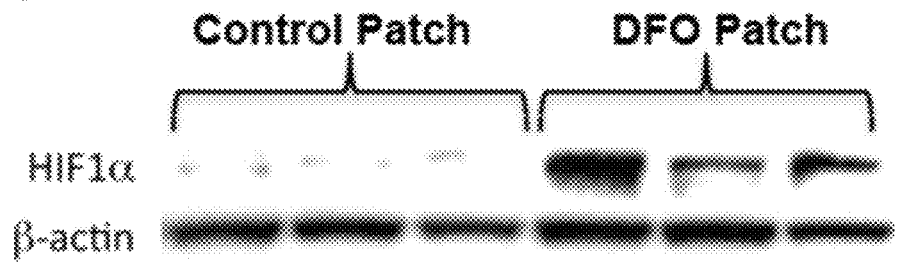

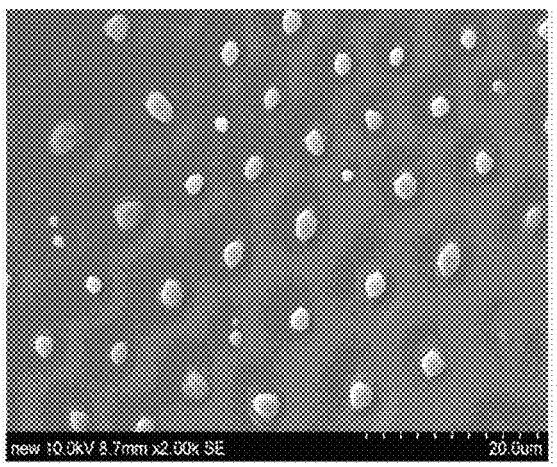
FIG. 10A 0 Hours
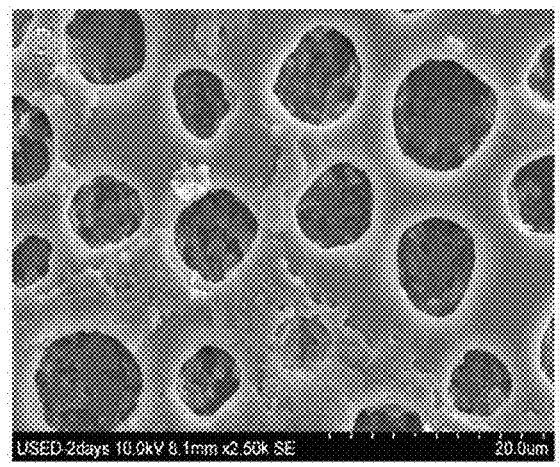
FIG. 10B 48 Hours
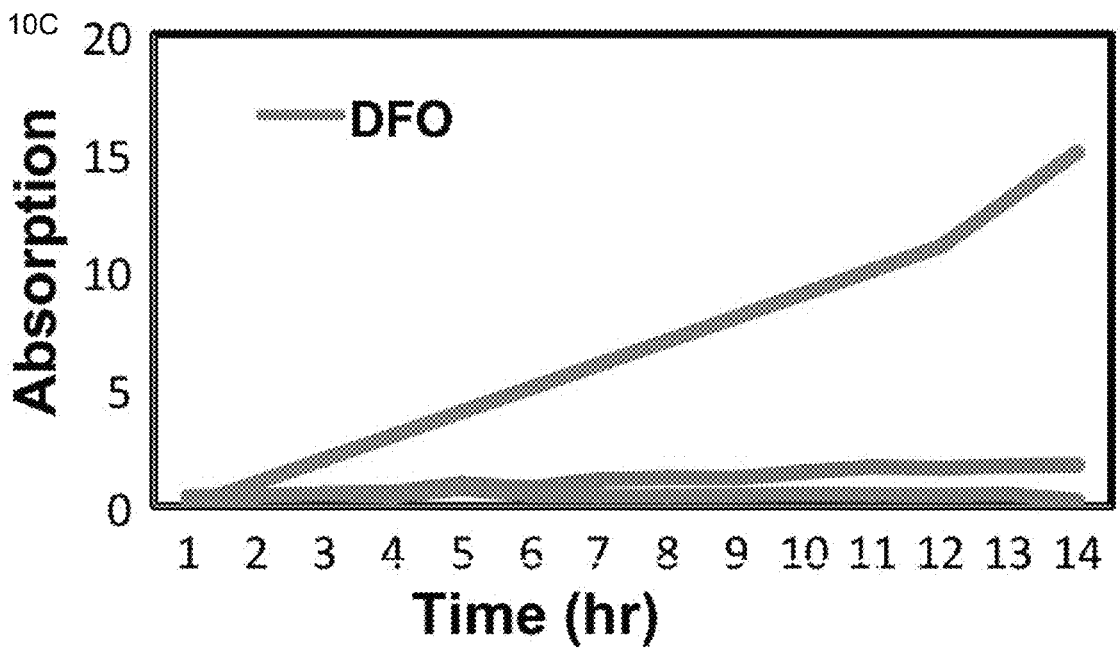

FIG. 17
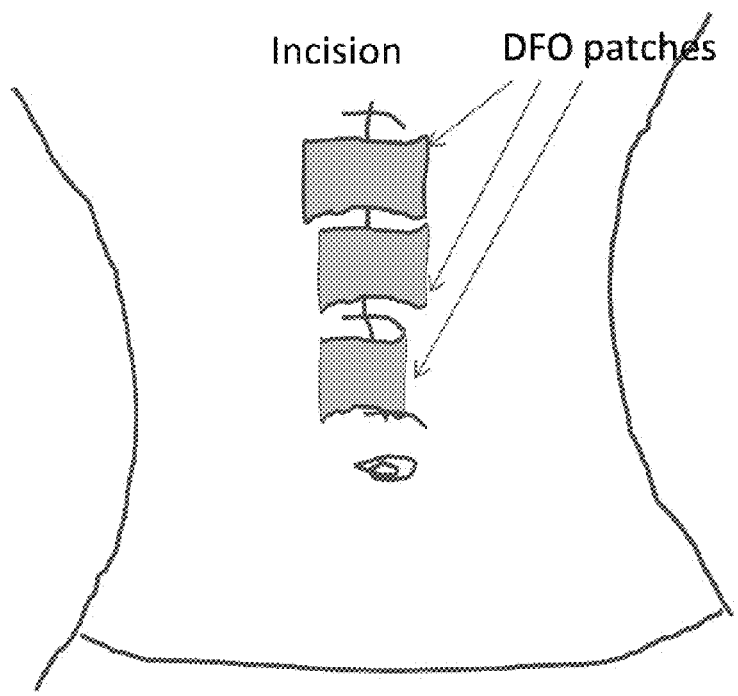
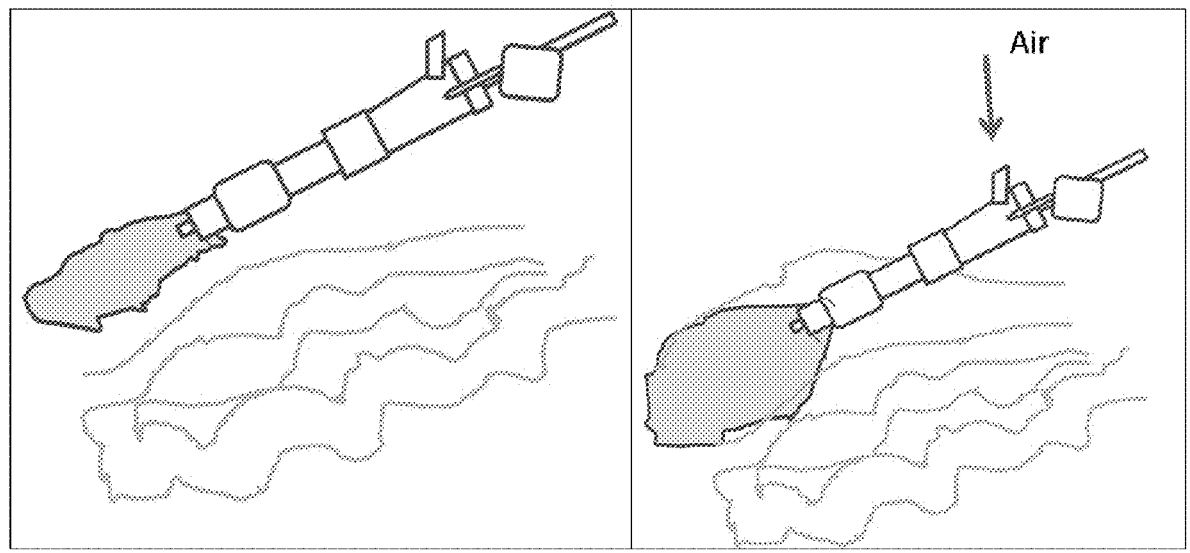
FIG. 18A  FIG. 18B

FIG. 19
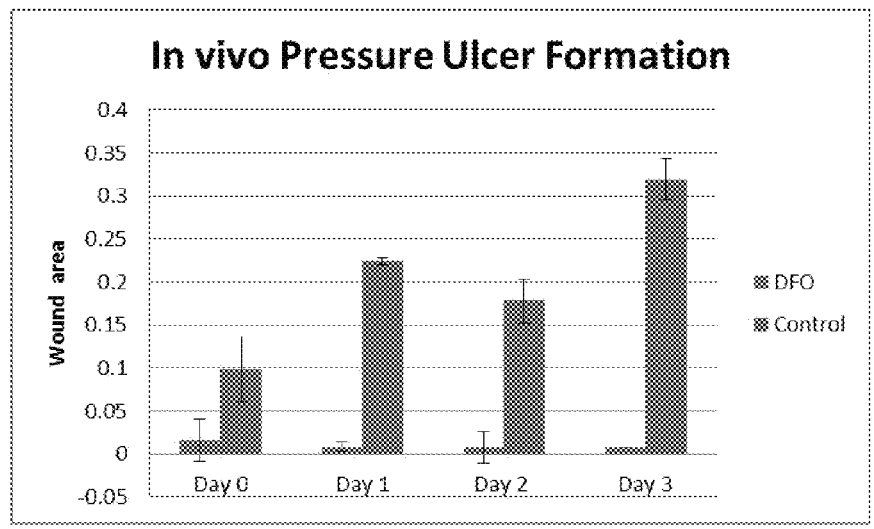
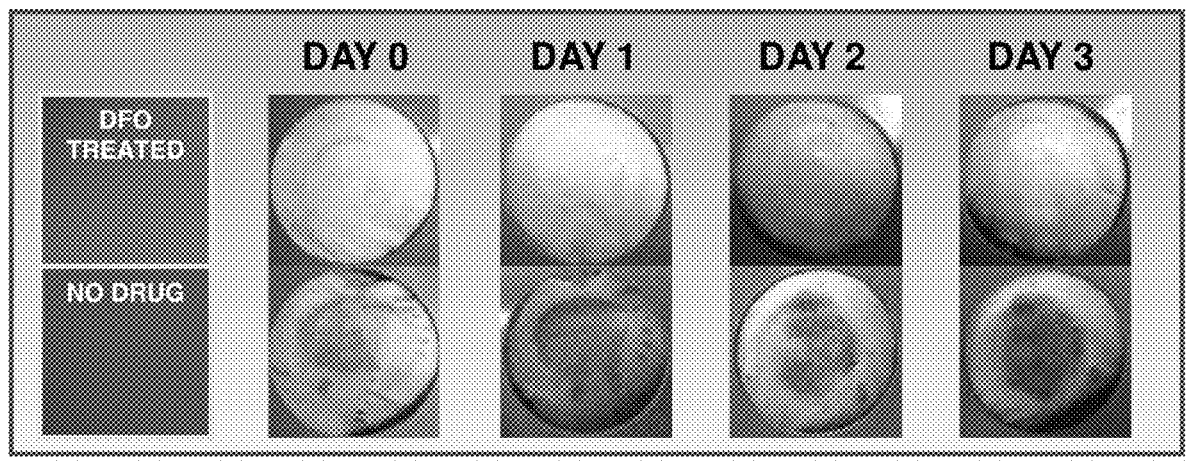

Scale bar = 500 μm

SEM images of the individual needles

FIG. 22B
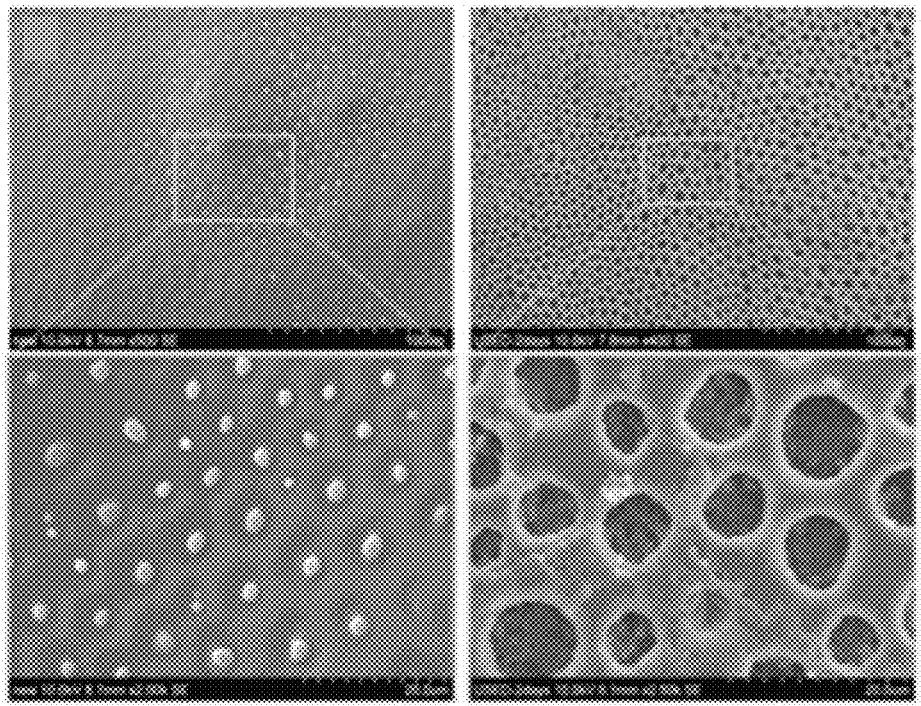
FIG. 22C    FIG. 22D
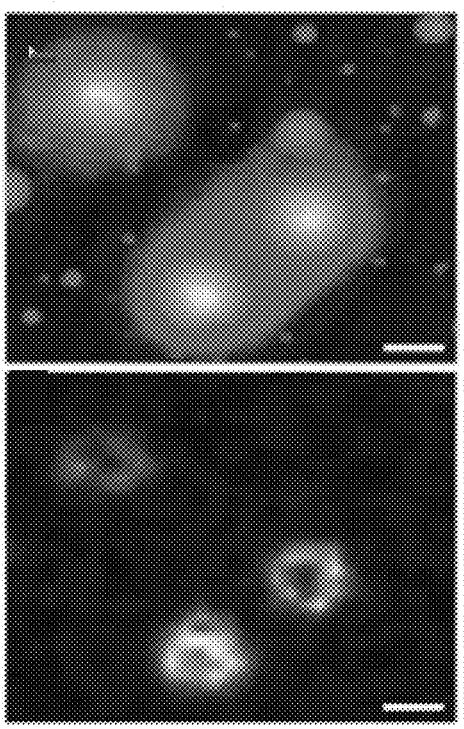 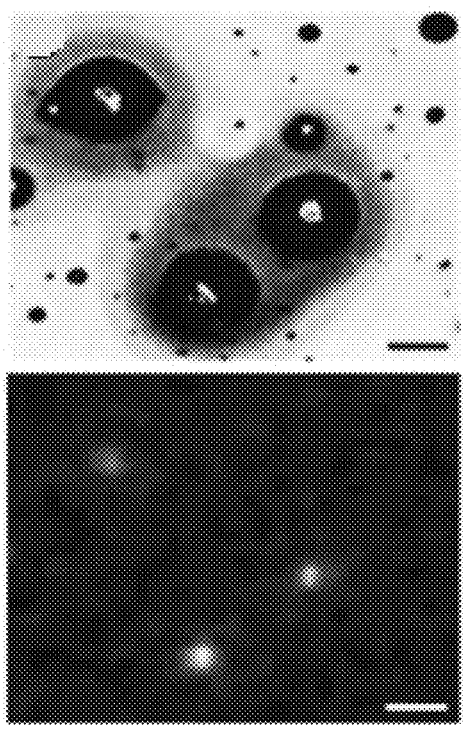
FIG. 22E    FIG. 22F

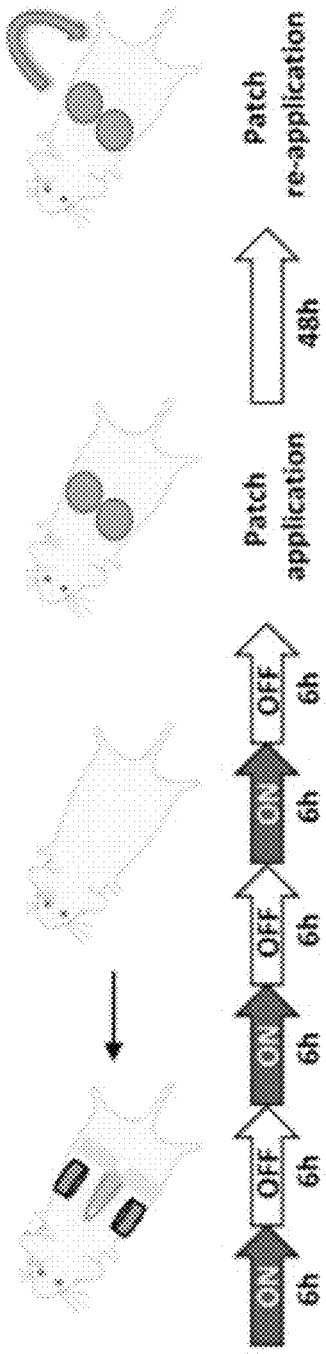
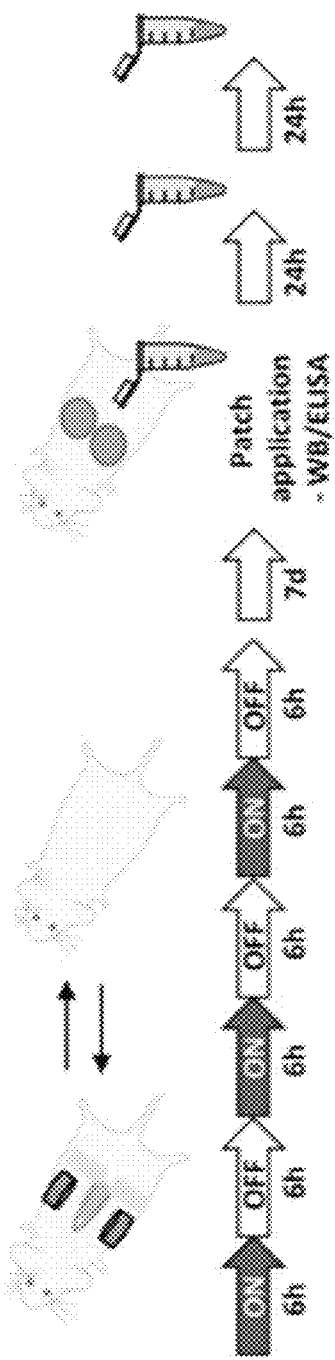
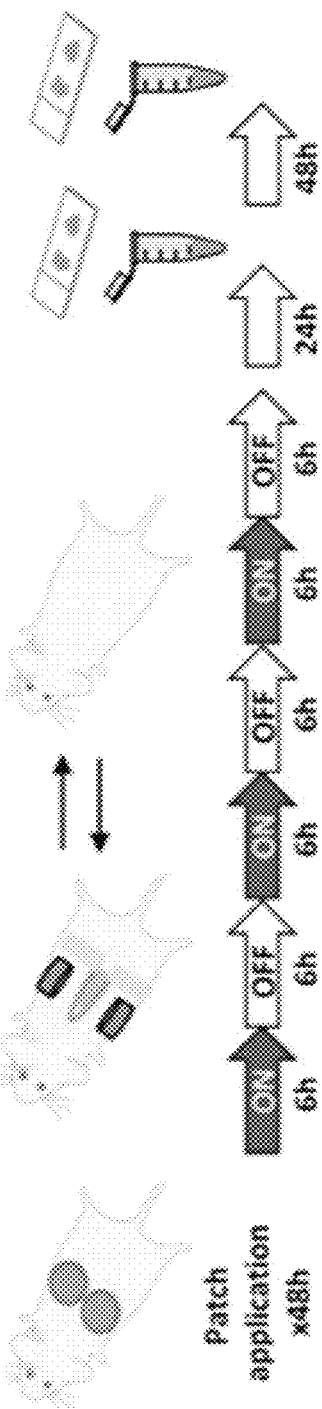
FIG. 26A
FIG. 26B
FIG. 26C

TOPICAL AND TRANSDERMAL DELIVERY OF HIF-1 MODULATORS TO PREVENT AND TREAT CHRONIC WOUNDS

CROSS REFERENCE TO RELATED APPLICATIONS

This application is a continuation of U.S. application Ser. No. 16/127,964, filed Sep. 11, 2018, which claims benefit and is a continuation of U.S. application Ser. No. 15/623,898, filed Jun. 15, 2017, now U.S. Pat. No. 10,098,857, which is a continuation-in-part of U.S. application Ser. No. 14/303,479, filed Jun. 12, 2014, now abandoned, and is a continuation-in-part of U.S. application Ser. No. 12/577,006, filed Oct. 9, 2009, now abandoned, which claims benefit of U.S. Provisional Application No. 61/104,599, filed Oct. 10, 2008. Said U.S. application Ser. No. 14/303,479 claims the benefit of U.S. Provisional Application No. 61/834,336, filed Jun. 12, 2013, which applications are incorporated herein by reference in their entirety.

FEDERALLY SPONSORED RESEARCH AND DEVELOPMENT

This invention was made with Government support under contract AG025016 awarded by the National Institutes of Health. The Government has certain rights in the invention.

BACKGROUND OF THE INVENTION

Nonhealing chronic wounds are a challenge to the patient, the health care professional, and the health care system. They significantly impair the quality of life for millions of people and impart burden on society in terms of lost productivity and health care dollars.

Wound healing is a dynamic pathway that optimally leads to restoration of tissue integrity and function. A chronic wound results when the normal reparative process is interrupted. By understanding the biology of wound healing, the physician can optimize the tissue environment in which the wound is present. Wound healing is the result of the accumulation of processes, including coagulation, inflammation, ground substance and matrix synthesis, angiogenesis, fibroplasia, epithelialization, wound contraction, and remodeling.

In chronic wounds, the process is disrupted, and thus healing is prolonged and incomplete. A chronic wound occurs when some factor causes the disruption of the normal, controlled inflammatory phase or the cellular proliferative phase. Thus, each wound should be evaluated to determine what factors are present and how to correct the problem. Many factors can contribute to poor wound healing. The most common include local causes such as wound infection; tissue hypoxia; repeated trauma; the presence of debris and necrotic tissue; and systemic causes such as diabetes mellitus, malnutrition, immunodeficiency, and the use of certain medications.

Wound infection, and poor circulation are common reasons for poor wound healing. Tissue perfusion may be impaired by arterial occlusion or vasoconstriction, hypotension, hypothermia, and peripheral venous congestion. Reduced wound oxygen tension can delay wound healing by slowing the production of collagen. Wound hypoxia also predisposes to bacterial infection.

Underlying systemic disease in a patient with a wound can increase the probability that the wound will become chronic. Diabetes mellitus is one example. Wound healing is often delayed because of interruption of the inflammatory and proliferative phases. Neutrophils and macrophages cannot adequately keep the bacterial load of the wound controlled, and infection prolongs the inflammatory phase. Erythrocytes can be affected by glycosylation, leading to microvascular sludging and ischemia. Low tissue oxygen tension impairs cellular proliferation and collagen synthesis.

Because chronic wounds have decreased levels of several growth factors, these have been a focus to enhance the repair of the wounds. Topically applied PDGF, TGF-β, and platelet-derived wound healing factor have been utilized in clinical trials to speed the healing of chronic wounds, and PDGF (Regranex) approved for use in the acceleration of wound closure.

Among chronic wounds are included ulcers. Ulcers are exposed surface lesions of the skin or a mucoid layer such as the lining of the mouth, where inflamed and necrotic tissue sloughs off. This exposed tissue is also highly susceptible to opportunistic microbial invasion. Infected ulcers are discomforting to the patient, disfiguring and also life-threatening if leading to a systemic infection.

Common chronic skin and soft tissue wounds include diabetic foot ulcers, pressure ulcers, and venous stasis ulcers. Diabetic ulcers are a common cause of foot and leg amputation. In patients with type I and type II diabetes, the incidence rate of developing foot ulcers is approximately 2% per year. The diabetic foot ulcer is mainly neuropathic in origin, with secondary pathogenesis being a blunted leukocyte response to bacteria and local ischemia due to vascular disease. These wounds usually occur on weight-bearing areas of the foot. Because diabetic ulcers are prone to infection, topical antimicrobials may be used if infection is present, although systemic antibiotics can eventually inhibit fibroblast and keratinocyte proliferation.

Pressure ulcers are the result of prolonged, unrelieved pressure over a bony prominence that leads to ischemia. The wound tends to occur in patients who are unable to reposition themselves to off-load weight, such as paralyzed, unconscious, or severely debilitated persons. Treatment consists of pressure relief, surgical and enzymatic debridement, moist wound care, and control of the bacterial load. Topical applications of antimicrobials and PDGF may be used.

More than 1.6 million pressure ulcers develop in the United States annually, and monetary costs are projected to reach $3.6 billion, not accounting for the impact on patient's family and quality of life. Currently, there are no options for preventing pressure ulcers and few options for improving chronic wound healing in a clinical setting. The present invention addresses this need.

SUMMARY OF THE INVENTION

Compositions and methods are provided for the treatment of chronic wounds, including, without limitation, pressure ulcers and diabetic ulcers, by transdermal delivery of an agent that increases activity of HIF-1α in the wound. Agents that increase HIF-1α activity include, without limitation, agents that stabilize HIF-1α, e.g., deferoxamine, deferiprone, deferasirox, etc.; agents that upregulate expression of HIF-1α, e.g., dimethyloxalylglycine, etc., HIF-1α polypeptide or coding sequences; and combinations thereof. Such agents may be referred to herein as HIF-1α potentiating agents.

In some embodiments, a transdermal patch is provided, where the patch comprises a dose of a HIF-1α potentiating agent effective to increase activity of HIF-1α in the wound, and to improve wound healing or prevent development of a chronic wound. Transdermal patches may also include components such as an adhesive layer, impermeable backing membrane, release liner, transdermal delivery enhancing agents, and the like.

In some embodiments the patch comprises a poloxamer gel, or polymer matrix of polyvinylpyrrolidone (PVP) and ethylcellulose, in which the active agent is entrapped. In some such embodiments, the agent is encapsulated in a reverse micelle with a nonionic surfactant, which reverse micelle is stabilized by, for example, PVP in the matrix. In some embodiments, the components of the film, e.g., agent, PVP, ethylcellulose and nonionic surfactant, are mixed in a lower alcohol, e.g., ethanol, then dried on a hydrophobic surface to form a film, which film can be adhered to a suitable backing.

In other embodiments, a lotion or gel is provided comprising a dose of a HIF-1α potentiating agent effective to increase activity of HIF-1α in the wound, and to improve wound healing. Such lotions or gels may further include components such as excipients, transdermal delivery enhancing agents, and the like.

In other embodiments, a method for improved healing of chronic wounds, or prevention of chronic wounds, is provided, the method comprising transdermal contact of a surgical or injury site, or chronic wound on an individual, with an effective dose of a HIF-1α potentiating agent, for example with a transdermal patch, lotion, gel, and the like. Methods of enhancing transdermal drug may be utilized in combination with the therapeutic composition, including, without limitation, iontophoretic and electroporation methods (applying micro-electric potential to the skin), the application of ultrasound to drive HIF potentiators into the skin, application of magnetic field as a permeation enhancer, microneedles and mechanical devices to give positive pressure, and also the use of a nano-fabricated patch with different gradients of drug loading.

In some embodiments, compositions and methods are provided for the prevention of chronic wounds, by prophylactic transdermal delivery of an agent that increases activity of HIF-1α at the site of a wound, for example following surgery. The site of the wound is contacted with a transdermal that provides for targeted release of a HIF-1α potentiating agent, including without limitation DFO. In some cases the patch can be directly applied, for example by a medical professional. In other embodiments a catheter balloon is used to apply one or more patches to the surface being treated.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1C. HIF Modulators significantly prevent pressure ulcers and increase wound healing. FIG. 1A In a decubitus ulcer model, deferoxamine (DFO) significantly decreases ulcer formation (ulcer grade) compared to controls. FIG. 1B Ulcer incidence in deferoxamine treated pressure ulcer model is significantly decreased (33%) compared to controls (100%) [n=6]. FIG. 1C Deferoxamine treated ulcers have earlier closure date (day 17) and smaller ulcer area compared to controls (day 19) [n=6].

FIG. 2A-2C. Transdermal delivery of HIF-1 modulators increases HIF-1 alpha and neovascularization cytokines. FIG. 2A Increased concentrations of deferoxamine (0.1 mM to 10 mM) result in increased HIF-1 alpha stabilization compared to controls via western blot. FIG. 2B Patch for transdermal delivery, including an impermeable backing, release liner containing HIF-1 alpha modulator, and adhesive. FIG. 2C Deferoxamine significantly increases VEGF (200 ng/ml) compared to control (100 ng/ml) via ELISA.

FIG. 3A-3C. Transdermal HIF stabilization significantly decreases reactive oxygen species, improves vascularization, and decreases cell death. FIG. 3A Superoxide staining (Dihydroethidium) is significantly increased in control ulcers compared to deferoxamine treated ulcers. FIG. 3B Vessel counts (CD31 positive staining) is significantly increased in deferoxamine treated ulcers compared to controls. FIG. 3C TUNEL staining (apoptotic cells) is significantly decreased in deferoxamine treated ulcers compared to controls.

FIG. 4. HIF Modulators improve wound healing in aged animals comparable to young controls. In an established wound healing model, deferoxamine significantly improves wound healing in aged animals (day 15 closure) compared to delivery control (day 21 closure).

FIG. 5A-5B. HIF Modulators significantly improve wound healing and neovascularization in diabetes. FIG. 5A In an established wound healing model, deferoxamine significantly improves wound healing in diabetic (Db/Db, day 13 closure) compared to delivery control (day 23 closure). FIG. 5B CD31 vessel density is significantly increased in diabetic wounds treated with deferoxamine (1000 mM) compared to delivery controls (PBS).

FIG. 6A-6B. Transdermal delivery of HIF modulators increases HIF-1 alpha levels. FIG. 6A Patch for transdermal delivery, including an impermeable backing, release liner containing HIF-1 alpha modulator, and adhesive. FIG. 6B Deferoxamine significantly increases HIF-1 alpha, via western blot, compared to delivery control.

FIG. 7A-7C. Topical and Transdermal delivery of HIF modulators significantly improves diabetic wound and ulcer healing. FIG. 7A Wound closure in aged animals is significantly increased with deferoxamine treatment (Day 14 closure) compared to controls. FIG. 7B Wound closure is significantly increased in diabetic animals in a dose dependent manner with deferoxamine treatment. FIG. 7C Transdermal patch delivery of deferoxamine significantly increases diabetic ulcer closure (Day 30) compared to controls (Day 45+).

FIG. 8A-8E. FIG. 8A Pressure ulcer model schematic. FIG. 8B Highgrade ulcers develop in untreated (PBS) mice. FIG. 8C Reduced incidence of ulcers in DFO group. FIG. 8D Increased vessel count (CD31+) and FIG. 8E reduced apoptosis (TUNEL) in treated mice.

FIG. 9A-9B. FIG. 9A DFO patch on unwounded mouse skin results in HIF-1α stabilization. FIG. 9B Patch applied to wounded skin increased HIF-1α stabilization at day 2.

FIG. 10A-10C. Scanning micrographs of films before FIG. 10A and after FIG. 10B DFO release. Spectrophotometric analysis of DFO absorption in murine skin FIG. 10C.

FIG. 12A-12C show control treatment for Day 1, with DAPI staining FIG. 12A, DHE staining FIG.

12B and visual FIG. 12C. FIG. 12D-12F show a similar set of images for DFO treatment at day 1. FIG. 12G-12I show a similar set of images for control day 3; and FIG. 12J-12L for DFO treatment at Day 3.

FIG. 17. DFO patches applied directly to an incisional wound.

FIG. 18A-18B. FIG. 18A DFO Patch containing balloon. FIG. 18B DFO Patch is deposited into the wound bed.

FIG. 19. Preclinical demonstration of prophylaxis.

FIG. 20A Formulation 7, FIG. 20B Formulation 8, FIG. 20C Formulation 9, and FIG. 20D Formulation 10.

FIG. 22A-22I. Development of a transdermal drug delivery system for DFO. FIG. 22A DFO aggregates with PVP and surfactants to form reverse micelles (RM). RMs are dispersed in the polymer ethyl cellulose. Upon dissolution of ethyl cellulose the RMs enter the stratum corneum and disintegrate. PVP dissolves and DFO is delivered to the dermis. FIG. 22B Scanning electron microscopy (SEM) images of the TDDS at time zero (left panels) and 48 hours post skin application (right panels). Porous structure remains within the polymer after the drug is released to murine skin (right panels). Scale bar=100 and 20 µm. FIG. 22C Atomic force microscopy (AFM) showing the topography of formed RM. FIG. 22D AFM phase imaging demonstrating DFO particles inside the RM. FIG. 22E Raman spectroscopy showing the lipid shell of the RM. FIG. 22F Raman imaging specific for DFO. Scale bar=2 µm FIG. 22G DFO TDDS delivery demonstrated a sustained linear drug release in vitro. Representative result out of 3 experiments. FIG. 22H In vitro penetration profile showing the concentration and location of DFO in full thickness human skin after 24 hour TDDS application. FIG. 22I Application of different TDDS formulations on the intact skin of diabetic mice revealed an increase in HIF-1α stabilization in a dose dependent manner ($*p<0.05$, n=3).

FIG. 23A Full-thickness ulcer wounds of diabetic mice treated with a transdermal DFO TDDS formulation or vehicle control (n=10). TDDS were replaced every 48 hrs. FIG. 23B Wound healing kinetics (wound area as a function of time). Wound closure occurred significantly faster at day 27 in the DFO-treated group versus day 39 in the vehicle treated controls ($p<0.01$, n=10). FIG. 23C Western blot of HIF-1α after transdermal DFO treatment for 1 day and 2 days respectively. ($*p<0.05$, n=3). FIG. 23D Evaluation of HIF-1α levels in skin directly underneath the TDDS, adjacent to it, and 5 mm distant. ($*p<0.01$, n=3). FIG. 23E VEGF protein levels in ulcers of diabetic mice following application of the DFO TDDS ($*p<0.01$, n=3). FIG. 23F Upon complete healing, immunohistochemistry was performed for the capillary endothelial cell marker CD31 (red). Increased vascularity was seen in transdermal DFO-treated diabetic mice. Scale bar=10 µm. blue=DAPI FIG. 23G Quantification of CD31-positive pixels per HPF ($*p<0.01$, n=10). FIG. 23H Dermal thickness of completely healed wounds was assessed by polarized light microscopy after picrosirius red staining. Scale bar=10 µm. FIG. 23I Quantification of picrosirius red positive pixels per HPF. ($*p<0.01$, n=10).

FIG. 24A Representative photographs of skin after ulcer induction in diabetic mice pre-treated with either DFO or control TDDS. No severe ulcer formation in the DFO treated group. FIG. 24B Quantification of control and DFO treated necrotic area ($*p<0.01$, n=10). FIG. 24C Representative histological H&E stained tissue sections showing ulcer formation in the vehicle control group. Scale bar=10 µm. n=10 FIG. 24D Western blot analysis of Cleaved Caspase-3 (Cl Casp.3) and Bax proteins via Western blot. DFO pre-treated mice show a significant reduction of both apoptotic markers. (FIG. 24E, FIG. 24F) Quantification of Western Blot ($*p<0.01$, n=3). FIG. 24G DHE immunofluorescent stain for oxidative stress reveals decreased ROS accumulation (red) in DFO treated wounds.

(FIG. 25A, FIG. 25B) Pressure induced ulcer model. Constant pressure is applied to the skin by two ceramic magnets. FIG. 25C 6 h ischemic-reperfusion cycles induced more uniform skin ulcers with closure at day 35. FIG. 25D Pressure ulcer wound kinetics after 3 h and 6 h ischemic-reperfusion cycles. n=5.

FIG. 26A-26C. Pressure induced ulcer model protocols. FIG. 26A For the wound healing experiment ulcers were induced applying 3 cycles of ischemia/reperfusion 6 hours each followed by TDDS application 24 after the last cycle. TDDS was replaced every 48 hours until complete ulcer healing. FIG. 26B For protein detection TDDS were applied 7 days after ulcer induction. Protein analysis took place 24 and 48 hours after transdermal treatment. FIG. 26C For assessment of the efficacy of the TDDS for ulcer prophylaxis mice were pre-treated for 48 hours prior ulcer induction. Resulting wound development was monitored and histology and protein analysis took place 24 and 72 hours after ulcer induction.

DETAILED DESCRIPTION OF THE EMBODIMENTS

Figure 11:
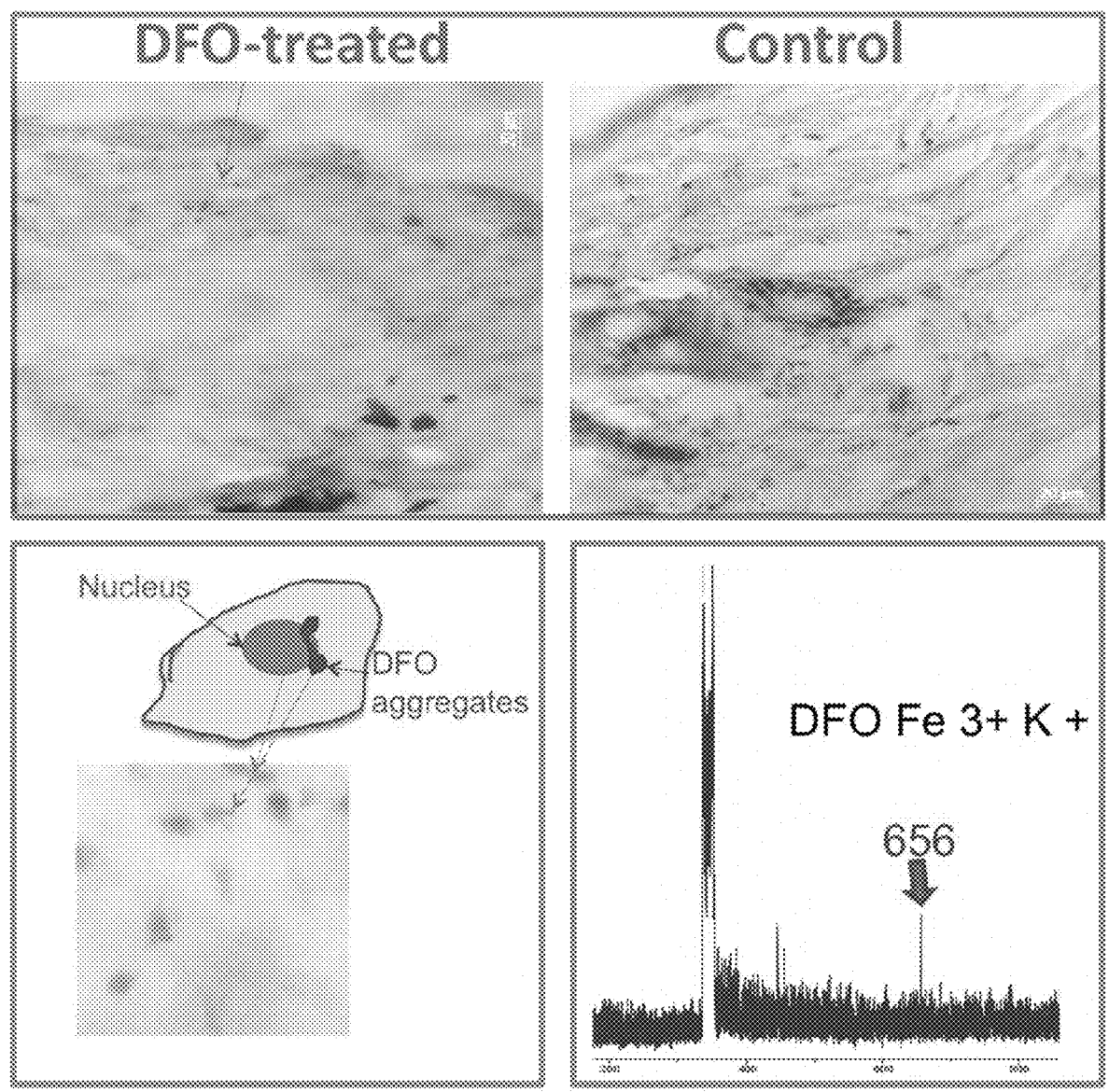
FIG. 11. Potassium ferrocyanide staining identifies DFO iron aggregates in treated human cadaveric skin (top, left). MALDI-TOF imaging detects DFO iron complex (bottom-right).

The transcription factor HIF-1α is critical for new vessel formation, or neovascularization, during wound healing and has been found to be markedly impaired in chronic wounds. HIF-1α modulators are small molecules with the ability to increase HIF-1α activity, resulting in the increase of vasculogenic growth factors. By increasing neovascularization, a process central to wound healing, it is shown herein that targeted transdermal delivery of HIF-1α potentiators, e.g., through topical gels, lotions, etc. and transdermal patches can prevent and treat of chronic wounds, including ulcers such as diabetic ulcers, pressure ulcers, venous stasis ulcers, etc. Targeting the HIF-1α regulated neovascularization cascade reverses the impairments seen with aging and chronic wounds.

HIF-1α potentiators for use in the methods of the invention include small molecules that increase HIF-1α stability, such as deferoxamine and dimethyloxalylglycine. Other agents of interest increase HIF-1α activity by upregulating expression of HIF-1α, by directly providing HIF-1α activity, etc. These HIF-1 potentiators can treat and more importantly prevent a broad range of acute and chronic skin wounds in humans.

In some embodiments of the invention, the HIF1α potentiator is a hydrophilic agent, for example, deferoxamine (DFO). The hydrophilicity presents a challenge in formulation, particularly for transdermal administration. This problem is addressed in the present invention by generating a film in which the hydrophilic agent is encapsulated in a reverse micelle with a nonionic surfactant, which reverse micelle is stabilized by PVP in an ethylcellulose matrix. Surfactants of interest include, without limitation, TWEEN 85® (Polyoxyethylene (20) Sorbitan Trioleate); phospholipids such as Plurol Oleique®; TRITON X-100® (Octylphenol ethylene oxide condensate); AOT (dioctyl sulfosuccinate)-TWEEN 80® (Polysorbate 80); AOT-DOLPA (dioleyl phosphoric acid); AOT-OPE4 (p,t-octylphenoxyethoxyethanol); CTAB (cetyl trimethylammonium bromide)-TRPO (mixed trialkyl phosphine oxides); lecithin; and CTAB. Conveniently, the reverse micelle structure can be generated by dissolving the film components, e.g., hydrophilic agent, PVP, ethylcellulose and surfactant in a lower alcohol, e.g., ethanol, then drying on a hydrophobic surface to form a film, which can be adhered to a suitable backing for use in the methods of the invention.

Compositions and methods are provided for the treatment of chronic wounds, including, without limitation, pressure ulcers and diabetic ulcers, by transdermal delivery of an agent that increases activity of HIF-1α in the wound. Transdermal delivery vehicles include gels, lotions, patches, etc., formulated for topical delivery.

Definitions

The terms "treating", and "treatment" and the like are used herein to generally mean obtaining a desired pharmacological and/or physiological effect. The effect may be prophylactic in terms of preventing or partially preventing a disease, symptom or condition thereof and/or may be therapeutic in terms of a partial or complete cure of a disease, condition, symptom or adverse effect attributed to the disease, i.e., infection. The term "treatment" as used herein covers any treatment of a wound in a mammal, particularly a human, and includes: preventing a wound in an individual from dysfunction in initial healing; treating a wound that has reached a chronic state; or relieving chronic wound symptoms by mitigating or ameliorating the symptoms or conditions. The term "prophylaxis" are used herein to refer to a measure or measures taken for the prevention or partial prevention of a disease or condition.

The term "subject" includes mammals, e.g., cats, dogs, horses, pigs, cows, sheep, rodents, rabbits, squirrels, bears, primates such as chimpanzees, gorillas, and humans which may suffer from chronic wounds, particularly chronic skin ulcers. The term "subject" also comprises elderly individuals, diabetic individuals, etc., who may be at a higher risk for chronic wounds.

The term "wound management" refers to therapeutic methods that induce and/or promote repair of a wound including, but not limited to, arresting tissue damage such as necrotization, promoting tissue growth and repair, reduction or elimination of an established microbial infection of the wound and prevention of new or additional microbial infection or colonization. The term may further include reducing or eliminating the sensation of pain attributable to a wound.

Pressure ulcers are areas of necrosis and ulceration where tissues are compressed between bony prominences and hard surfaces; they may also develop from friction and shearing forces. Risk factors include old age, impaired circulation, immobilization, malnourishment, and incontinence. Severity ranges from skin erythema to full-thickness skin loss with extensive soft-tissue necrosis. Diagnosis is clinical. Conventional treatment includes pressure reduction, avoidance of friction and shearing forces, local care, and sometimes skin grafts or myocutaneous flaps. Prognosis is excellent for early-stage ulcers; neglected and late-stage ulcers pose risk of serious infection and nutritional stress and are difficult to heal.

An estimated 1.3 to 3 million patients in the US have pressure ulcers (PUs); incidence is highest in older patients, especially when hospitalized or in long-term care facilities. Aging increases risk, in part because of reduced subcutaneous fat and decreased capillary blood flow. Immobility and comorbidities increase risk further.

Other causes of skin ulcers: Chronic arterial and venous insufficiency, e.g., associated with diabetes, can result in skin ulcers, particularly on the lower extremities. Although the underlying mechanism is vascular, the same forces that cause PUs can worsen these ulcers, and principles of treatment are similar.

Several staging systems exist; the most common classifies ulcers based on the depth of soft-tissue damage. Stage 1 ulcers manifest hyperemia, warmth, and induration. This stage is a misnomer in the sense that an ulcer (a defect of skin into the dermis) is not present. However, ulceration will form if the course is not arrested and reversed. Stage 2 ulcers involve erosion (defect of epidermis) or true ulceration; however, subcutaneous tissue is not exposed. Stage 3 and 4 ulcers have deeper involvement of underlying tissue with more extensive destruction. Patients do not always progress from lower to higher stages. Sometimes the first sign is a deep, necrotic Stage 3 or 4 ulcer. When ulcers develop quickly, subcutaneous tissue can become necrotic before the epidermis erodes. Any small ulcer should be thought of as an iceberg, with a potentially deep base.

The methods of the invention may improve the score of a skin ulcer by at least one stage, e.g., from a stage 3 or 4, to a stage 1 or 2, and may provide an improvement to where the wound is fully healed. The time required for such healing is less than the time required for healing in the absence of the treatment methods of the invention, e.g., a wound may be healed in less than about 4 weeks, less than about 3 weeks, less than about 2 weeks, or less.

Hypoxia-inducible factor (HIF-1) is an oxygen-dependent transcriptional activator, which plays crucial roles in the angiogenesis of tumors and mammalian development. HIF-1 consists of a constitutively expressed HIF-1β subunit and one of three subunits (HIF-1α, HIF-2α or HIF-3α). The stability and activity of HIF-1α are regulated by various post-translational modifications, hydroxylation, acetylation, and phosphorylation. Under normoxia, the HIF-1α subunit is rapidly degraded via the von Hippel-Lindau tumor suppressor gene product (vHL)-mediated ubiquitin-proteasome pathway. The association of vHL and HIF-1α under normoxic conditions is triggered by the hydroxylation of prolines and the acetylation of lysine within a polypeptide segment known as the oxygen-dependent degradation (ODD) domain. During hypoxic conditions HIF-1α subunit becomes stable and interacts with coactivators such as p300/CBP to modulate its transcriptional activity.

HIF-1 acts as a master regulator of numerous hypoxia-inducible genes under hypoxic conditions. The heterodimer HIF-1 binds to the hypoxic response elements (HREs) of target gene regulatory sequences, resulting in the transcription of genes implicated in the control of cell proliferation/survival, glucose/iron metabolism and angiogenesis, as well as apoptosis and cellular stress. Some of these direct target genes include glucose transporters, the glycolytic enzymes, erythropoietin, and angiogenic factor vascular endothelial growth factor (VEGF).

The term "HIF-1", as used herein, includes both the heterodimer complex and the subunits thereof, HIF-1α and HIF-1. The HIF 1 heterodimer consists of two helix-loop-helix proteins; these are termed HIF-1α, which is the oxygen-responsive component (see, e.g., Genbank accession no. Q16665), and HIF-1β. The latter is also known as the aryl hydrocarbon receptor nuclear translocator (ARNT). Preferably, the term refers to the human form of HIF-1α (see, e.g., Genbank Accession No. NM001530).

HIF-1α may refer to any mammalian or non-mammalian protein or fragment thereof. HIF-1α gene sequences may also be obtained by routine cloning techniques, for example by using all or part of a HIF-1α gene sequence described above as a probe to recover and determine the sequence of a HIF-1α gene in another species. A fragment of HIF-1α of interest is any fragment retaining at least one functional or structural characteristic of HIF-1α.

The term "pharmaceutically acceptable" as used herein refers to a compound or combination of compounds that will not impair the physiology of the recipient human or animal to the extent that the viability of the recipient is compromised. Preferably, the administered compound or combination of compounds will elicit, at most, a temporary detrimental effect on the health of the recipient human or animal.

The term "carrier" as used herein refers to any pharmaceutically acceptable solvent of agents that will allow a therapeutic composition to be administered directly to a wound of the skin. The carrier will also allow a composition to be applied to a medical dressing for application to such a wound. A "carrier" as used herein, therefore, refers to such solvent as, but not limited to, water, saline, physiological saline, ointments, creams, oil-water emulsions, gels, or any other solvent or combination of solvents and compounds known to one of skill in the art that is pharmaceutically and physiologically acceptable to the recipient human or animal.

HIF-1α potentiating agents include agents that increase the accumulation of, or stability of, HIF-1α; directly provide HIF-1α activity; or increase expression of HIF-1. Such agents are known in the art, or may be identified through art-recognized screening methods.

A number of proteins are known to induce HIF-1α protein translation irrespective of hypoxia, including certain growth factors (see, e.g., Lee et al., Exp Mol Med 36(1):1-12 (2004), including the EBV latent membrane protein 1 (LMP1) (Wakisaka et al., Mol Cell Biol 24(12):5223-34 (2004)), and the like.

Ligands to HIF-1 form a further aspect of the invention. Agonist ligands include those that bind to the polypeptide HIF-1 or HIF-1 interacting proteins and strongly induce activity of the polypeptide and/or increases or maintain substantially the level of the polypeptide in the cell, e.g., by binding to and activating HIF-1, by binding to a nucleic acid target with which the transcription factor interacts, by facilitating or disrupting a signal transduction pathway responsible for activation of a particular regulon, and/or by facilitating or disrupting a critical protein-protein interaction.

Of particular interest are compounds currently identified as HIF-1 potentiating agents. Examples of suitable compounds include cofactor-based inhibitors such as 2-oxoglutarate analogues, ascorbic acid analogues and iron chelators such as desferrioxamine (DFO), the hypoxia mimetic cobalt chloride ($CoCl_2$), and mimosine, 3-Hydroxy-4-oxo-1(4H)-pyridinealanine, or other factors that may mimic hypoxia. Also of interest are hydroxylase inhibitors, including deferiprone, 2,2'-dipyridyl, ciclopirox, dimethyloxallyl glycine (DMOG), L-Mimosine (Mim) and 3-Hydroxy-1,2-dimethyl-4(1H)-Pyridone (OH-pyridone). Other HIF hydroxylase inhibitors are described herein, including but not limited to, oxoglutarates, heterocyclic carboxamides, phenanthrolines, hydroxamates, and heterocyclic carbonyl glycines (including, but not limited to, pyridine carboxamides, quinoline carboxamides, isoquinoline carboxamides, cinnoline carboxamides, beta-carboline carboxamides, including substituted quinoline-2-carboxamides and esters thereof; substituted isoquinoline-3-carboxamides and N-substituted arylsulfonylamino hydroxamic acids (see, e.g., PCT Application No. WO 05/007192, WO 03/049686 and WO 03/053997), and the like.

Compounds reported to stabilize HIF-1α also include [(3-hydroxy-6-isopropoxy-quinoline-2-carbonyl)-amino]-acetic acid, [3-hydroxy-pyridine-2-carbonyl)-amino]-acetic acid, [N-((1-chloro-4-hydroxy-isoquinoline-3-carbonyl)-amino)-acetic acid, [(7-bromo-4-hydroxy-isoquinoline-3-carbonyl)-amino]-acetic acid, [(7-chloro-3-hydroxy-quinoline-2-carbonyl)-amino]-acetic acid, [(1-bromo-4-hydroxy-7-kifluoromethyl-isoquinoline-3-carbonyl)-amino]-acet-ic acid, [(1-Bromo-4-hydroxy-7-phenoxy-isoquinoline-3-carbonyl)-amino]-ace-tic acid, [(1-Chloro-4-hydroxy-7-phenoxy-isoquinoline-3-carbonyl)-amino]-acetic acid, [(1-Chloro-4-hydroxy-7-methoxy-isoquinoline-3-carbonyl)-amino]-acetic acid, [(1-chloro-4-hydroxy-isoquinoline-3-carbonyl)-amino]-acetic acid, [(4-Hydroxy-7-phenoxy-isoquinoline-3-carbonyl)-amino]-acetic acid, [(4-Hydroxy-7-phenylsulfanyl isoquinoline-3-carbonyl)-amino]-acetic acid, [(4-Hydroxy-6-phenylsulfanyl-isoquinoline-3-carbonyl)-amino]-acetic acid, 4-oxo-1,4-dihydro-[1,10]phenanthroline-3-carboxylic acid, 4-hydroxy-5-methoxy-[1,10]phenanthroline-3-carboxylic acid ethyl ester, [(7-benzyloxy-1-chloro-4-hydroxy-isoquinoline-3-carbonyl)-amino]-acetic acid methyl ester, and 3-{[4-(3,3-Dibenzyl-ureido)-benzenesulfonyl]-[2-(4-methoxy-phenyl)-ethyl]-amino}-N-hydroxy-propionamide.

The HIF-1α potentiating agent or agents is formulated for dosing, typically embedded or dispersed in a polymer, as described here. The effective dose will be determined by the selection of agent, length of time where the polymer is a biodegradable polymer intended for extended release of the drug. In general, the HIF-1α potentiating agent will be present at a concentration of at least about 1%, about 2%, about 3%, about 5% about 7.5% and not more than about 20%, not more than about 15%, not more than about 12.5%, and may at about 10%, as weight/weight percent of polymer.

The total dose of HIF-1α potentiating agent provided in a transdermal patch will be at least about 1 mg, usually at least about 5 mg, and not more than about 1000 mg, usually not more than about 500 mg, or not more than about 200 mg, and may be from about 10 mg to about 200 mg, e.g., about 100 mg.

Methods of the Invention

The present invention provides methods for wound management wherein a wound of a human or animal patient, e.g., a chronic skin ulcer, is contacted topically with an effective amount a therapeutic composition comprising a HIF-1α potentiating agent, and a carrier. The composition may be formulated as a patch, lotion, gel, etc., and may further comprise additional agents involved in wound healing, e.g., transdermal penetration enhancers, anti-microbial agents, and the like. Administration of the compositions of the present invention to a wound results in accelerated wound repair with reduced sepsis. Even with chronic ulcers that have penetrated the dermal layer, there is reduced pain sensation, more extensive and quicker tissue growth and less overall discomfort to the patient.

The timing of for administration of a therapeutic composition of the invention, e.g., a transdermal patch, will vary for prophylaxis or treatment. The dosage of HIF modulator can determine the frequency of drug depletion in transdermal patch. For example, the transdermal patch can be applied and changed to a fresh patch every day, every other day, every third day, etc. In general it is desirable to apply a transdermal patch when a chronic wound is detected, e.g., reaches at stage 1 or stage 2, although more advanced stages will find benefit from the methods of the invention as well.

Before applying the therapeutic composition to the patient, the wound can be debrided to clean the wound of necrotic or infected tissue. Debridation may be mechanical by cutting or pulling away damaged tissue from the wound or, if readily inaccessible, other methods including, but not limited to, the application of sterile maggots may be used. Optionally, the wound may be prewashed before the application of the therapeutic composition using a composition comprising a buffering agent, detergent, etc.

The therapeutic compositions of the present invention may additionally include a pharmaceutically acceptable pH buffering agent that preferably will maintain the pH of the composition, when delivered to the skin injury or skin lesion, to between about pH 7.0 and about pH 9.0. A pH buffering agent may be selected from, but is not limited to, Tris (hydroxymethyl) aminomethane (tromethaprim; TRIZMA base), or salts thereof, phosphates or any other buffering agent such as, for example, phosphate-buffered saline that is biologically acceptable. The buffering agent may have an effective dose of between about 5 mM and about 250 mM.

The compositions of the present invention may also comprise at least one antimicrobial agent. The infections that may be treated by the methods and compositions of the present invention may be any opportunistic infection of a wound by a bacterium, or a multiple infection of more than one species of bacteria. Microbial species that may cause infections include *Aerobacter aerongenes, Aeromonas* spp., *Bacillus* spp., *Bordetella* spp, *Campylobacter* spp., *Chlamydia* spp., *Corynebacterium* spp., *Desulfovibrio* spp., *Escherichia coli*, enteropathogenic *E. coli*, Enterotoxin-producing *E. coli*, *Helicobacter pylori*, *Klebsiella pneumoniae*, *Legionella pneumophiia*, *Leptospira* spp., *Mycobacterium tuberculosis*, *M. bovis*, *Neisseria gonorrhoeae*, *N. meningitidis*, *Nocardia* spp., *Proteus mirabilis*, *P. vulgaris*, *Pseudomonas aeruginosa*, *Rhodococcus equi*, *Salmonella enteridis*, *S. typhimurium*, *S. typhosa*, *Shigella sonnei*, *S. dysenterae*, *Staphylococcus aureus*, *Staph. epidermidis*, *Streptococcus anginosus*, *S. mutans*, *Vibrio cholerae*, *Yersinia pestis*, *Y. pseudotuberculosis*, *Actinomycetes* spp., and *Streptomyces* spp.

The action of the antimicrobial agent can be either bacteriostatic wherein the antibiotic arrests the proliferation of, but does not necessarily kill, the microorganism or the activity of the antibiotic can be bacteriocidal and kill the organism or a combination of activities. Antibiotics suitable for use in the wound management methods of the present invention include, but are not limited to, β-lactams (penicillins and cephalosporins), vancomycins, bacitracins, macrolides (erythromycins), lincosamides (clindomycin), chloramphenicols, tetracyclines, aminoglycosides (gentamicins), amphotericns, cefazolins, clindamycins, mupirocins, sulfonamides and trimethoprim, rifampicins, metronidazoles, quinolones, novobiocins, polymixins, tetracyclines, and Gramicidins and the like and any salts or variants thereof.

The therapeutic compositions for use in the methods of wound management may also comprise a surfactant that can useful in cleaning a wound or contributing to bactericidal activity of the administered compositions. Suitable surfactants include, but are not limited to, phospholipids such as lecithin, including soy lecithin and detergents. Preferably, the surfactant selected for application to a wound or skin surface is mild and not lead to extensive irritation or promote further tissue damage to the patient.

Suitable nonionic surfactants which can be used are, for example: fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acylpolyethylene glycols); polypropylene glycol ethoxylates (Pluronic); fatty acid alkylolamides (fatty acid amide polyethylene glycols); alkyl polyglycosides, N-alkyl-, N-alkoxypolyhydroxy fatty acid amide, in particular N-methyl-fatty acid glucamide, sucrose esters; sorbitol esters, and esters of sorbitol polyglycol ethers. A preferred surfactant is polypropylene glycol ethoxylates with a preferred concentration of between about 5% wt % and about 25% wt %, for example Pluronic F-127 (Poloxamer 407). In other embodiments of the composition, the surfactant comprises lecithin with or without the addition of Pluronic F-127, the Pluronic F-127 being between about 2 and about 20 wt % for increasing the viscosity or gelling of the compositions.

The nonionic surfactant can also provide for formation of reverse micelles, which advantageously aid in delivery of the active agent. Suitable surfactants for this purpose include Tween 85, phospholipids, e.g., plural oleique, TX-100, AOT-tween 80, AOT-DOLPA, AOT-OPE4, CTAB-TRPO, lecithin, and CTAB (cetyltrimethylammonium bromide). The surfactant may be present at a concentration of from about 5 wt % to about 25 weight %, about 10 wt % to about 20 wt %, about 12 wt % to about 18 wt %, about 14 wt % to about 17 wt %, about 15 wt %, about 16 wt %, about 17 wt %.

The therapeutic compositions for use in the methods of the invention preferably include a pharmaceutically acceptable carrier that provides the medium in which are dissolved or suspended the constituents of the compositions. Suitable carriers include any aqueous medium, oil, emulsion, ointment and the like that will allow the therapeutic compositions to be delivered to the target wound without increasing damage to the tissues of the wound.

Medical dressings suitable for use in the methods of the present invention for contacting a wound with the therapeutic compositions can be any material that is biologically acceptable and suitable for placing over any chronic wound. In exemplary embodiments, the support may be a woven or non-woven fabric of synthetic or non-synthetic fibers, or any combination thereof. The dressing may also comprise a support, such as a polymer foam, a natural or man-made sponge, a gel or a membrane that may absorb or have disposed thereon, a therapeutic composition. A gel suitable for use as a support for the antimicrobial composition of the present invention is sodium carboxymethylcellulose 7H 4F, i.e. ethylcellulose.

Hydrocolloids (eg, RepliCare, DuoDERM, Restore, Tegasorb), which are combinations of gelatin, pectin, and carboxymethylcellulose in the form of wafers, powders, and pastes, are indicated for light to moderate exudate; some have adhesive backings and others are typically covered with transparent films to ensure adherence to the ulcer and must be changed q 3 days. Alginates (polysaccharide seaweed derivatives containing alginic acid), which come as pads, ropes, and ribbons (AlgiSite, Sorbsan, Curasorb), are indicated for extensive exudate and for control of bleeding after surgical debridement. Foam dressings (Allevyn, LYOfoam, Hydrasorb, Mepilex, Curafoam, Contreet) are useful as they can handle a variety of levels of exudate and provide a moist environment for wound healing. Those with adhesive backings stay in place longer and need less frequent changing.

In some embodiments, the formulation comprises a permeation enhancer, e.g., transcutol, (diethylene glycol monoethyl ether), propylene glycol, dimethylsulfoxide (DMSO), menthol, 1-dodecylazepan-2-one (Azone), 2-nonyl-1,3-dioxolane (SEPA 009), sorbitan monolaurate (Span20), and dodecyl-2-dimethylaminopropanoate (DDAIP), which may be provided at a weight/weight concentration of from about 0.1% to about 10%, usually from about 2.5% to about 7.5%, more usually about 5%.

Transdermal patches may further comprise additives to prevent crystallization. Such additives include, without limitation, one or more additives selected from octyldodecanol at a concentration of from about 1.5 to about 4% w/w of polymer; dextrin derivatives at a concentration of from about 2 to about 5% w/w of polymer; polyethylene glycol (PEG) at a concentration of from about 2 to about 5% w/w of polymer; polypropylene glycol (PPG) at a concentration of from about 2 to about 5% w/w of polymer; mannitol at a concentration of from about 2 to about 4% w/w of polymer; Poloxamer 407, 188, 401 and 402 at a concentration of from about 5 to about 10% w/w of polymer; and Poloxamines 904 and 908 at a concentration of from about 2 to about 6% w/w of polymer.

Polyvinylpyrrolidine (PVP) may also be included in a transdermal patch formulation, for example at a concentration of from about 5 wt % to about 25 weight %, about 7 wt % to about 20 wt %, about 8 wt % to about 18 wt %, about 10 wt % to about 16 wt %, about 10 wt %, about 12 wt %, about 14 wt %, about 16 wt %.

In some embodiments the components of a transdermal patch are combined in ethanol, and dried on a hydrophobic surface to form a film that can be adhered to a support film. Such components usually include a HIF-1α potentiating agent, including without limitation DFO, ethylcellulose at a concentration of from about 25 wt % to about 75 wt %, about 35 wt % to about 65 wt %, about 40 wt % to about 60 wt %, about 45 wt % to about 55 wt %, about 45 wt %, about 48 wt %, about 50 wt %, about 52 wt %, about 54 wt %, about 55 wt %; PVP at a concentration as described above; a nonionic surfactant, e.g., plural oleique or CTAB; and optionally additional agents such acetyl alcohol; etc.

Emulsifiers which may be used include glyceryl stearate, polysorbate 60, PEG-6/PEG-32/glycol stearate mixture, etc. Solvents which may be used include the lower alcohols, in particular ethanol and isopropanol, and propylene glycol.

Hydrophilic gelling agents include carboxyvinyl polymers (carbomer), acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

A patch can be applied for prevention of chronic wounds, e.g., applied at the time of surgery, applied after injury to a person at risk for development of chronic wounds, such as an individual with diabetes, and the like; or can be applied for improved healing of chronic wounds, e.g., by application of the patch to existing chronic wounds. Such methods comprise transdermal contact of a chronic wound or surgical site or injury site on an individual, with an effective dose of a HIF-1α potentiating agent with a transdermal patch of the invention. The patch can be replaced as needed, or allowed to biodegrade in situ.

In some cases the patch can be directly applied, for example by a medical professional. In other embodiments a catheter balloon is used to apply one or more patches to the surface being treated. In such embodiments a patch is applied to the surface of a balloon, which is inserted into the space of a surgical site, and expanded to contact the body tissue with the patch, as shown in FIGS. 17 and 18. When contact has been made, the balloon is deflated and withdrawn.

For example, post-operative application of deferoxamine films and/or patches are made directly to incisional sites, which can be delivered by the methods of the invention in a controlled fashion to sites of interest. The patch formulations are designed to be totally biodegradable, and when applied to superficial wounds facilitate the delivery of a locally concentrated deferoxamine dose during the initial post-operative period. In the case of incisional wounds, a deferoxamine patch is applied to the entire wound cavity by inflating a silicon balloon catheter wrapped with a patterned deferoxamine patch within the defect. The biodegradable properties of the delivery construct are important when applied in this fashion, as they enable the surgical site to be closed normally upon completion of the procedure, while providing a sustained drug delivery during the critical early post-operative period.

Figure 21A:
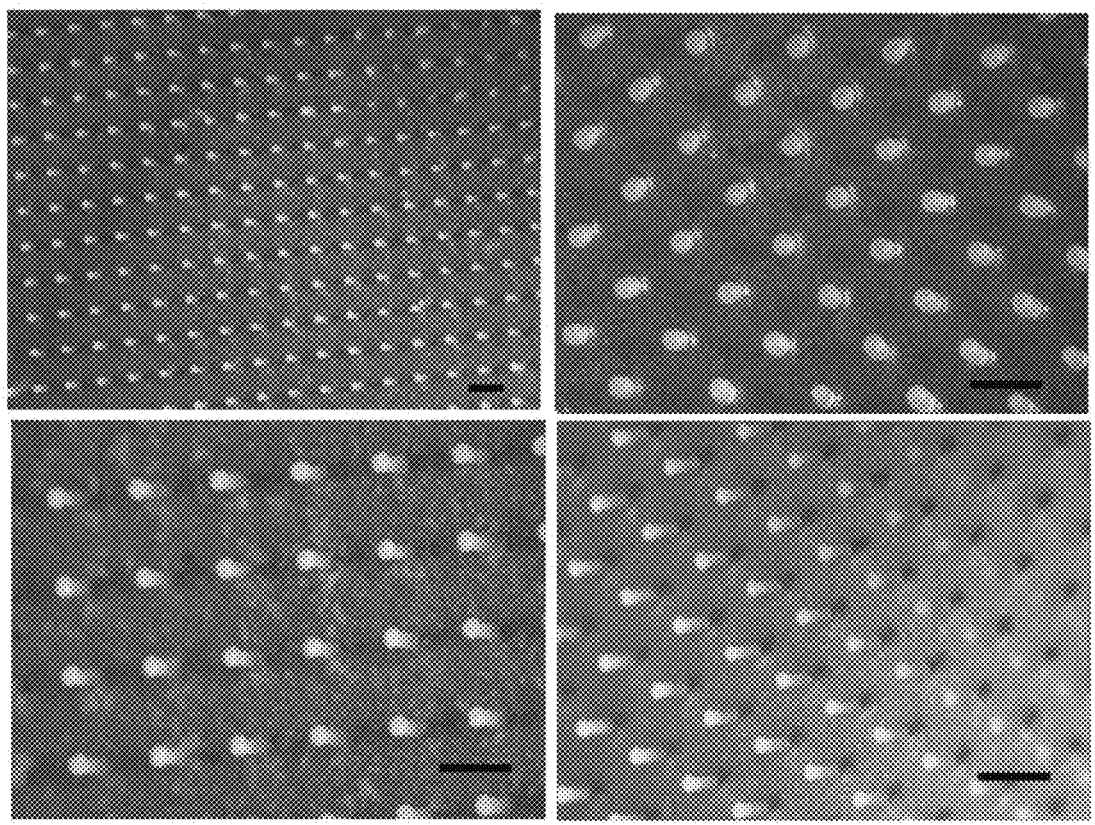
FIG. 21A-21B. Examples of patterned DFO patches. Brightfield FIG. 21A; and scanning electron microscope (SEM) FIG. 21B.
Figure 21B:
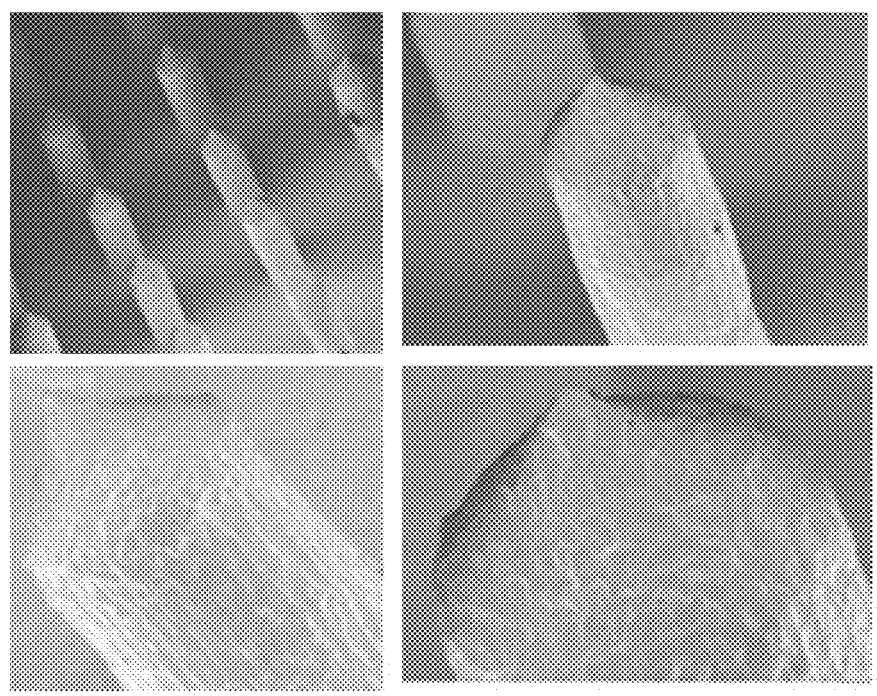

In some embodiments, a DFO patch can be a patterned patch (e.g., a microneedle patch). For example, in some cases, a silicon wafer with oxide mask can be patterned using standard contact lithographic techniques with thick photoresist and subjected to deep reactive ion etching (see Example 6 below, and FIG. 21).

In some embodiments of the invention, the HIF-1α potentiating agent is formulated in a therapeutic gel or lotion composition. The compositions of the invention include a therapeutically acceptable vehicle to act as a dilutant, dispersant or carrier, so as to facilitate its distribution and uptake when the composition is applied to the skin. Vehicles other than or in addition to water can include liquid or solid emollients, solvents, humectants, thickeners and powders.

The therapeutically acceptable vehicle will usually form 5% to 99.9%, preferably from 25% to 80% by weight of the composition, and can, in the absence of other adjuncts, form the balance of the composition.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well known to this art.

When the compositions of the invention are formulated as an emulsion, the proportion of the fatty phase may range from 5% to 80% by weight, and preferably from 5% to 50% by weight, relative to the total weight of the composition. Oils, emulsifiers and co-emulsifiers incorporated in the composition in emulsion form are selected from among those used conventionally in the cosmetic or dermatological field. The emulsifer and coemulsifier may be present in the composition at a proportion ranging from 0.3% to 30% by weight, and preferably from 0.5% to 20% by weight, relative to the total weight of the composition.

When the compositions of the invention are formulated as an oily solution or gel, the fatty phase may constitute more than 90% of the total weight of the composition. Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers and hydrophilic gelling agents may be used as described above.

Exemplary hydrocarbons which may serve as emollients are those having hydrocarbon chains anywhere from 12 to 30 carbon atoms. Specific examples include mineral oil, petroleum jelly, squalene and isoparaffins.

In use, a quantity of the composition, for example from 1 to 100 ml, is applied to a site of interest from a suitable container or applicator and, if necessary, it is then spread over and/or rubbed into the site using the hand or fingers or a suitable device. The product may be specifically formulated for use as a treatment for a specific area.

The lotion or gel composition of the invention can be formulated in any form suitable for application to the site of interest. The composition can be packaged in any suitable container to suit its viscosity and intended use. The invention accordingly also provides a closed container containing a therapeutically acceptable composition as herein defined.

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g., amounts, temperature, concentrations, etc.) but some experimental errors and deviations should be allowed for. Unless otherwise indicated, parts are parts by weight, molecular weight is weight average molecular weight, temperature is in degrees centigrade, and pressure is at or near atmospheric.

EXAMPLES

Materials/Methods

HIF-1 alpha potentiators. HIF-1 alpha potentiators are small molecules, including those that increase HIF-1 alpha stability. Topical deferoxamine (also known as desferrioxamine, desferoxamine, DFO) was used in several concentrations (1000 mM, 500 mM, 10 mM, 1 mM, 0.1 mM) depending on experimental conditions. Additionally, a number of new iron chelators such as deferiprone, deferasirox find use. Dimethyloxalylglycine (160 mg/kg) is another HIF-1 alpha potentiator that inhibits HIF-1 alpha degradation that increases HIF-1 alpha to similar levels as deferoxamine.

Transdermal Delivery of HIF-1 Alpha Potentiators.

A patch was designed for transdermal delivery system, including an adhesive, impermeable backing membrane, and a release liner containing HIF-1 alpha modulator (50-200 mg) dispersed or super-saturated within a biodegradable polymer. Preparation of transdermal patch includes a mixture of polymers (total weight, 400 mg, weighed in a 7:1 ratio of Ethyl Cellulose and Polyvinyl Pyrrolidone) and HIF-1 modulator drug, dissolved in 10 ml of chloroform. Additives are also included that prevent small molecule crystallization, resulting in enhanced drug release. Di-n-Butyl phthalate is then used as a plasticizer (30% weight-in-weight of polymers). To create the final release liner, this solution is then poured onto a sterile glass petri dish and dried at room temperature. The uniform dispersion, 2 ml each, is cast onto a 4% Polyvinyl Alcohol backing membrane and dried at 40 C for 6 hours. Finally, the backing membrane is attached to the contact adhesive (3M Tegaderm) keeping the matrix side upward. After 24 hours, the transdermal films are cut with a Delasco KP-16 mm circular punch biopsy and stored in a desiccator until further use.

Murine Wound Healing Model.

Young (8 weeks, Jackson Laboratories) aged (18-24 months, National Institute of Aging aged rodent colony), and Diabetic (Db/Db) C57/BL6 mice (n=4 per group) underwent excisional wound biopsies in accordance with the Stanford University Institutional Animal Care and Use Committees. Wounds were made as previously described. Briefly, two 6-mm circular, full-thickness wounds were made on the dorsum of mice. A 12 mm diameter, 0.5 mm thick donut shaped silicone ring (Grace Bio-Labs, Bend, Oreg.) was then placed around the wounds preventing premature skin contracture. The silicone rings were glued to the skin with cyanoacrylate glue (Elmer's Products Inc, Columbus, Ohio) and sutured in place with 6 interrupted 6-0 nylon sutures (Ethicon Inc, Somerville, N.J.). Wounds were dressed with a sterile occlusive dressing that was changed daily, monitored, and photographed every other day until closure. Wound area was compared to the area of the inner silicone ring and reported as percentage of the original wound ratio.

Pressure Ulcer Model.

Pressure ulcers on the dorsum of aged mice (19 month, NIA) and Diabetic (Db/Db) C57Bl/6 mice (n=6 per group) where created using two ceramic magnets (12 mm diameter and 5 mm thick, and average weight of 2.4 g) that apply 50 mm Hg pressure to the skin between them (Stadler et al. J Invest Surg. 2004 July-August; 17(4):221-7). A single ischemia/reperfusion (I/R) cycle consists of placement of magnets (ischemia) for a designated time period followed by release (reperfusion). Three ischemia-reperfusion cycles were used in each animal to initiate decubitus ulcer formation (either in 3 h or 12 h cycles). Animals were housed individually, to prevent the accidental dislocation of the magnets and to prevent tampering with the resultant ulcer.

ELISA.

Total protein was isolated from harvested wounds by homogenizing tissue in RIPA buffer. VEGF and SDF-1 levels were measured using the Quantikine murine VEGF and SDF-1 ELISA kits (R&D Systems, Minneapolis, Minn.) according to manufacturer's instructions.

Immunohistochemstry.

CD31 staining was performed on paraffin embedded 5-micron wound sections (1:50, Santa Cruz Biotechnology, Santa Cruz, Calif.) diluted in blocking goat serum overnight at 4° C. Sections were then stained with goat anti-rat FITC secondary antibody (Santa Cruz Biotechnology, Santa Cruz, Calif.) for 1 hour at room temperature. Sections were then mounted with Vectashield plus DAPI (Vector Laboratories, Burlingame, Calif.), and analyzed using a Zeiss Axioplan 2 light-fluorescent microscope (Carl Zeiss Vision, Germany) equipped with Zeiss AxioCam HR digital imaging software (Carl Zeiss Vision). CD31+ vessel counts were performed by counting the number of capillaries present in 4 separate 40× high power fields (HPF). TUNEL (Roche) staining was also performed. All measurements were performed by two blinded observers.

Superoxide Assay (DHE).

30 μm fresh frozen sections were washed with PBS and stained with 10 μM Dihydroethidium (DHE, invitrogen) at 37 C for 30 minutes. Slides were then washed with PBS, and Vectashield with DAPI was added.

Western Blot.

50 μg of nuclear protein extract using a NE-PER kit (Pierce) and supplemented with protease inhibitor cocktail (company). Lysate protein concentrations were determined with the Micro BCA Protein Assay Kit (Pierce). Then 50 μg of nuclear lysate was fractionated by SDS-polyacrylamide gel electrophoresis (PAGE) and analyzed by immunoblotting. Protein detection was performed with primary antibodies against HIF-1α (1:500 dilution, Novus Biologicals, Littleton, Colo.) and β-actin (1:5000 dilution, Lab Vision, Fremont, Calif.) in 5%/TBS-T overnight at 4° C. Blots were then incubated with the corresponding HRP-linked secondary antibodies (1:10,000 dilution, BD Pharmingen, San Jose, Calif.) for one hour at room temperature. Blots were developed with ECL detection reagent (Amersham, UK) and exposed for 1-10 minutes using Biomax-MS film (Kodak, Rochester, N.Y.).

Example 1

In a murine wound healing model, we have found that HIF-1 modulators act to dramatically improve healing rates and tissue survival by significantly increasing the density of blood vessels when administered topically and transdermally. In a murine pressure ulcer model, we have shown that HIF-1 alpha modulators provide an efficient and sustained means of preventing decubitus ulcer formation compared to delivery controls (FIG. 1A, 1B). Additionally, ulcer closure rates significantly increase through the correction of neovascularization (FIG. 1C). We have found that this occurs due to a dose-dependent induction of HIF-1 alpha directly and indirectly, by decreasing degradation (FIG. 2A). Induction of HIF-1 alpha increases downstream hypoxia responsive genes, which in turn decrease reactive oxygen species (FIG. 3A), stimulate vascular growth (FIG. 2C, 3B), decrease cell death (FIG. 3C), and thus improve wound healing. HIF-1 alpha modulators have promising implications for preventing ulcer formation and improving wound healing in debilitated elderly patients.

For topical delivery, deferoxamine embedded within a poloxamer gel (Pluronic F127) provides an efficient and targeted means of delivery. Hydrogels responsive to external stimuli such as pH or temperature have been studied extensively and employed for the delivery of HIF-1 alpha modulators. Because this gel can be applied topically to the wound without risks of evaporation or movement, it can deliver sustained, targeted therapy to wounds.

We have been able to characterize the biophysical properties showing effective topical delivery system for DFO including temperature and pH sensitivity, half-life, and toxicity profiles. For transdermal delivery, we have designed a transdermal patch, including an adhesive, impermeable backing membrane, and a release liner containing HIF-1 alpha modulator dispersed or super-saturated within a biodegradable polymer (FIG. 2B).

Preparation of one type of transdermal patch includes a mixture of polymers (weighed in requisite ratios of Ethyl Cellulose and Polyvinyl Pyrrolidone) and HIF-1 modulator drug, dissolved in chloroform. Additives are also included that prevent small molecule crystallization, resulting in enhanced drug release. Di-n-Butyl phthalate is then used as a plasticizer (30% weight-in-weight of polymers). To create the final release liner, this solution is then poured onto a sterile glass petri dish and dried at room temperature. The uniform dispersion is cast onto a 4% Polyvinyl Alcohol backing membrane and dried at 40 C for 6 hours. Finally, the backing membrane is attached to the contact adhesive (3M Tegaderm) keeping the matrix side upward. After 24 hours, the transdermal films are cut with a Delasco KP-16 mm circular punch biopsy and stored in a desiccator until further use.

Topical application of HIF-1 modulators can be varied based on carrier agent. While Pluronic F127 is the most extensively studied poloxamer, a number of other carriers have also demonstrated clinical efficacy. Smart hydrogels which respond to environmental stimuli such as pH and temperature have been developed to help ensure the bioactivity of drugs after delivery. Hydrogels are based on different polysaccharides, such as alginate, cellulose, chitosan, and dextran, which in turn respond to different environmental stimuli. Specifically, a chitosan based hydrogel can be manipulated to respond to temperature and pH in wound healing applications. Likewise, poloxamers such as P188 can be employed as a drug delivery gel and has demonstrated cytoprotective effects in animal models.

Transdermal patches are currently manufactured using several methods, including an adhesive, impermeable backing membrane, and a release liner. The amount of each polymer and chemicals used for patch preparation can have several modifications for maximal shelf life as well as diffusion rates.

Example 2

Targeting the HIF-1 alpha regulated neovascularization cascade reverses the impairments seen with diabetic wounds. HIF-1 alpha modulators such as deferoxamine and dimethyloxalylglycine, are small molecules that increase HIF-1 alpha stability. Deferoxamine (also known as desferrioxamine, desferoxamine, DFO) is a FDA-approved iron chelator approved for systemic administration. Dimethyloxalylglycine inhibits HIF-1 alpha degradation, thus also increasing HIF-1 alpha levels. These HIF-1 modulators can treat and more importantly prevent a broad range of diabetic wounds and ulcers in humans.

In a murine wound healing model, we have found that local delivery of HIF-1 alpha modulators act to dramatically improve healing in aged animals comparable to young controls (FIG. 4A, 7A), and in diabetic animals (FIG. 5A, 7B). Diabetic animals show markedly decreased wound healing, with wound closure at Day 23. Treatment with topical delivery of HIF-1 alpha modulators results in significantly improved wound healing, with wound closure at Day 13. Additionally, significant tissue survival is noted with the increased of blood vessel density (FIG. 2B) when administered topically and transdermally. In a murine pressure ulcer model, we have shown that transdermal delivery of HIF-1 alpha modulators provide an efficient and sustained means of treating diabetic ulcer formation compared to delivery controls (FIG. 7C).

Furthermore, we have discovered there is a dose-dependent increase in closure rates through the correction of neovascularization (FIG. 5B). We have found that this most likely occurs due to induction of HIF-1 alpha directly and indirectly, by decreasing degradation (FIG. 6B). Induction of HIF-1 alpha increases downstream hypoxia responsive genes, which stimulates an increase in vascular growth and improves wound healing. HIF-1 alpha modulators have promising implications for treating diabetic wounds and ulcers.

For topical delivery, deferoxamine embedded within a poloxamer gel (Pluronic F127) provides an efficient and targeted means of delivery. Hydrogels responsive to external stimuli such as pH or temperature have been studied extensively and employed for the delivery of HIF-1 alpha modulators. Because this gel can be applied topically to the wound without risks of evaporation or movement, it can deliver sustained, targeted therapy to wounds. We have been able to characterize the biophysical properties showing effective topical delivery system for DFO including temperature and pH sensitivity, half-life, and toxicity profiles.

For transdermal delivery, we have designed a transdermal patch, including an adhesive, impermeable backing membrane, and a release liner containing HIF-1 alpha modulator dispersed or super-saturated within a biodegradable polymer (FIG. 6A). Preparation of one type of transdermal patch includes a mixture of polymers (weighed in requisite ratios of Ethyl Cellulose and Polyvinyl Pyrrolidone) and HIF-1 modulator drug, dissolved in chloroform. Additives are also included that prevent small molecule crystallization, resulting in enhanced release of the drug. Din-Butyl phthalate is then used as a plasticizer (30% weight-in-weight of polymers). To create the final release liner, this solution is then poured onto a sterile glass petri dish and dried at room temperature. The uniform dispersion is cast onto a 4% Polyvinyl Alcohol backing membrane and dried at 40 C for 6 hours. Finally, the backing membrane is attached to the contact adhesive (3M Tegaderm) keeping the matrix side upward. After 24 hours, the transdermal films are cut with a Delasco KP-16 mm circular punch biopsy and stored in a desiccator until further use. The targeted delivery of HIF-1 alpha modulators through topical gels and transdermal patches can prevent and treat diabetic wounds and ulcers.

Example 3

New vessel growth is essential for the delivery of nutrients and maintenance of oxygen homeostasis in cutaneous tissue repair. As such, inadequate neovascularization is a major factor in the development of chronic wounds. Diabetic patients are at an increased risk for impaired tissue recovery following ischemic insult and are known to have severe deficits in wound healing. Diabetic foot ulcers represent one of the most common sequelae of diabetes-associated dysfunction in new blood vessel growth and are associated with considerable morbidity. The predictable location of these lesions and their well-described patho-physiology makes diabetic foot ulcers an ideal target for therapeutic interventions aimed at treatment and prevention through restoration of normal neovascularization.

Diabetic foot ulcers develop as a result of repetitive and prolonged pressure exerted on the skin, soft tissue, and bone. This is exacerbated by a loss of protective sensation and compounded by structural deformities to the bony architecture. These forces cause microcirculatory occlusion, local ischemia, and tissue damage, ultimately resulting in tissue necrosis and ulcer development. We and others have demonstrated that this dysfunction is attributable to diminished activity of the transcription factor hypoxia-inducible factor-1 alpha (HIF-1α). We have previously demonstrated that systemic delivery of the small molecule deferoxamine (DFO) is sufficient to stabilize HIF-1α in diabetic models, resulting in improved wound healing and decreased tissue necrosis.

Using a novel transdermal patch, we have determined that targeted transdermal delivery of DFO is effective to both prevent pressure ulcer formation and accelerate wound healing in preclinical models. A novel, prophylactic strategy to enhance local blood vessel formation and other hypoxia-induced responses, which has the potential to significantly attenuate both the formation and progression of wound healing complications in diabetic patients is described herein.

Diabetes is a known risk factor for impaired tissue recovery following an ischemic insult. Accordingly, diabetes is associated with an increased risk of vascular comorbidities including cardiovascular and peripheral vascular disease, as well as impairments in wound healing. Due in large part to these complications, diabetes accounts for 180 billion dollars in annual health costs in the US. While the attention given to preventing and treating the sequelae of type 2 diabetes has been warranted given its increasing global prevalence, type 1 diabetes remains a major cause of morbidity and mortality, especially in children. As treatment regimens for type 1 diabetes have improved, there are more adults living with this chronic disease, which translates to an increasing burden of diabetes-related complications across all age groups. New vessel growth is essential for the delivery of nutrients and maintenance of oxygen homeostasis in cutaneous tissue repair, and inadequate vasculogenesis is a major factor in the development of chronic wounds. These include diabetic foot ulcers, which represent one of the most common sequelae of diabetes-associated impairments in wound healing.

Diabetic foot ulcers develop as a result of repetitive and prolonged pressure exerted on the skin, soft tissue, and bone by the weight of an individual as a loss of protective sensation is compounded with structural deformities to the bony architecture. These forces cause microcirculatory occlusion as pressures rise above capillary filling pressure, resulting in tissue ischemia. When blood supply returns (reperfusion) to the tissue after a period of ischemia, inflammation and subsequent tissue damage occur. Over time, the cumulative hypoxia leads to cell death and tissue necrosis, resulting in ulcer development. Given the well described mechanism underlying their pathology, and the predictable location of these lesions, diabetic foot ulcers represent an ideal target to evaluate therapeutic interventions aimed at restoring normal neovascularization.

We and others have identified the underlying mechanism responsible for impaired neovascularization with diabetes: dysfunctional vasculogenesis due to reduced stabilization of the transcription factor hypoxia inducible factor-1 alpha (HIF-1α). HIF-1α is the chief regulator of cellular responses to hypoxia and ischemia$_{35}$ and functions as a master regulator of oxygen homeostasis. Under hypoxic conditions, HIF-1α is stabilized and translocates to the nucleus where it initiates expression of multiple gene pathways that enhance oxygen delivery and increase metabolism, most notably vascular endothelial growth factor (VEGF). This rapid and dynamic process permits a near-immediate tissue response to hypoxia. Hyperglycemia and diabetes impair HIF-1α function, resulting in decreased transcription of angiogenic genes and impaired neovascularization in response to ischemia, leading to deficits in wound healing.

We and others have demonstrated that by restoring normal HIF-1α function in the setting of diabetes, normal wound healing is restored. We recently reported that HIF-1α is modified by the glycolytic metabolite methylglyoxal, which prevents HIF-1α activation, culminating in the reduced transcription of several vasculogenic genes. High glucose induced methylglyoxal byproducts also prevents association of HIF-1α with its coactivator p300, markedly reducing HIF-mediated gene transcription. Hyperglycemia-mediated overproduction of ROS by the mitochondrial electron transport system contributes to this effect. This causes a reduction in activity of the glycolytic enzyme GAPDH, with consequent accumulation of glycolytic metabolites that cause cellular damage. Another important modification of protein function involves the production of advanced glycation endproducts (AGE), which are formed through reduction of glucose byproducts that cross-link with proteins and disrupt normal function. In aggregate, the mechanisms of increased levels of ROS, AGEs and resultant chronic oxidative stress have been presented as a "unifying theory" of diabetic vascular complications.

Iron chelators such as deferoxamine (DFO) have been proposed as therapeutic agents to ameliorate these harmful molecular pathways, and iron chelation has been shown to enhance the vascular response to ischemia by stabilizing HIF and restoring its function. DFO has an added advantage in that it also has a direct antioxidant effect, which reduces the oxidative stress suffered by diabetic cells and tissues during hypoxia. DFO has been used for protective hypoxic preconditioning in brain$_{56}$ and heart tissue, and in limited studies in cutaneous ischemic preconditioning. Collectively, these studies suggest a role for DFO in both preventing and treating diabetic ulcers.

Given the therapeutic potential of DFO to augment cutaneous neovascularization, we have developed a transdermal delivery system to administer this small molecule directly to ulcerated or high-risk tissue. Prevention of wound development has never previously been attempted using a small molecule therapeutic. We have developed a polymeric, micelle-based transdermal patch that permits prolonged, measured deliver of DFO directly across the skin. This patch is composed of three layers: an adhesive, an impermeable backing membrane, and a release layer containing DFO dispersed within a biodegradable polymer of ethyl cellulose and polyvinyl pyrrolidone (PVP). Nontoxic additives are used to prevent crystallization and enhance drug release. We have demonstrated the ability of this device to augment neovascularization and accelerate wound healing, as described below.

The small molecule deferroxamine (DFO) sequesters iron, which is critical for PHD-mediated HIF degradation. We evaluated the efficacy of this molecule in vivo using our murine excisional wound healing model. When DFO was applied topically to diabetic lesions, gross wound healing was accelerated and wound vascularity was significantly improved. Additionally, DFO dramatically increased HIF-1α stabilization when applied to diabetic murine fibroblasts in vitro.

We evaluated the ability of DFO to prevent pressure ulcer formation, which has been associated with HIF-1α dysfunction and diabetes, using a previously described murine pressure ulcer model. Briefly, two ceramic magnets are placed on the mouse dorsum, applying 50 mmHg pressure to the interlaying skin (FIG. 8A), resulting in measurable oscillations of oxygen tension across repetitive cycles of magnet application (ischemia) and removal (reperfusion). Aged mice subjected to this model were treated with intraperitoneal DFO or saline at day −1 and every other day until ulcer closure. DFO-treated mice demonstrated significantly less ulcer formation and improved wound healing (FIG. 8B-C). Treated mice also exhibited increased neovascularization and decreased apoptosis (FIG. 8D), as well as increased EPC mobilization. These findings demonstrate that prophylactic DFO can prevent pressure ulcer formation in high-risk patients.

Targeted, transdermal delivery of DFO stabilizes HIF-1α: We developed a novel transdermal delivery system to deliver targeted DFO, as described above. We first evaluated the ability of our transdermal patch to deliver DFO across unwounded mouse skin, and demonstrated consistent HIF-1α stabilization within 48 hours of application (FIG. 9A). The patch was then applied to our excisional wound model, and HIF-1α stabilization at the wound was achieved at day 2 (FIG. 9B).

Transdermal DFO release occurs in a controlled fashion: The release layer of our patch incorporates DFO into polyvinyl pyrrolidone (PVP) micelles within a biocompatible ethyl cellulose polymer film, which allow for controlled release based on polymer degradation. We utilized scanning electron micrographs to verify the release properties of encased PVP-DFO micelles (FIG. 10, bottom). Following 48 hours of PBS incubation, microvoids are observed which represent polymer film regions previously containing DFO micelles (FIG. 10, top). The ethyl cellulose-based controlled release biomaterial provides an additional method to deliver this HIF stabilizing therapeutic transdermally.

Transdermal DFO diffuses across human skin: We evaluated the capacity of our DFO-eluting transdermal patch to penetrate the thicker dermal tissue of human cadaveric skin. We first developed a histochemical protocol to evaluate DFO levels in tissue sections using potassium ferrocyanide staining to identify DFO interactions with iron aggregates following incubation with a ferrosulfate solution (FIG. 11, top). In order to ensure the specificity of these findings we employ a MALDI-TOF imaging to specifically detect the presence of DFO complexed with iron observed at 656 nm (FIG. 11, bottom-right).

Figure 12:
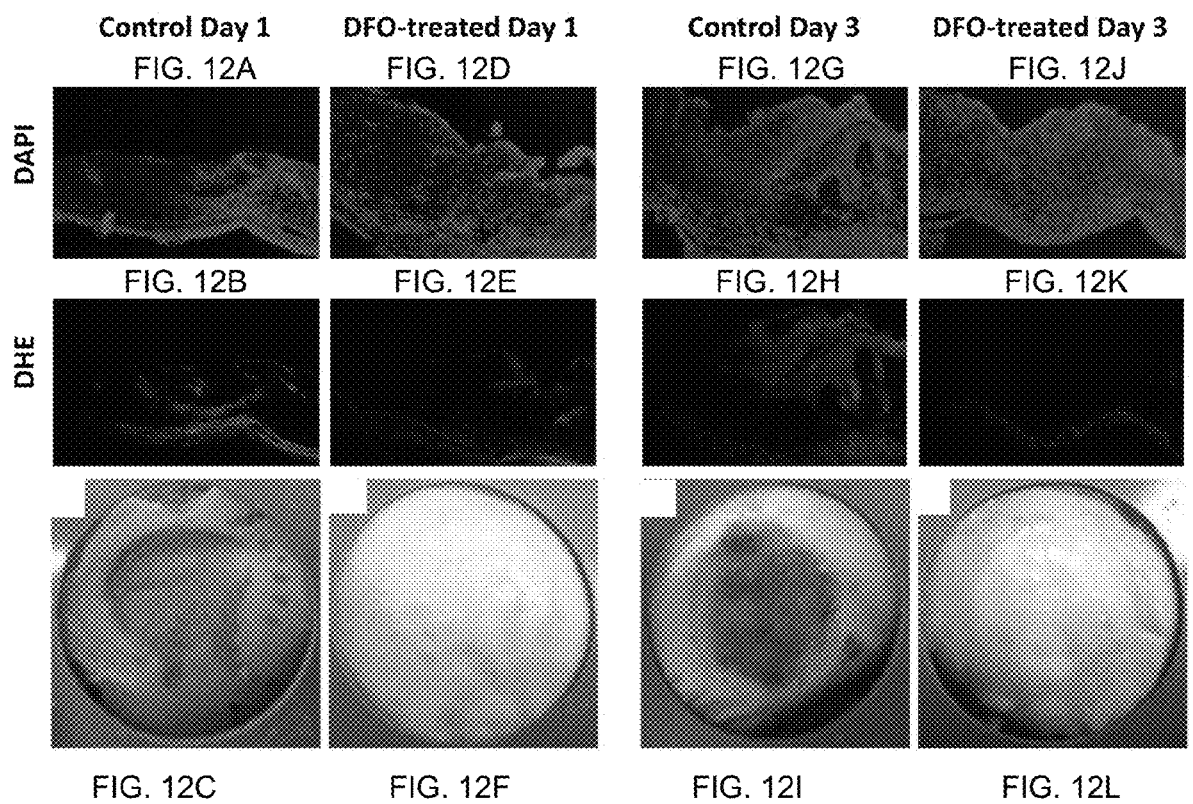
FIG. 12A-12L.

Transdermal delivery of DFO reduces ROS accumulation and ulcer formation: We have completed studies examining the ability of our DFO patch to ameliorate diabetes-associated deficits in wound healing using our pressure ulcer model. This injury model causes increased levels of ROS, as assayed using dihydroethidium (DHE) fluorescent staining. Treatment of murine skin with DFO delivered via our transdermal patch resulted in a dramatic decrease in ROS accumulation at days 1 and 3 (FIG. 12) with a corresponding decrease in gross skin injury. These data suggest the efficacy of our DFO delivery systems to augment skin repair.

Figure 13:
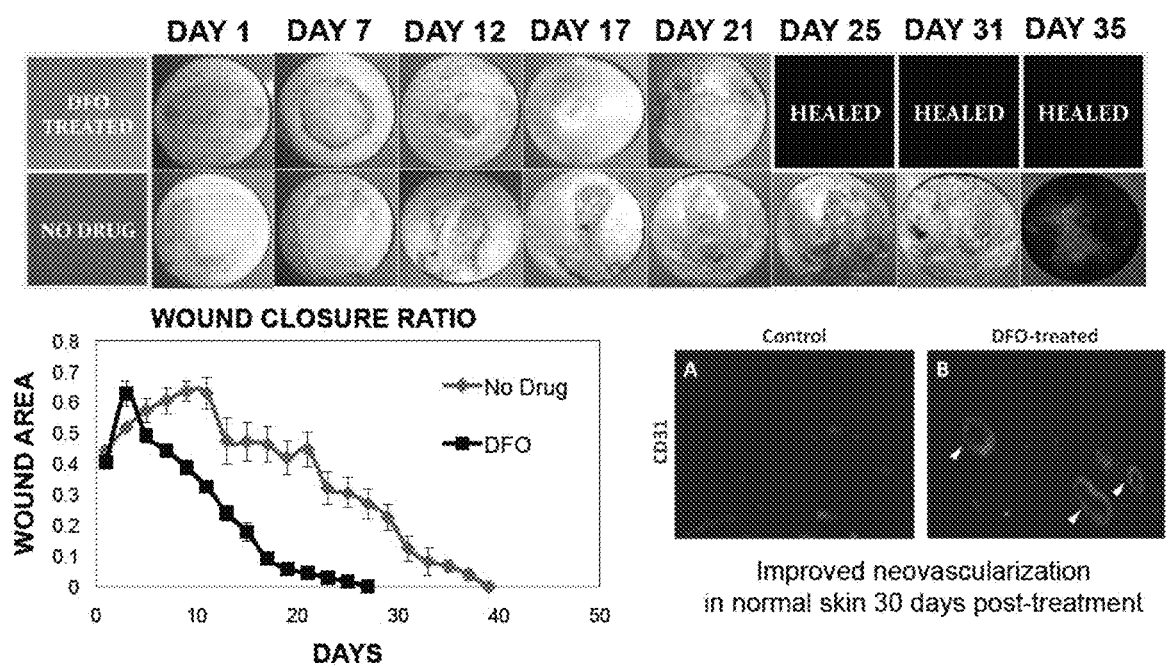
FIG. 13. Transdermal delivery of DFO improves recovery of murine full thickness wounds FIG. 14. Comparison of nicotine and DFO release.

Transdermal delivery of DFO accelerates murine wound healing: Given the optimal release properties and structural parameters determined above, we sought to evaluate the ability of our DFO delivery device to improve gross wound healing in diabetic mice. Patches were applied to fresh murine excisional wounds and replaced every two days. Mice treated with DFO patches exhibited significantly improved wound healing compared to those receiving sham (PBS) patches (FIG. 13). These results demonstrate the efficacy of our DFO delivery system for the acceleration of diabetic wound healing in small animals.

Example 4

Figure 14:
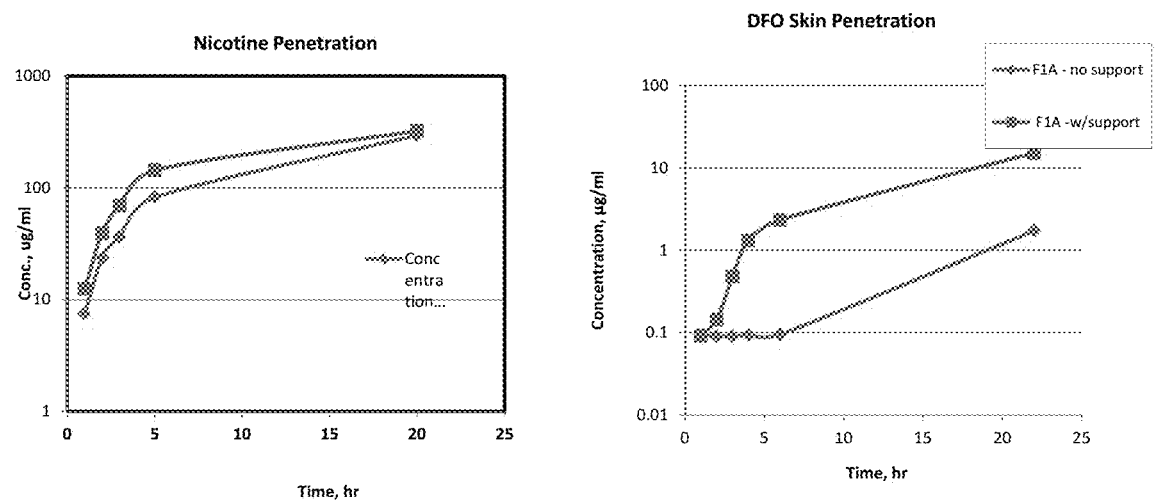

In an initial comparison of a DFO patch with a commercial nicotine patch, we found that the delivery of DFO was a full 10-fold lower than nicotine, although the presence of a support helped improve the delivery kinetics, as shown in FIG. 14. Therefore, it was important to determine a specific transdermal patch that could stably maintain the hydrophilic drug and provide for adequate skin penetration.

Specific formulations of interest include the following.

TABLE 1

| Formulation 1 | Formulation 2 | Formulation 3 |
|---|---|---|
| DFO 100 mg | DFO 100 mg | DFO 100 mg |
| Tween-80 100 mg | PEG 6000 100 mg | Tween-80 100 mg |
| Span-20 100 mg | Cetyl alcohol 30 mg | Span-20 100 mg |
| PVP (360k) 50 mg | Plurol Oleique 50 mg | PVP (10k) 50 mg |
| Cetyl alcohol 30 mg | Ethyl cellulose 500 mg | Cetyl alcohol 30 mg |
| Plurol Oleique 50 mg | | Plurol Oleique 50 mg |
| Ethyl cellulose 350 mg | | Ethyl cellulose 350 mg |

| Formulation 4 | Formulation 5 | Formulation 6 |
|---|---|---|
| DFO 100 mg | DFO 100 mg | DFO 100 mg |
| PVP (10k) 50mg | PVP (10k) 80 mg | CTAB 130 mg |
| PEG-6000 100 mg | Cetyl alcohol 50 mg | PVP 120 mg |
| Cetyl alcohol 30 mg | Plurol Oleique 120 mg | Ethyl cellulose 400 mg |
| Plurol Oleique 50 mg | Ethyl cellulose 400 mg | |
| Ethyl cellulose 500 mg | | |

Preparation of DFO Patch (general procedure of all six formulations above): Weigh each of components for the amount as given in the formulation table. Dissolve all the components separately as follows: (Eg. Formulation 1 for 100 cm² patch), Ethyl Cellulose (ethoxy content: 48%, 110 cps supplied by Acros Organics, N.J.) in 5 mL of ethanol, Polyvinyl Pyrrolidone (MW: 10,000, Sigma, St Louis Mo.) in 1 ml of ethanol, DFO (deferoxamine mesylate) 1 mL of 50% ethanol-water mixture, Tween-80 and Span-20 in 1 mL of ethanol, plurol oleique in 1 mL of ethanol, cetyl alcohol in 1 mL of ethanol. All of the solutions were mixed, and made up to a total volume of 10 mL with ethanol. Stir the solution for 30 min. Pour the solution (10 mL) to a Teflon coated tray (100 cm²-10×10 cm) (or 0.1 mL per cm²). Evaporate the ethanol by drying it at 37° C. for 12 hours. The dried films were removed and cut to the required sizes. The patches were attached to the adhesive membrane (3M Tegaderm) and stored in desiccator (ready to use).

Sources are as follows.

TABLE 2

| Ethyl cellulose, ethoxyl content 48%, 22 cps | variable | Thermo Fisher Scientific Geel - Belgium |
|---|---|---|
| Polyvinyl Pyrrolidone | average mol wt 10,000 | Sigma-Aldrich, Inc. St Louis, MO |
| Absolute Ethanol (200 Proof) | 46.07 | Sigma-Aldrich, Inc. St Louis, MO |
| Deferoxamine mesylate | 656.8 | EMD Biosciences, Inc. La Jolla, CA |
| Tween 80 | 1310 | MP Biomedicals, LLC Solon, OH |
| Span 20 | 346.47 | Sigma-Aldrich, Inc. St Louis, MO |
| Plurol Oleique | 726.93 | Pharmaceutical Division Gattefossé USA Plaza I, 115 West Century Road, Suite 340 Paramus, NJ 07652 |

From the formulations listed in Table 1, preferred formulations include formulation 5 and formulation 6.

An additional specific formulation of interest includes:

| Formulation 7 |
|---|
| DFO 100 mg |
| PVP 80 mg |
| Cetyl alcohol 50 mg |
| Plurol Oleique 120 mg |
| Ethyl cellulose 400 mg |
| (Ethyl alcohol 10 ml) |

Preparation of Formulation 7:
(1) Dissolve 1600 mg of ethyl cellulose in 24 ml of ethanol (stirring overnight, turbid solution).
(2) Combine Cetyl alcohol, PVP, Plurol Oleque, and 16 ml of ethanol; and stir.
(3) Weigh out 400 mg of DFO, wet it with about 400 µl of water, add solution from (2) and stir (will be a suspension).
(4) Combine (1) and (3), stir.
(5) Setup 8-well tray on a flat level surface at a temperature of 37° C.
(6) Dispense 4 ml of (4) to each well, cover with tissue/paper towel. Let dry overnight.
(7) Using spatula remove patches from the tray. Store in an airtight container at room temperature.

An additional specific formulation of interest includes:

| Formulation 8 |
|---|
| DFO 100 mg |
| PVP 80 mg |
| Cetyl alcohol 50 mg |
| Plurol Oleique 120 mg |
| Ethyl cellulose 400 mg |
| (Ethyl formate 10 ml) |

Preparation of Formulation 8:
(1) Dissolve 1600 mg of ethyl cellulose in 24 ml of ethyl formate (stirring overnight, turbid solution).
(2) Combine Cetyl alcohol, PVP, Plurol Oleque, and 16 ml of ethyl formate; and stir.
(3) Weigh out 400 mg of DFO, wet it with about 600 µl of water, add 600 µl of solution from (2). Add rest of (2) and stir (will be a clear solution).
(4) Combine (1) and (3), and stir (will become cloudy, but will not sediment).
(5) Setup 8-well tray on a flat level surface at a temperature of 37° C.
(6) Dispense 4 ml of (4) to each well, cover with tissue/paper towel. Let dry overnight.
(7) Using spatula remove patches from the tray. Store in an airtight container at room temperature.

An additional specific formulation of interest includes:

| Formulation 9 |
|---|
| DFO 100 mg |
| PVP 80 mg |
| CTAB 80 mg |
| Ethyl cellulose 500 mg |
| (Ethyl alcohol 10 ml) |

Preparation of Formulation 9:
(1) Dissolve 1600 mg of ethyl cellulose in 24 ml of ethyl alcohol (stirring overnight, turbid solution).
(2) Combine CTAB, PVP, and 16 ml of ethyl alcohol; and stir.
(3) Weigh out 400 mg of DFO, wet it with about 600 µl of water, add 600 µl of solution from (2). Add rest of (2) and stir (will be turbid solution with visible swirls when shaken).

(4) Add 1.2 ml of water, stir overnight. Add another 1 ml of water.
(5) Combine (1) and (4), and stir (will become cloudy, but will not sediment).
(6) Setup 8-well tray on a flat level surface at a temperature of 37° C.
(7) Dispense 4 ml of (5) to each well, cover with tissue/paper towel. Let dry overnight.
(8) Using spatula remove patches from the tray. Store in an airtight container at room temperature.

An additional specific formulation of interest includes:

| Formulation 10 |
| --- |
| DFO 100 mg |
| PVP 80 mg |
| CTAB 80 mg |
| Ethyl cellulose 400 mg |
| (Ethyl formate 10 ml) |

Preparation of Formulation 10:
(1) Dissolve 1600 mg of ethyl cellulose in 24 ml of ethyl formate (stirring overnight, turbid solution).
(2) Combine CTAB, PVP, and 16 ml of ethyl formate; and stir (will not dissolve). Add 500 µl×3 (1.5 ml) of water (will be a turbid solution)
(3) Weigh out 400 mg of DFO, wet it with about 600 µl of water, add 600 µl of solution from (2). Add rest of (2) and stir (will be turbid solution with visible swirls when shaken).
(4) Add 1.2 ml of water, stir overnight. Add another 1 ml of water.
(5) Combine (1) and (4), and stir (will become cloudy, but will not sediment).
(6) Setup 8-well tray on a flat level surface at a temperature of 37° C.
(7) Dispense 4 ml of (5) to each well, cover with tissue/paper towel. Let dry overnight.
(8) Using spatula remove patches from the tray. Store in an airtight container at room temperature.

Exemplary DFO patches made using formulations 7 to 10 above are depicted in FIG. 20. The patches using formulations 9 and 10 above can also be made by substituting a different solvent for ethyl formate (e.g., isooctane, n-heptan, a super critical fluid of $CO_2$, and the like). These substitute solvents can be used with volumes up to 2 times that of what is described for ethyl formate above.

Among the advantages of DFO are that it has a better chance of being transdermally deliverable than most others. Applicants initial efforts showed that Anti-crystallizers are key in formulation. Specifically, the more API is added the harder it is to prevent crystallization and the more anti-crystallizer required. Early formulation work demonstrated the propensity for crystallization to occur, depicted above by polarized images where the bright coloration demonstrates crystallization. In the pictures above, B3 and C1 represent minimal crystallization. The amount of DFO had to be balanced to prevent crystallization while still delivering sufficient API through the skin. Many initial formulations resulted in significant crystallization.

Figure 15:
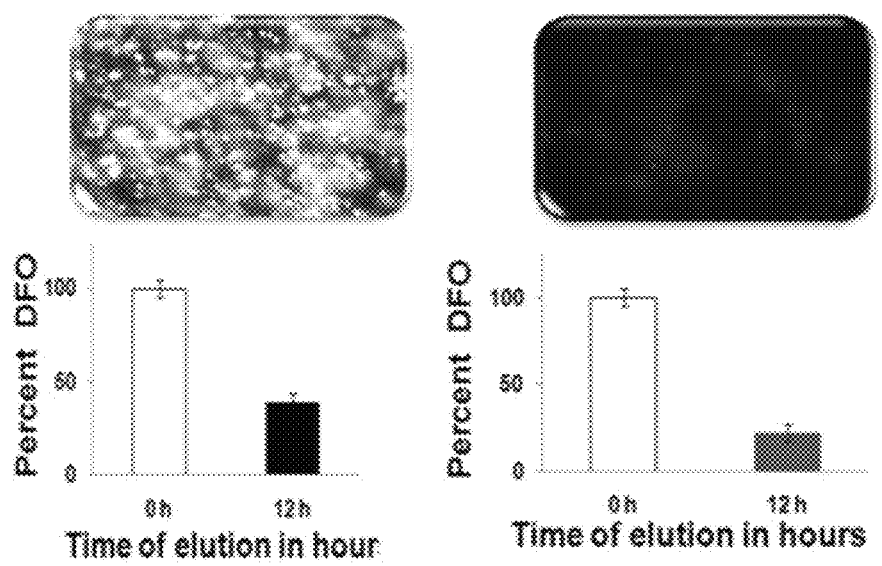
FIG. 15. Comparison of elution profiles of formulations with and without crystallization demonstrating superiority of non-crystalline formulations in DFO delivery.
Figure 16:
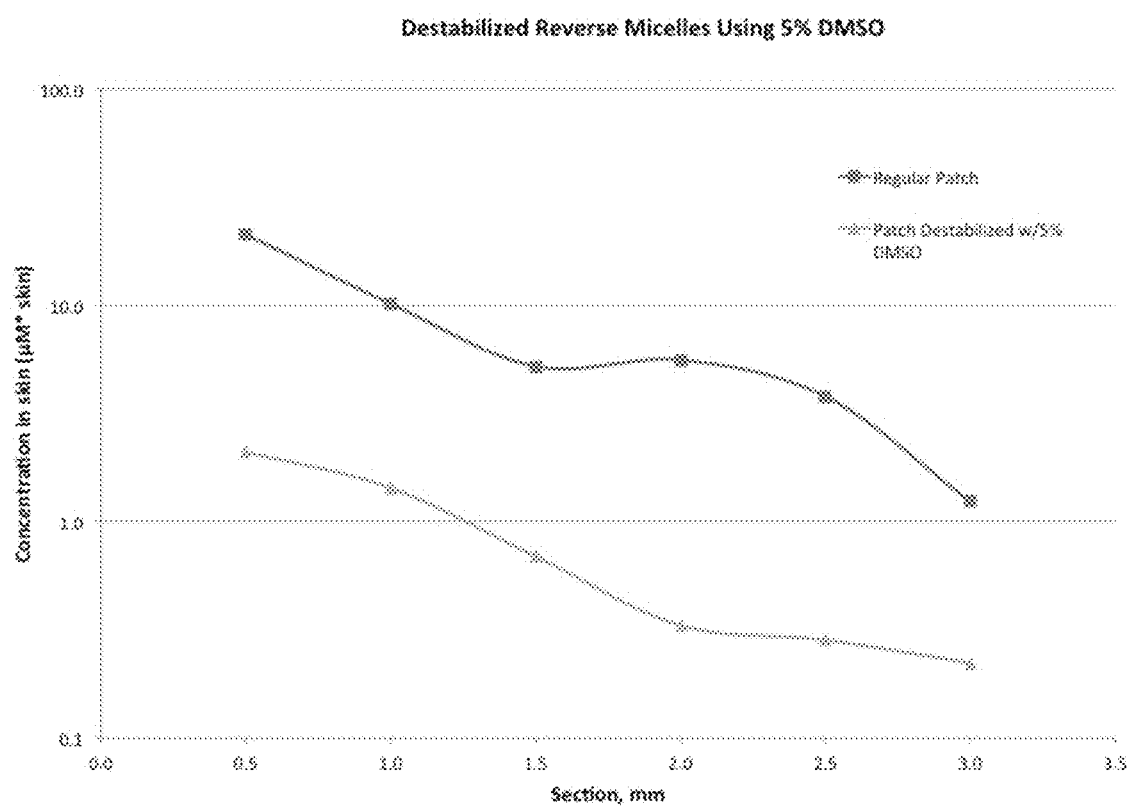
FIG. 16. DFO concentration at varying skin depths, demonstrating that destabilizing the reverse micelle using 5% DMSO significantly reduces the DFO uptake into the skin.
Figure 20A:
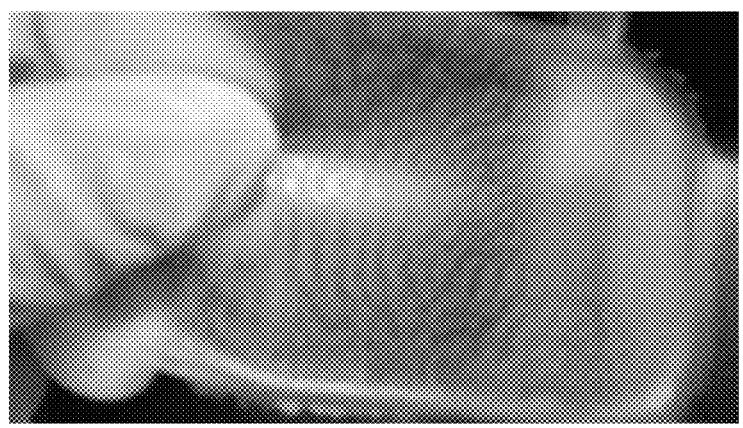
FIG. 20A-20D. DFO patches of specific formulations.
Figure 20B:
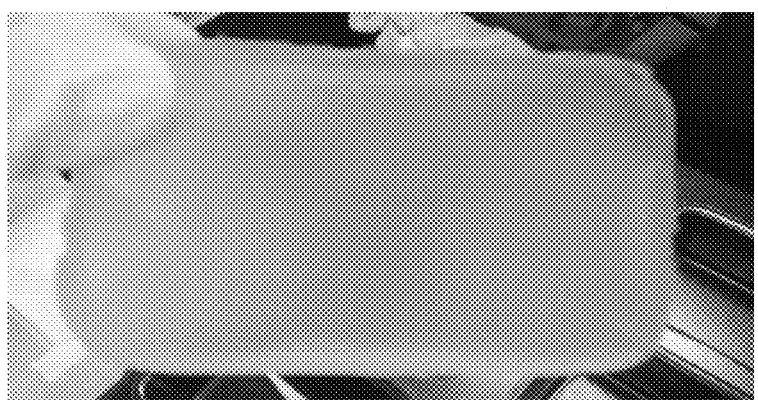
Figure 20C:
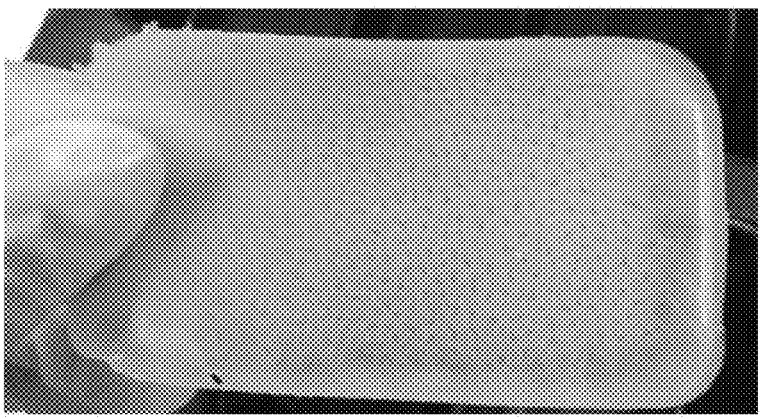
Figure 20D:
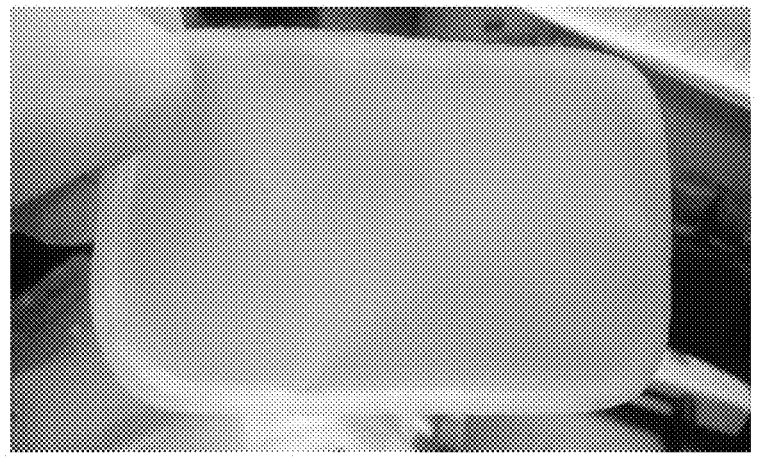

The crystallization is significant because of its effect on elution profiles, shown in FIG. 15. A non-ionic surfactant was utilized to prevent crystallization. When the working formulation was determined, it was analyzed and found to have a reverse-micelle conformation as a result of the inclusion of the surfactant. Subsequently, it was determined that the reverse micelle conformation enabled DFO delivery. This was confirmed that this by destabilizing the reverse micelles using 5% DMSO, which we found to inhibit DFO delivery (FIG. 16).

Further, it was found that there was very minimal drug penetration without an occlusive backing, giving a 10-fold reduction in skin penetration of DFO without backing membrane.

Example 5

Combating Surgical Site Infections Using a Deferoxamine-Based Wound Dressing

Surgical site infections (SSIs) can occur following both open and laparoscopic procedures (Culver et al., National Nosocomial Infections Surveillance System. Am J Med. Sep. 16 1991; 1(3B):1525-1575; Harrop et al., J Am Acad Orthop Surg 2012; 20:94-101). Recent estimates of the standardized infection rate in the US are as high as 1% (Centers for Disease Control and Prevention. National HAI standardized infection ratio (SIR) report, July-December 2009), with an increasing risk correlating with patient co-morbidities (Table 3). Moreover, the occurrence of a post-operative infection in any patient can result in unnecessary morbidity and and mortality, as well as exorbitant healthcare costs (Zhan and Miller, JAMA 2003; 290:1868-74). That SSIs still occur despite an increased focus by surgeons on post-operative wound care protocols suggests new approaches are needed to combat this problem.

TABLE 3

| ASA Preoperative Patient Risk Assessment Score | Characteristics | Surgical Site Infection (SSI) Rate (%) |
| --- | --- | --- |
| 1 | Healthy patient | 2.9 |
| 2 | Patient with systemic disease | 6.8 |
| 3 | Patient with acute systemic disease | 13 |

To strategically lower the risk of SSIs, post-operative application of deferoxamine films and/or patches are made directly to incisional sites, wherein they will act as an antibiotic dressing material. Deferoxamine is an FDA approved sideropore known to have anti-biofilm and anti-bacterial properties (Moreau-Marquis et al., Am J Respir Cell Mol Biol. 2009 September; 41(3):305-13; van Asbeck et al., Eur J Clin Microbiol. 1983 October; 2(5):432-8; Hartzen et al., APMIS. 1994 March; 102(3):219-26; van Asbeck et al., Eur J Clin Microbiol. 1983 October; 2(5): 426-31), which can be delivered by the methods of the invention in a controlled fashion to sites of interest. The patch formulations are designed to be totally biodegradable, and when applied to superficial wounds facilitate the delivery of a locally concentrated deferoxamine dose during the initial post-operative period (FIG. 17).

The transitory nature of this approach minimizes any long-term risks associated with patch, and also obviates the need for a subsequent removal procedure following successful wound closure. In the case of laparoscopic incisional wounds, a deferoxamine patch is applied to the entire wound cavity by inflating a silicon balloon catheter wrapped with a patterned deferoxamine patch within the defect (FIG. 18). The biodegradable properties of the delivery construct are important when applied in this fashion, as they enable the surgical site to be closed normally upon completion of the procedure, while providing a sustained drug delivery during the critical early post-operative period.

Example 6

Methods of Preparing a Patterned DFO Patch
Method of Preparation

A silicon wafer with oxide mask was patterned using standard contact lithographic techniques with thick photoresist and subjected to deep reactive ion etching. The residual photoresist was removed using oxygen plasma and the wafers were washed in sulfuric acid. To facilitate easy removal of molded materials, the patterned wafers were silanized overnight in a vacuum chamber prior to use. To prepare PDMS mold, PDMS monomer and curing agent (10:1 w/w, Dow Corning, Midland, Mich.) were mixed and poured onto Si wafers in a sterile Petri dish. To remove bubbles of trapped air, a vacuum was applied for 20-30 min and the Petri dishes were gently rapped. To cure the PDMS, the Petri dish was incubated at 37° C. overnight.

Ethyl cellulose 400 mg was dissolved by stirring overnight in 5 mL of ethyl alcohol. DFO 100 mg was wet with 200 μL of water and then 800 μL ethanol was added in increments of 200 μL while mixing. To this cetyl alcohol 50 mg dissolved 1 mL of ethanol was added followed by the addition of plurol oleique 120 mg. Separately, polyvinyl pyrrolidone (PVP 10 k) 80 mg was dissolved in ethanol and added to the mixture followed by the addition of ethyl cellulose solution. The formulated solution (4004) was diluted to 1 mL using ethanol to reduce the viscosity and poured on a 2 cm×2 cm micropatterned PDMS mold. The mold was placed in a vacuum to force the air bubbles out of the pattern and vacuum was released to fill liquid into the micropatterns. The vacuum/release process was repeated multiple times. The mold was allowed to dry overnight and then peeled. The concentration of DFO in the patterned patch was maintained at 1 mg per sq cm same as the non-patterned (regular) patch. See FIG. 21 for brightfield (top) and scanning electron microscope (SEM) (bottom) images of exemplary patterned DFO patches.

Example 7

Transdermal HIF-1α Stabilization Both Prevents and Improves Healing of Diabetic Ulcers Chronic diabetic wounds such as pressure sores and foot ulcers are a significant burden for patients and the healthcare system. A major factor underlying impaired wound healing in diabetic patients is impaired neovascularization caused by accelerated degradation of the transcription factor hypoxia inducible factor-1 alpha (HIF-1α). We examined whether local stabilization of HIF-1α would improve diabetic wound healing and minimize the severity of diabetic ulcers. In order to enhance HIF-1α activity, we designed a transdermal drug delivery system (TDDS) containing the FDA-approved small molecule deferoxamine (DFO), an iron chelator that stabilizes HIF-1α by inhibiting its iron-dependent degradation. Applying this TDDS to a pressure-induced ulcer model in diabetic mice, we found that transdermal delivery of DFO stabilized HIF-1α and significantly improved wound healing. Prophylactic application of this transdermal delivery system also prevented diabetic ulcer formation. DFO-treated wounds demonstrated increased collagen density, organization and improved neovascularization. These findings suggest that transdermal delivery of DFO provides a targeted means to both prevent ulcer formation and accelerate diabetic wound healing.

Materials and Methods

Design of the Transdermal Drug Delivery System

A monolithic matrix-type transdermal drug delivery system containing DFO dispersed within a biodegradable polymer was designed. DFO mesylate salt powder was purchased from Sigma-Aldrich (St. Louis, Mo.). All reagents used were analytic grade. Due to its hydrophilicity and tendency to crystallize, DFO is especially well suited for delivery complexed with the polymer polyvinylpyrrolidone (PVP). PVP stabilizes drugs in an amorphous form and to promote permeation of hydrophilic molecules. To facilitate dermal penetration of the DFO/PVP complexes, reverse micelle forming non-ionic surfactants polysorbate 80 (Tween 80) and sorbitan monolaurete 20 (Span 20) were added to the formulation. Finally, ethyl cellulose was added to form a slow releasing matrix. For the preparation of the drug release layer, the two polymers ethyl cellulose (3.5% by weight) and polyvinylpyrrolidone (0.5% by weight) were dissolved with 1% DFO (by weight) in chloroform and the non-ionic surfactants Tween 80 and Span 20 (1% each, by weight) were added for reverse micelle formation. Di-n-Butyphthalate was used as a plasticizer (30% weight-in-weight of polymers). The solution was stirred vigorously until a fine suspension was achieved. This solution was then poured onto a sterile glass petri dish and dried at room temperature. The uniform dispersion was cast onto a 2% Polyvinyl Alcohol backing membrane, dried at 40° C. for 6 hours and cut with a 16 mm circular biopsy punch in equal sized discs. Finally, the finished transdermal delivery system was attached to a contact adhesive (Tegaderm, 3M, MN). For comparison, an alternative TDDS has been formulated using the permeation enhancer DMSO instead of non-ionic surfactants and a control formulation containing only vehicle was prepared by making a suspension of the polymers and surfactants without the addition of DFO.

Scanning Electron Microscopy (SEM)

High-resolution scanning electron microscopy (SEM) of DFO TDDS was completed using a Hitachi 3400N VP scanning electron microscope (Hitachi High Technologies America, Inc., Schaumburg, Ill.) at the Stanford Cell Sciences Imaging Facility.

Atomic Force Microscopy (AFM) and Raman Spectroscopy Imaging

Both Raman and AFM were performed using NTEGRA Spectra combined AFM-Raman system (NT-MDT). AFM imaging was performed in tapping mode with commercial high-durability rounded cantilevers (k=5.4 N/m, R ~40 nm) at 0.7 Hz. This provided surface topography and phase contrast images to discern stiffness of different areas within the micelle particles. Raman confocal scanning was performed in backscattering geometry with a long-working Mitutoyo objective (100, 0.7 NA). The illumination light was 473 nm, and the power was kept at ~2 mW to lower the possibility of sample damage.

Raman maps were produced with a step size of 0.5 mm and 1 s exposure. 600 g/mm gratings were used for optimal signal and spectral resolution. The peaks at 1625 cm-1 (integrated spectral intensities 1575-1675 cm-1) were attributed to DFO molecules, while the CH bands at 2800-3050 cm-1, less DFO CH peak at 2927-2952 cm-1, were attributed to the lipid molecules.

In Vitro Drug Release

DFO TDDS was placed into 500 ml PBS buffer (pH 7.4) maintained at a temperature of 37° C., and shaken continuously for 14 hours. The concentration of DFO was measured spectrophotometrically at 560 nm (Shimadzu, Japan) every hour.

In Vitro Skin Permeation

For in vitro skin permeation studies a vertical Franz diffusion cell model has been used as previously described. Briefly, full thickness human skin samples obtained under Stanford IRB approval from abdominoplasty samples were mounted between the two compartments of the diffusion cell with the stratum corneum facing the donor compartment. All entrapped air underneath the skin was removed and the TDDS was applied. Isotonic phosphate buffer solution agitated with a magnetic stirrer and maintained at 37° C. by a circulating water jacket was used as a receptor phase. Every hour, one ml of receptor fluid was removed for spectrophotometric analysis of DFO concentration over 24 hours. Following 24 hours of TDDS exposure the skin samples were removed, washed with PBS and dried with an absorbent towel. The skin samples were frozen in −20° C. and cut with a microtome into 20 μm sections in 0.5 mm intervals from the skin surface to a depth of 2 mm. The samples were analyzed for drug content spectrophotometrically at 560 nm (Shimadzu, Japan) and the DFO concentration (μg/g skin) was determined.

Animals

Adult male C57BL/6 db/db mice (BKS. CG-M+/+Lepr<db>/J; 12 weeks; Jackson Laboratories) were utilized in all experiments in accordance with Stanford University Institutional Animal Care and Use Committees. The animals were housed five per cage prior to surgery and alone post-procedure in a temperature-controlled animal facility with a 12-hour light/dark cycle.

Western Blot

For Western blot analysis, protein was separated on a 4-12% polyacrylamide gel (Invitrogen), and then transferred to a nitrocellulose membrane (Invitrogen). Anti-HIF-1α, -Cleaved Caspase 3 and -Bax (1:500, Abcam, Inc, Cambridge, Mass.) and anti-β-actin were used as the primary antibodies. An HRP-conjugated secondary antibody was used (1:10,000) and detected using the ECL Plus Western Blotting Detection Kit (GE Healthcare, Waukesha, Wis.).

Pressure Ulcer Model and TDDS Application

Twelve week old male C57BL/6 db/db mice (BKS. CG-M+/+Lepr<db>/J; Jackson Laboratories) were randomized into the following groups: DFO TDDS treated vs vehicle TDDS control. Pressure ulcers on the dorsum of db/db mice were induced as previously described using two ceramic magnets (12 mm in diameter, 5 mm in thickness, and weight of 2.4 gram, Magneticsource.com) (FIG. 25A-D). A single ischemia/reperfusion cycle consisted of placement of magnets (ischemia) for a designated time period (3 hours or 6 hours) followed by release (reperfusion for 3 hours or 6 hours). Three ischemia-reperfusion cycles were used in each animal to initiate formation of 2 ulcers per animal. Animals were housed individually to prevent the accidental dislocation of the magnets and tampering with the resultant ulcers. Ulcers were treated with either DFO transdermal formulations or control TDDS starting either 48 hours before, 24 hours after or 7 days after ulcer induction (FIG. 26A-C). In the wound healing experiment TDDS were replaced every 48 hours until the ulcers were fully healed, in all other experiments TDDS were only applied once. All wounds were covered with an occlusive dressing (Tegaderm, 3M, MN).

Ulcer Wound Analysis

Digital photographs were taken before ulcer initiation, the day after, and every other day until closure. A silicone sheet with a 16 mm-in-diameter hole was centered on the wound before photography to allow for normalization of ulcer size during data analysis. Ulcer closure was defined as the time at which the wound was completely re-epithelialized. Ulcer wound area was determined using Image J software (National Institutes of Health, Bethesda, Md.).

Cytokine Quantification Via ELISA

Total protein was isolated from harvested wounds by homogenizing tissue in RIPA buffer in combination with a protease inhibitor. VEGF levels were measured using a murine quantikine VEGF ELISA kit (R&D Systems, Minneapolis, Minn.) according to the manufacturer's instructions.

Histology

After the mice were euthanized, wounds were harvested with a 2 mm rim of unwounded skin. Skin tissues were fixed in 4% paraformaldehyde overnight followed by serial dehydration in ethanol and embedding in paraffin. 5 μm sections were stained with H&E or picrosirius red. Frozen tissue samples for CD31 immunohistochemistry and DHE stain were prepared by immediate OCT embedding (Sakura Finetek USA, Inc., Torrance Calif.).

Assessment of Wound Vascularity

Frozen sections were immunohistochemically stained for CD31 (1°—1:100 Rb α CD31, Ab28364, Abcam, Cambridge, Mass.; 2°—1:400 AF547 Gt α Rb, Life Technologies). Nuclei were stained with DAPI. Image J (NIH, Bethesda, Md.) was used to binarize images taken with the same settings, and intensity thresholds were used to quantify CD31 staining based upon pixel-positive area averaged over 5 high power fields per sample. All measurements were performed by two blinded observers.

Assessment of Wound Collagen Density

Picrosirius red staining was performed according to the manufacturer's protocol (IHC World, Woodstock, Md.). Images were acquired using a light microscope (Leica 5000B) equipped with a polarization filter and camera (Leica DFC 500). Image J (NIH, Bethesda, Md.) was used to quantify collagen fibers per HPF. Quantification of the images was performed by a blinded observer.

DHE Staining

DHE staining was performed as previously described. Briefly, unfixed frozen sections were covered in $2 \times 10^{-6}$ M DHE solution and incubated at 37° C. for 30 min in a light protected humidified chamber. Images were taken the same day with a fluorescent microscope.

Statistical Analysis

Statistical analysis was performed using either ANOVA or an unpaired Student's t-test (MATLAB, Natick, Mass.). Values are presented as means±SEM. P values <0.05 were considered statistically significant.

Results

Figure 22A:
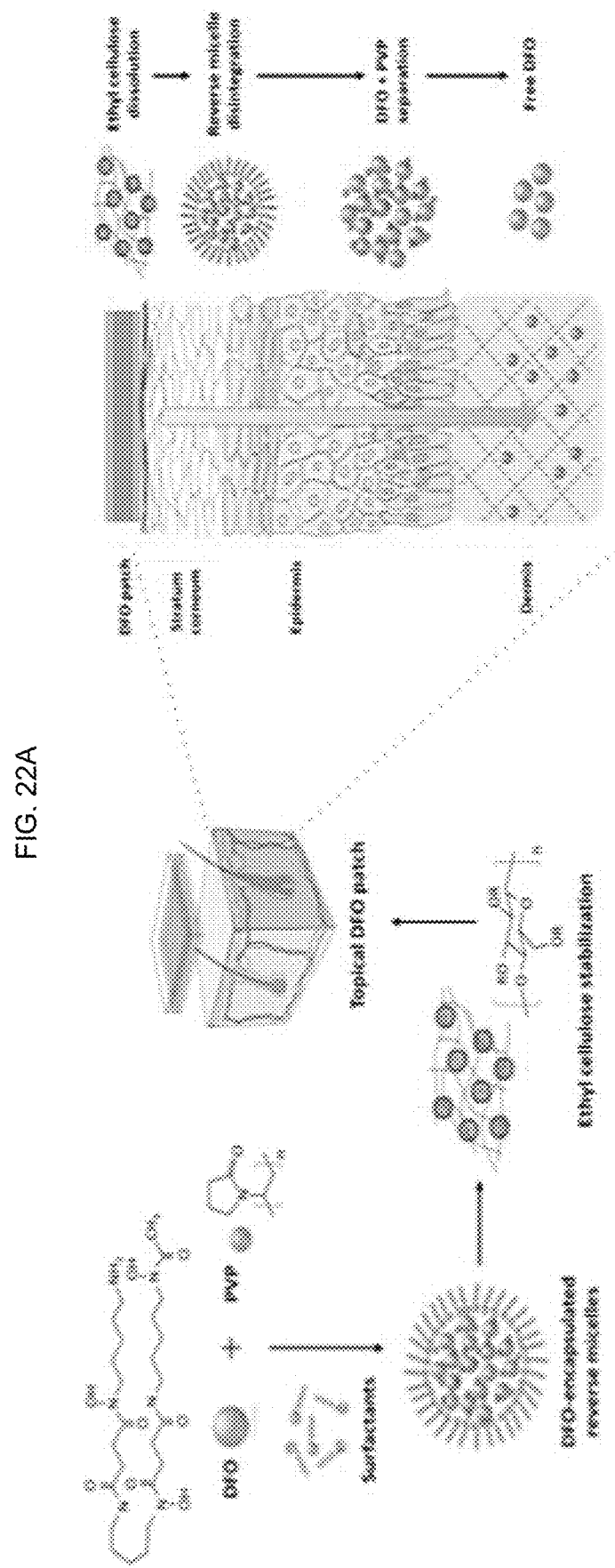

Development of a Transdermal Delivery System for DFO was formulated into a monolithic polymer matrix-type TDDS (FIG. 22A). This approach combines reverse micelle encapsulation of DFO by non-ionic surfactants with dispersion in a degradable slow release matrix, to allow for the targeted delivery of DFO molecules to the dermis. Specifically, DFO migrates from the TDDS to the skin following application, as demonstrated on scanning electron microscopy (SEM) (FIG. 22B). Once through the hydrophobic stratum corneum, the reverse micelles can then disintegrate in the more hydrophilic, aqueous environment of the dermis.

To confirm the morphology of the DFO-encapsulating reverse micelles and to analyze their structural composition, atomic force microscopy (AFM) and Raman spectroscopy imaging of chemical functionalities was performed (FIG. 22C-F). As expected, AFM analysis showed several, topographically similar large objects with a spheroidal shape (FIG. 22C). Moreover, AFM phase imaging, which is sensitive to local sample stiffness, visualized objects in the middle of every spheroid with a stiffness much higher than that of the surrounding shell, representing encapsulated DFO molecules (FIG. 22D). On Raman spectroscopy, doughnut-shaped Raman maps of lipids with the overall shape of the micelle shell were detected (FIG. 22C, E), while the DFO signal correlated with stiff clusters in AFM phase imaging (FIG. 22D, F). Together, these data indicate successful micellar encapsulation of DFO particles.

DFO Release and Permeation Studies In Vitro and In Vivo

Figure 22G:
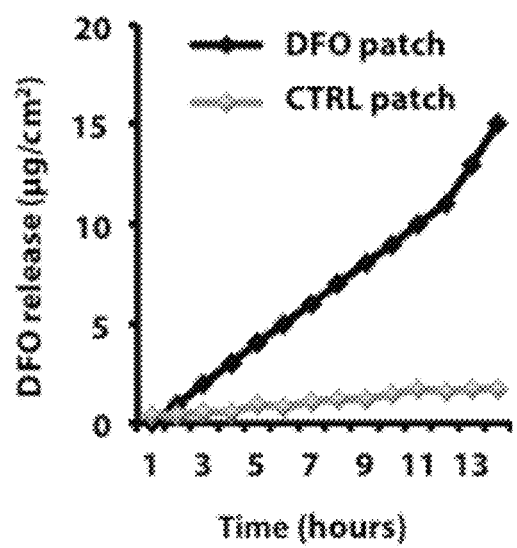
Figure 22H:
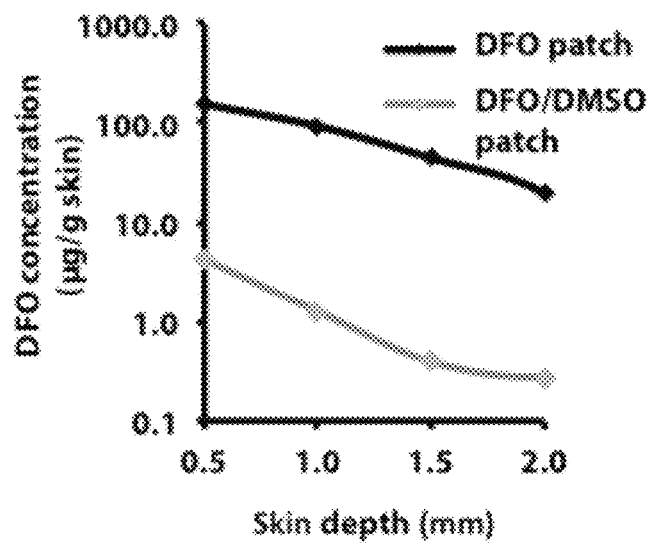
Figure 22I:
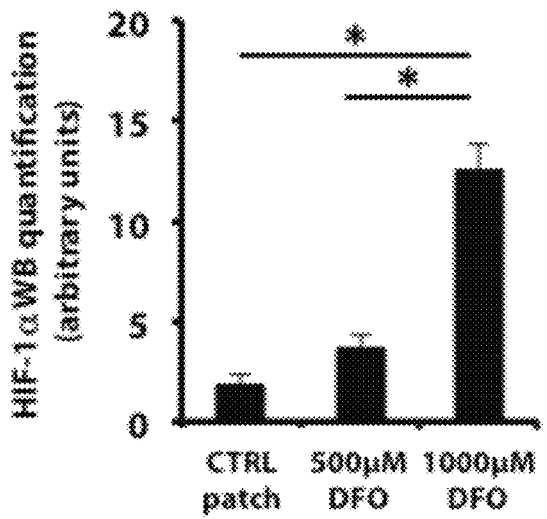

Next the release and permeation abilities of the TDDS containing 1% DFO in vitro and in vivo were evaluated (FIG. 22G-I). Over 14 hours of incubation in buffer solution under continuous shaking, the cumulative amount of drug released by the TDDS gradually increased in a linear manner, highlighting the potential benefits of the TDDS as a tool for slow and sustained delivery of DFO (FIG. 22G). To determine the dermal penetration of DFO delivered by the TDDS, in vitro skin permeation studies were performed using a Franz diffusion cell. TDDS application to excised full thickness human skin demonstrated penetration of DFO into the deep dermis within 24 hours (FIG. 22H). To test the efficacy of the micellar delivery of DFO, the TDDS was compared to an otherwise identical formulation containing the established chemical permeation enhancer dimethylsulphoxide (DMSO) instead of the reverse micelle forming surfactants. Almost no DFO was delivered into the dermis by the TDDS with the altered formulation (FIG. 22H). Furthermore, for both formulations no DFO could be detected in the receptor buffer of the Franz diffusion cell, consistent with the TDDS as a localized delivery system. To further investigate skin permeation of DFO delivered by the TDDS and its ability to stabilize HIF-1α in vivo, we assessed the efficacy of two differently dosed TDDS in uninjured diabetic mice. Transdermal DFO treatment resulted in a marginally increased HIF-1α stabilization at 0.5% and a significant increase of HIF-1α at 1% DFO. ($p<0.05$) (FIG. 22I). These data indicate support the efficacy of TDDS as a local delivery method for DFO. Due to its superior experimental profile, TDDSs with 1% DFO were used for all further in vivo experiments.

DFO Transdermal Treatment Enhances Wound Healing in Diabetic Mice

Figure 25A:
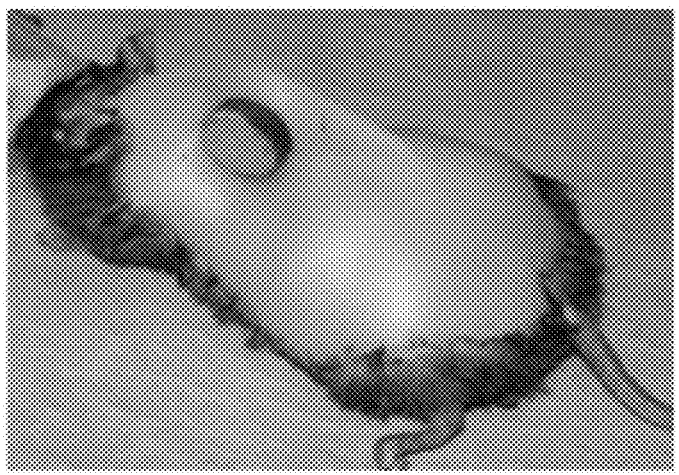
FIG. 25A-25D. Adaption of pressure induced ulcer model.
Figure 25B:
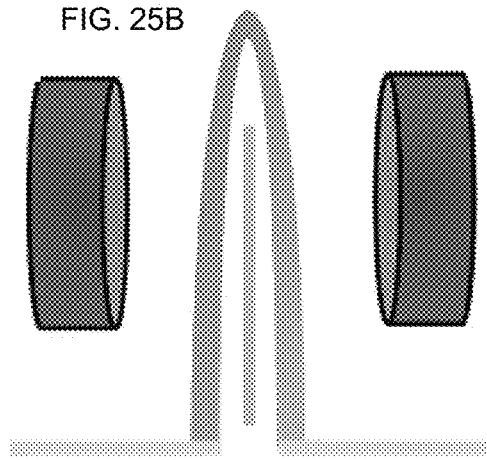
Figure 25C:
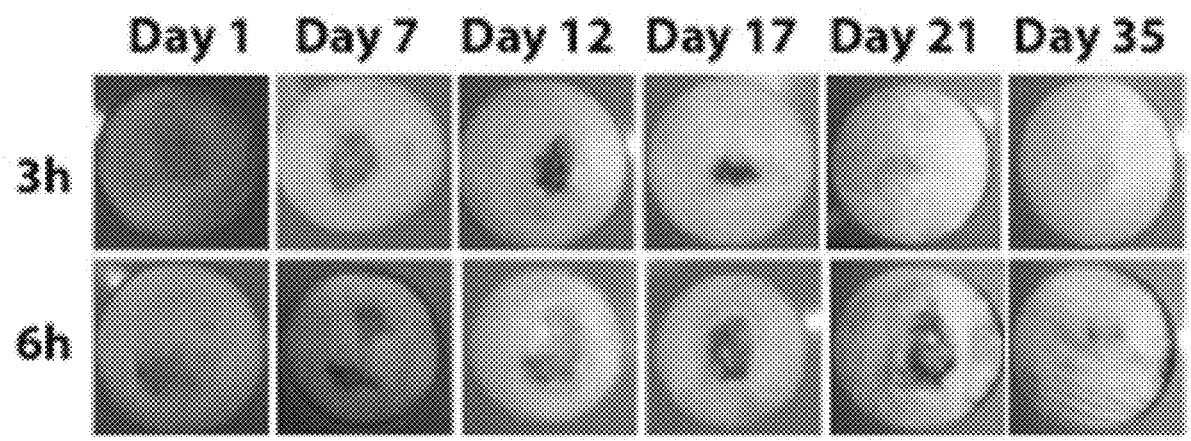
Figure 25D:
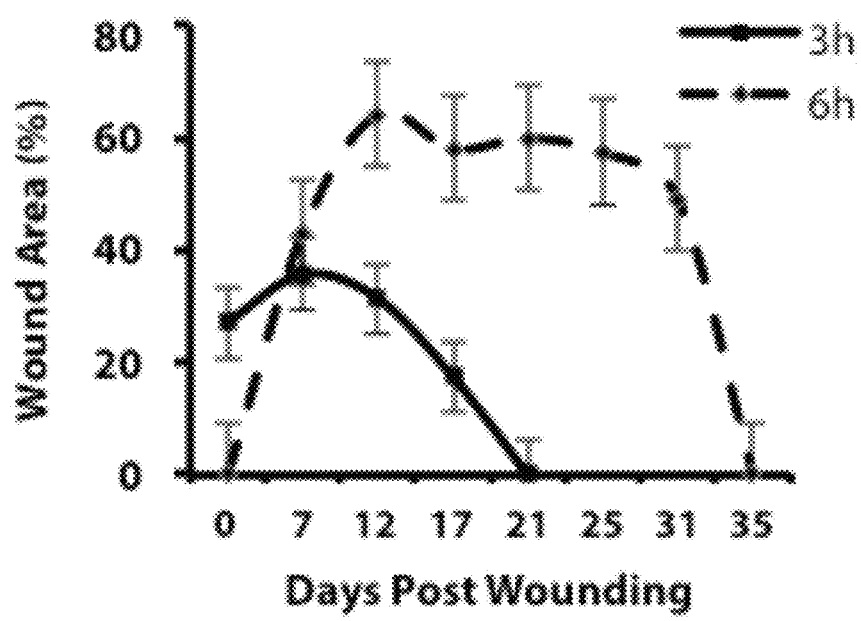

We adapted an established pressure-induced ulcer model for use in diabetic mice (db/db—leptin receptor-deficient). Pressure was applied intermittently by placing a ceramic magnet on both sides of a fold of dorsal skin (FIG. 25A, B), with 6 hour ischemia (magnets on)/reperfusion (magnets off) cycles resulting in the most consistent ulcer size and healing kinetics (FIG. 25C). With this protocol, skin ulcers with a thick eschar became apparent after 7 days, and the wounds completely healed by day 35 (FIG. 25D). No deaths, infections or other complications occurred and in subsequent experiments all diabetic ulcers were induced with 6-hour ischemia/reperfusion intervals.

Figure 23A:
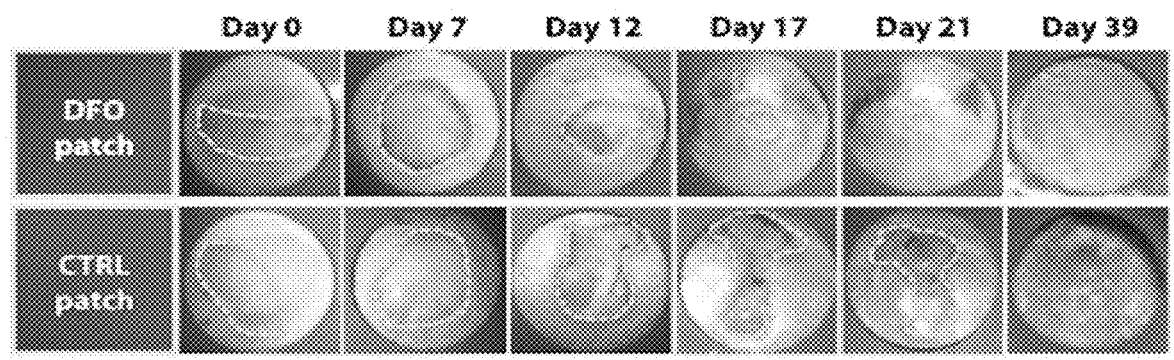
FIG. 23A-23I. DFO improves healing of diabetic ulcers.
Figure 23B:
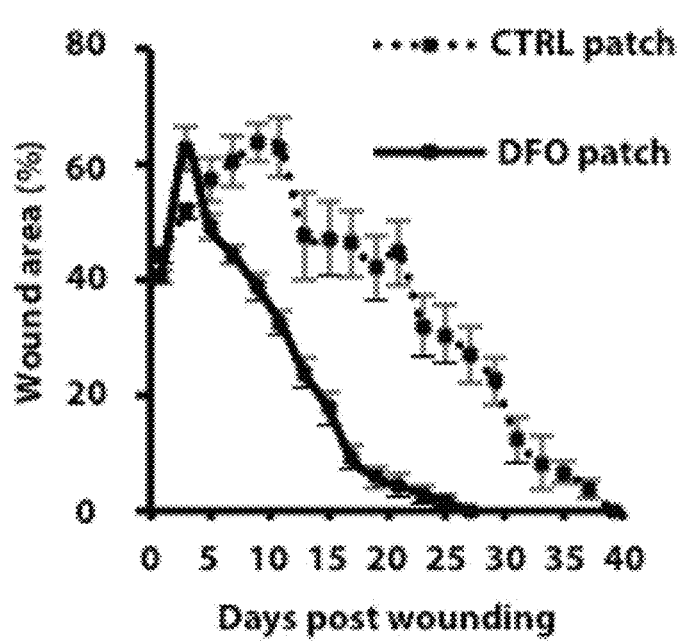

To examine the efficacy of transdermal DFO application in diabetic wounds, we applied either DFO TDDS or vehicle controls onto pressure-induced ulcers on the dorsum of diabetic mice. Transdermal treatment was begun 24 hours after the last ischemia/reperfusion cycle and the TDDS was changed every 48 hours until complete ulcer healing (FIG. 26A). TDDS delivery of the HIF-1α stabilizing agent DFO resulted in significantly accelerated healing (FIG. 23A, B). Complete resurfacing of ulcers occurred by 27 days in DFO-treated mice versus 39 days in untreated mice ($p<0.01$, FIG. 23B).

Transdermal DFO Delivery Increases HIF-1α Stabilization and VEGF Expression

Figure 23C:
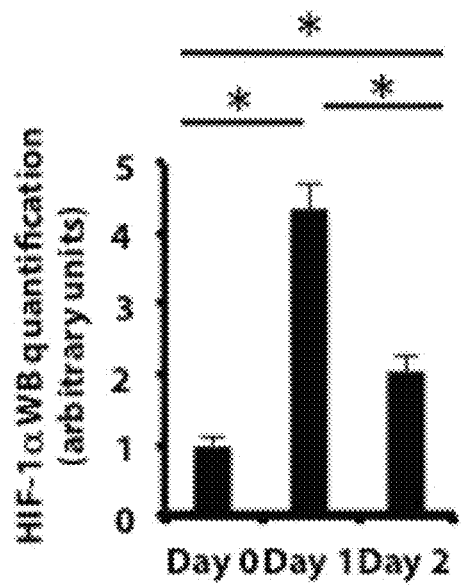
Figure 23D:
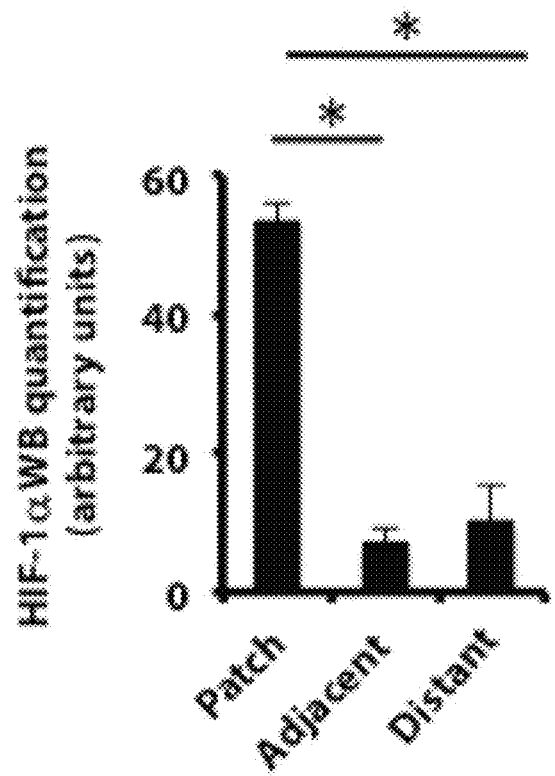

Next, we evaluated whether sustained DFO delivery to diabetic wounds stabilized HIF-1α and resulted in upregulation of its downstream effector VEGF. Following application of DFO TDDS to fully developed diabetic ulcers, (FIG. 26B), a significant increase in HIF-1α protein levels was observed, peaking at 24 hours post-application (FIG. 23C, $p<0.05$). Consistent with its efficacy as a local drug delivery system, the effect of HIF-1α stabilization was limited to the treated area, with adjacent and distant skin being unaffected (FIG. 23D, $p<0.01$).

Figure 23E:
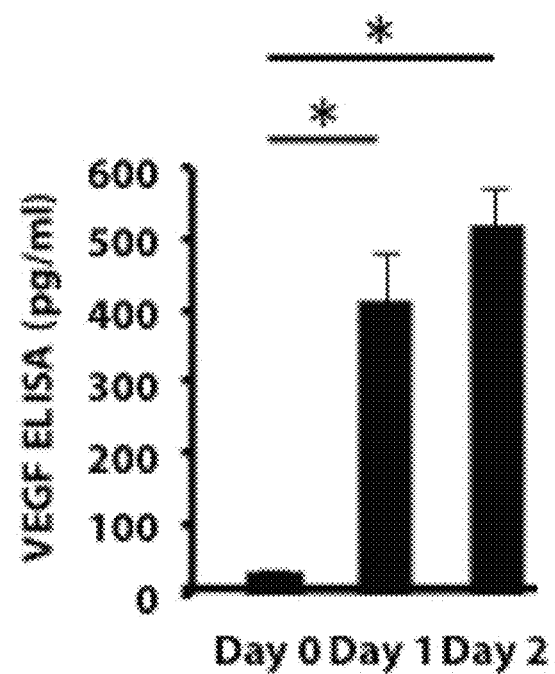

To assess the effects of HIF-1α stabilization on downstream effectors, we evaluated VEGF protein levels one and two days after TDDS application to fully developed diabetic ulcers. We observed significantly increased VEGF protein levels at both 24 and 48 hours after DFO TDDS application (FIG. 23E, $p<0.01$), congruent with the expected temporal dynamics of a downstream response.

DFO TDDS Treatment Enhances Neovascularization and Dermal Thickness

Figure 23F:
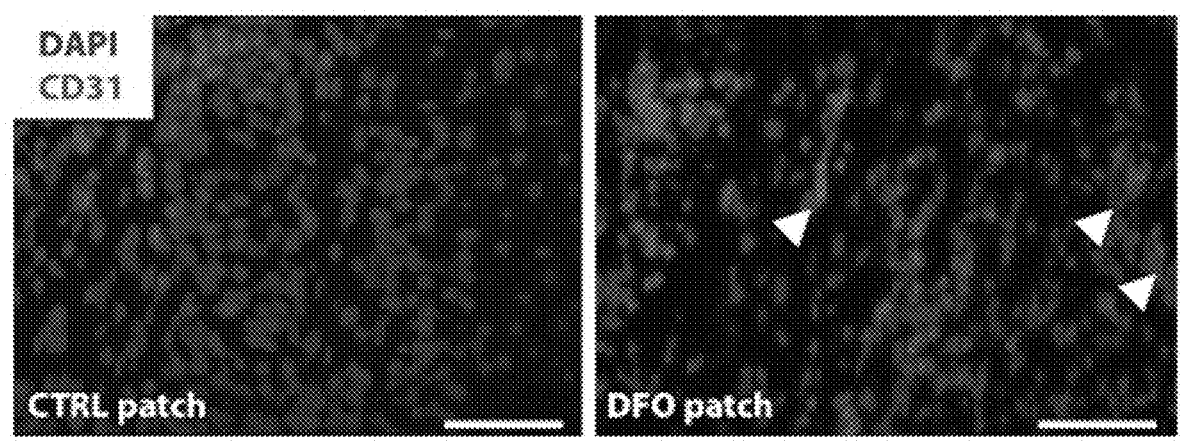
Figure 23G:
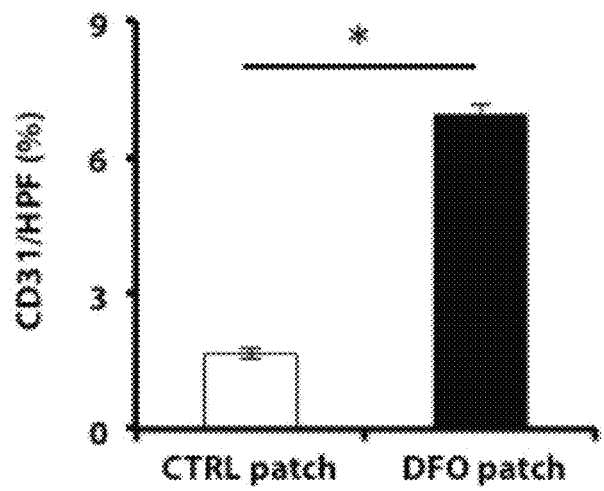
Figure 23H:
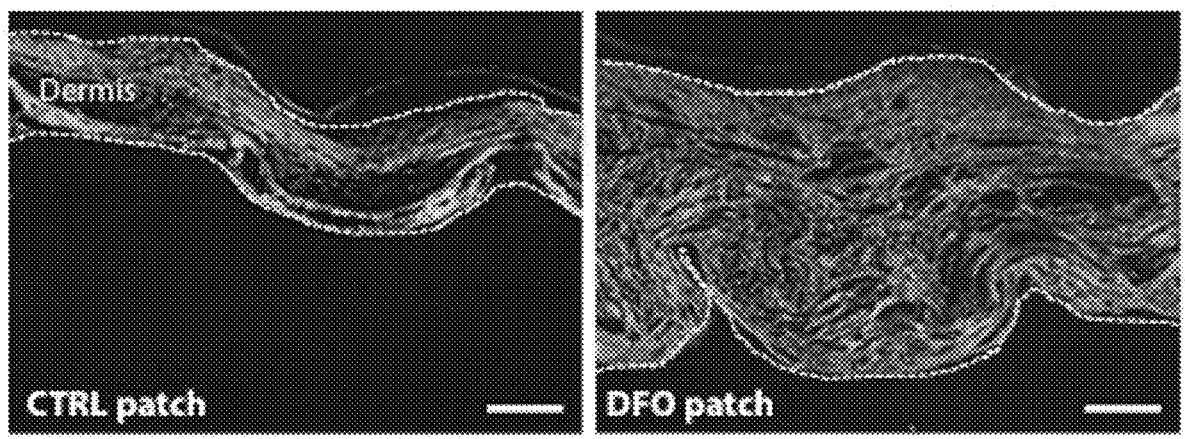
Figure 23I:
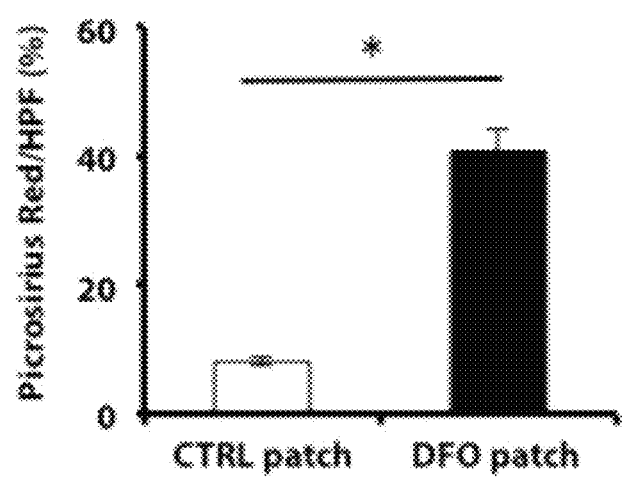

To further evaluate the positive effects of DFO TDDS treatment on ulcer healing, histological samples were taken upon complete wound closure. Healed DFO treated-diabetic ulcers exhibited significantly increased neovascularization compared to the vehicle control group, demonstrated by increased CD31 immonostaining (>3-fold, $p<0.01$, FIG. 23F, G). Further histological examination of the healed wounds showed that DFO TDDS treatment significantly improved the dermal thickness of healed diabetic ulcers, visualized as increased picrosirius red staining on polarized light images (>3-fold, $p<0.01$, FIG. 23H, I). These data indicate that DFO not only accelerates wound closure by increasing neovascularization but also effectively improves the quality of the healed skin.

Localized DFO Treatment Effectively Prevents Diabetic Ulcer Formation

Figure 24A:
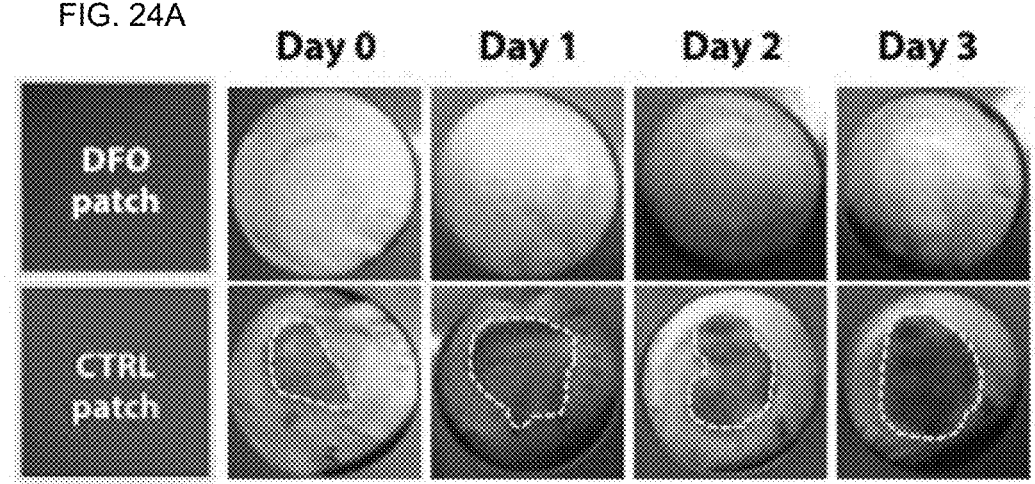
FIG. 24A-24G. Transdermal DFO treatment prevents ulcer formation in diabetic mice.
Figure 24B:
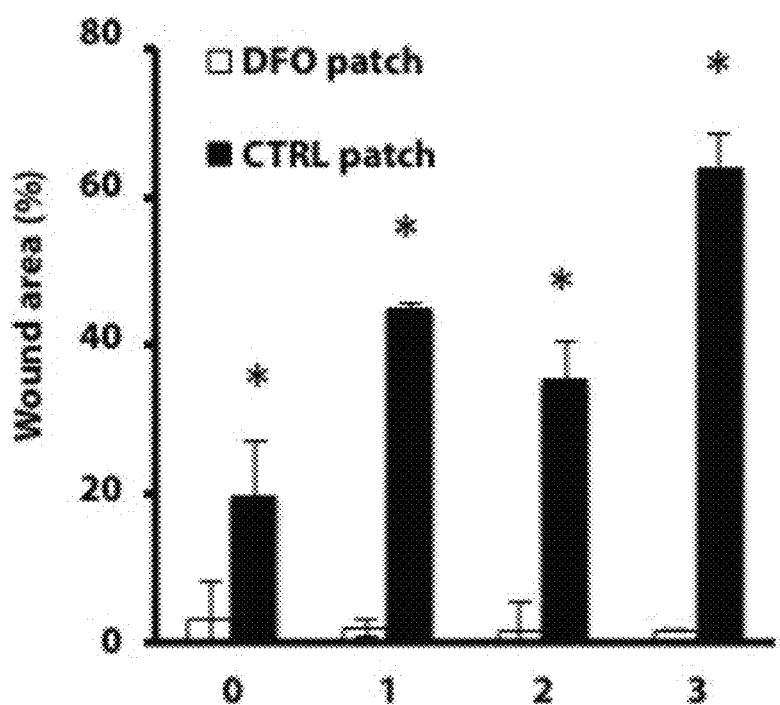
Figure 24C:
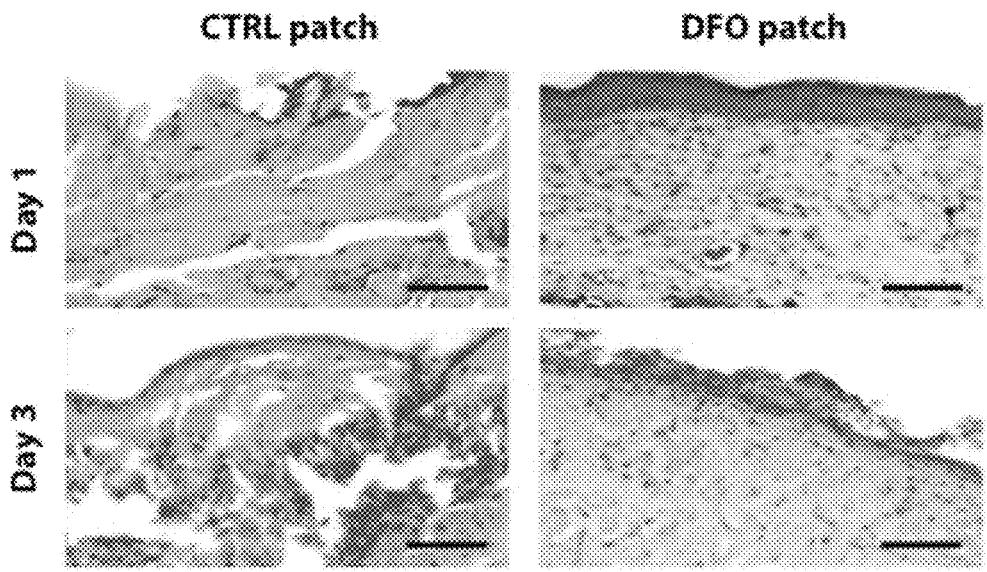

To investigate the prophylactic efficacy of DFO, we pre-treated the dorsal skin of diabetic mice for 48 hours with a DFO TDDS, followed by removal of the TDDS and ulcer induction as described above (FIG. 26C). Macroscopic monitoring of ulcer formation showed that skin pre-treatment resulted in prevention of ulcer formation and skin necrosis when compared with untreated controls (FIG. 24A, B, $p<0.01$). Histologic analysis confirmed loss of epithelial integrity, destruction of dermal architecture, and a profound inflammatory response in controls compared to the minimal tissue destruction observed in DFO TDDS-treated skin (FIG. 24C).

Figure 24D:
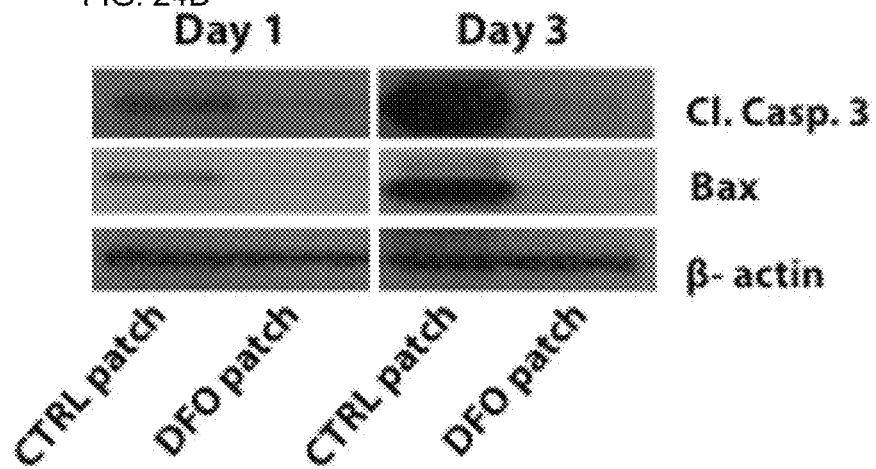
Figure 24E:
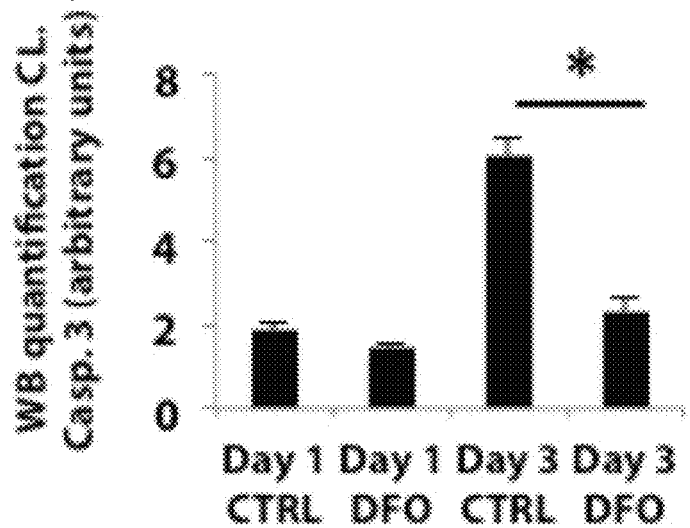
Figure 24F:
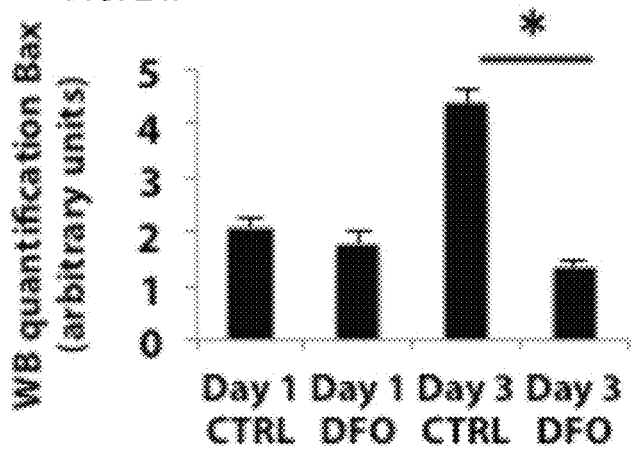

Previous evidence suggests that apoptosis contributes significantly to cell death following ischemia/reperfusion injury. To investigate whether DFO treatment attenuates these apoptotic effects, we performed analysis of protein levels of the apoptotic markers cleaved caspase 3 and Bax in DFO pre-treated and control wounds. DFO pre-treated mice showed a significant reduction of both apoptotic markers. (FIG. 24D-F, $p<0.05$).

Figure 24G:
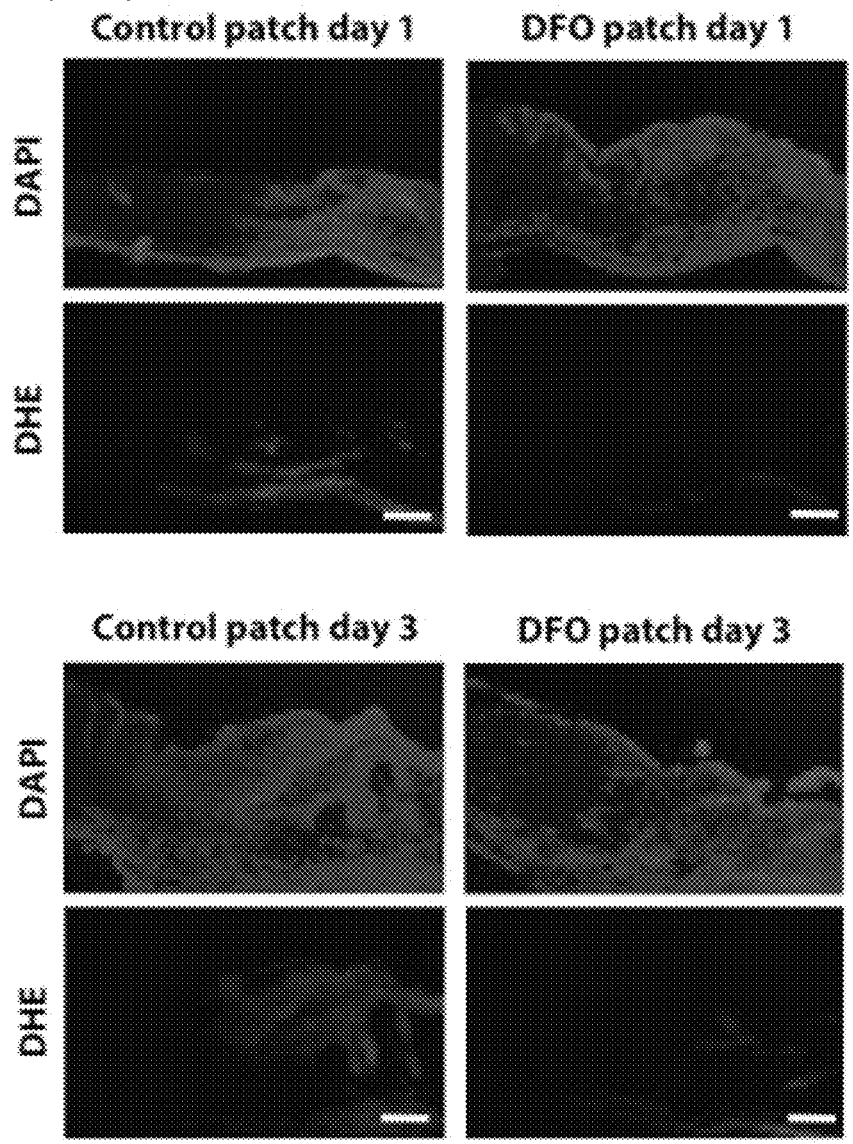

In ischemic tissues, DFO is known to reduce levels of reactive oxygen species (ROS), which play a major role in ulcer pathogenesis and persistence. Thus, we evaluated the influence of transdermal DFO treatment on superoxide levels using DHE immunofluorescent staining. Transdermal delivery of DFO resulted in a dramatic decrease of ROS accumulation, consistent with the observed reduction of apoptosis, skin necrosis and ulcer formation (FIG. 24G).

In summary, these findings support the transdermal DFO delivery system to address impaired diabetic wound healing. We demonstrate the ability to modulate established biologic pathways in diabetic ulcer formation and effectively augment tissue repair and restoration. Further, by prophylactically pre-loading skin with DFO, we demonstrate the ability to prevent pressure ulcer formation in a diabetic wound model.

Discussion

In this study, we developed a highly effective transdermal drug delivery system for the treatment and prevention of diabetic ulcers. Specifically, transdermal DFO delivery was found to effectively stabilize the transcription factor HIF-1α and up-regulate downstream VEGF secretion leading to accelerated diabetic wound healing. Moreover, DFO-treated mice exhibited significantly increased angiogenesis and dermal thickness as well as reduced apoptosis and ROS formation in a pressure-induced diabetic ulcer model. Pretreatment with a DFO TDDS effectively prevented ulcer formation in diabetic mice. As DFO is already FDA approved, this TDDS can be rapid translated into clinical application for the management of diabetic ulcers.

There are currently no available pharmacologic agents for the prevention of wound development and only one available to accelerate healing in existing wounds (becaplermin, PDGF-BB). Unfortunately, an increased cancer risk has been reported in patients treated with becaplermin, and it is not widely used for this and other reasons. Surprisingly, simple pressure offloading remains one of the mainstays of both treatment and prevention of chronic wounds but the compliance with these approaches in the long term remains low. Several other technologies such as silicone coated foam and hydrocolloids have attempted to reduce the risk of ulcer formation, but none of these have demonstrated significant efficacy. There is thus an eminent need for effective pharmacological approaches to address the tremendous healthcare burden of chronic wounds.

We view the modulation of HIF-1α as one promising approach to address this unmet need. DFO has an added advantage over PHD inhibitors such as DMOG, in that it also has a direct antioxidant effect, and is capable of reducing the oxidative stress associated with ischemia. In keeping with this mechanism, DFO plays a protective role during hypoxic preconditioning in brain and heart tissue, as well as in cutaneous ischemic preconditioning.

Consistent with its predicted therapeutic potential, we have previously demonstrated the efficacy of topical administration of DFO in healing diabetic wounds. In order to use DFO to prevent and treat diabetic ulcers in "at risk" patients, the development of a novel drug delivery platform was necessary. Recent innovative approaches for transdermal drug delivery include both chemical and physical enhancement. More aggressive chemical enhancers such as sulphoxides or alcohols improve the delivery efficiency for hydrophilic molecules, but are known to cause skin irritation and erythema. A less invasive method of augmenting stratum corneum permeation involves the use of non ionic surfactants. Tween 80 and Span 20 are widely regarded as safe and chemical enhanced matrix-type transdermal patches are a very cost effective way to deliver molecules across the skin barrier making it an attractive approach with high clinical translatability.

Our TDDS contains DFO mixed with reverse micelle forming surfactants dispersed in a polymer matrix, allowing for a controlled release over a predictable time period. Adapting this same combinatory approach of reverse micellar encapsulation with release controlling polymer matrices, our technology offers numerous other potential applications for local, transdermal delivery of hydrophilic drugs.

Our data suggest that preconditioning potential areas of ischemia/reperfusion can prevent ulcer formation in susceptible tissues. These findings have immense clinical importance, as the prevention of ulcer formation via a simple, topical TDDS would significantly reduce patient morbidity and healthcare costs associated with chronic diabetic wounds.

CONCLUSION

We describe the formulation of a novel biodegradable polymeric TDDS that allows for efficient delivery of DFO to diabetic wounds. Transdermal delivery of DFO was found to prevent diabetic ulcer formation when used prophylactically, and to decrease tissue necrosis and improve wound healing in pre-existing ulcers through increasing HIF-1α stabilization, decreased oxidative stress, reducing cellular apoptosis and tissue destruction, and promoting levels of VEGF and neovascularization. This represents, to our knowledge, the first description of pharmacological prevention of diabetic wounds. Given the status of DFO as an FDA-cleared molecule in clinical use for over three decades, its transdermal application would be an effective addition to the armamentarium for chronic wound treatment.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A method to treat skin, the method comprising:
   contacting skin topically with a transdermal patch comprising:
   a film comprising a HIF-1α potentiator encapsulated in reverse micelles within a biodegradable polymer;
   wherein the HIF-1α potentiator penetrates stratum corneum to release in underlying dermal tissues of the skin.

2. The method of claim 1, wherein the skin comprises a skin wound.

3. The method of claim 1, wherein the biodegradable polymer degrades over time to release the HIF-1α potentiator.

4. The method of claim 1, wherein the reverse micelles disintegrate in the dermal tissues.

5. The method of claim 1, wherein a level of HIF-1α protein in the dermal tissues increases to an increased level after contacting the skin with the transdermal patch.

6. The method of claim 1, wherein a level of VEGF protein in the dermal tissues increases to an increased level after contacting the skin with the transdermal patch.

7. The method of claim 6, wherein the increased level of VEGF protein is present 24 hours after contacting the skin with the transdermal patch.

8. The method of claim 6, wherein the increased level of VEGF protein is present 48 hours after contacting the skin with the transdermal patch.

9. The method of claim 1, wherein a thickness of the dermal tissues increases after contacting the skin with the transdermal patch.

10. The method of claim 1, wherein the contacting step comprises contacting the skin at a treatment site, thereby reducing diabetic ulcer formation at the treatment site.

11. The method of claim 1, wherein the contacting step comprises contacting the skin at a treatment site, thereby reducing pressure ulcer formation at the treatment site.

12. The method of claim 1, wherein the HIF-1α potentiator comprises an iron chelator.

13. The method of claim 12, wherein the iron chelator comprises deferoxamine (DFO).

14. The method of claim 12, wherein the iron chelator comprises deferasirox.

15. The method of claim 12, wherein the iron chelator comprises deferiprone.

* * * * *